US007534425B2

(12) United States Patent
Jentsch

(10) Patent No.: US 7,534,425 B2
(45) Date of Patent: *May 19, 2009

(54) ANIMAL MODEL AND CELL-LINE EXPRESSING MODIFIED CHLORINE CHANNEL

(75) Inventor: Thomas J. Jentsch, Hamburg (DE)

(73) Assignee: Neurosearch A/S, Ballerup (DK)

( * ) Notice: Subject to any disclaimer, the term of this patent is extended or adjusted under 35 U.S.C. 154(b) by 129 days.

This patent is subject to a terminal disclaimer.

(21) Appl. No.: 10/622,377

(22) Filed: Jul. 18, 2003

(65) Prior Publication Data

US 2004/0265837 A1    Dec. 30, 2004

Related U.S. Application Data

(63) Continuation of application No. PCT/DK02/00038, filed on Jan. 17, 2002.

(51) Int. Cl.
*A61K 48/00* (2006.01)
*A01N 65/00* (2006.01)
*C12N 5/00* (2006.01)
*C12N 5/02* (2006.01)

(52) U.S. Cl. ............... 424/93.2; 435/325; 424/93.7
(58) Field of Classification Search ............... 435/325
See application file for complete search history.

(56) References Cited

U.S. PATENT DOCUMENTS 5,434,058 A * 7/1995 Davidson .................. 435/69.1
6,686,193 B2 * 2/2004 Maher et al. ............. 435/285.2

FOREIGN PATENT DOCUMENTS

WO    WO 99/16909    8/1999
WO    WO 00/24707    4/2000

OTHER PUBLICATIONS

Jentsch, et al., 1999, Pflugers Arch—Eur. J. Physiology, 437: 783-795.*
Kawasaki et al. 1999, Am. J. Physiol., (Cell Physiol. 46) 277: C948-C954.*
Brandt and Jentsch, 1995, FEBS Letters, 377: 15-20.*
Buyse, et al., 1997, JBC, 272: 3615-3621.*
Agrawal and Kanimalla 2000, Molecular Medicine Today, 61: 72-81.*
Goswami et al. 2003, Journal of Molecular Evolution, 57:44-51.*
Lupo et al. 1997, JBC, 272: 31641-31647.*
Capecchi 1989, Science, 244: 1288-1292.*
Alberts et al. 1994, Molecular Biology of the Cell, Garland Publishing: New York, 3rd ed.*
Blaisdell et al., 1999, Am. J. Respir. Cell Mol. Biol., 20: 842-847.*
Chalaka et al. 1999, Am. J. Physiol., 277 (Lung Cell. Mol. Physiol. 21):L197-L203.*
Capecchi 1989, TIG, 5: 70-76.*
Simon et al. 1997, Nature Genetics, 17: 171-178.*
Gunther et al., 1998, PNAS, USA, 95: 8075-8080.*
Groneimeier et al., 1994, JBC, 269: 5963-5967.*
Nilius and Droogmmans, 2003, Acta Physiol. Scand., 177: 119-147.*
Simon et al, 1997, Nature Genetics, 17: 171-178.*
Gunter et al., 1998, PNAS, USA, 95: 8075-8080.*
Kornak et al., 2001, Cell, 104: 205-215.*
Jentsch et al., 2005, 115: 2039-2046.*
Doetschmann, 1999, Lab. Animal Sci., 49: 137-143.*
Moens et al., 1993, Development, 119: 485-499.*
Jacks et al., 1992, Nature, 359: 295-300.*
Kuehn et al., 1987, Nature, 326: 295-298.*
Jaenisch, 1988, Science, 240: 1468-1474.*
Gerlai, 1996, Trends Neurosci, 19: 177-181.*
Racay, 2002, Bratisl Lek Listy, 103: 121-126.*
Duff et al., 1996, Nature, 383: 710-713.*
Siegel et al., 2000, Bioessays, 22: 554-563.*
Young et al., 2003, Glycoconjugate Journal, 19: 257-262.*
Grant and Acosta, 1996, Fundamental and Applied Toxicology, 33: 71-82.*
Johnson-Muller and Gross, 1987, PNAS, USA, 75: 4417-4421.*
Davies et al., 2004, Molecular Vision, 10: 1028-1037.*
Tamm et al., 1999, Invest. Opthalmol. Vis. Sci. 40: 2577-2582.*
Comes et al., 2005, Experimental Eye Research, 80: 801-813.*
Gupta et al., 1996, The Journal of Immunology, 157: 2123-2128.*
Kulka et al., 2002, Inflammation Research 51: 451-456.*
Lee et al., 1998, Am. J. Physiol., 274: L450-L453.*
Mummery et al., 2005, Can. J. Physiol. Pharmacol., 83: 1123-1128.*
Siike Brandt, Thomas J. Jentsch; CIC-6 and CIC-7 are two novel broadly expressed members of the CLC chloride channel family; Center for Molecular Neurobiology Hamburg (ZMNH), FEBS Letters 377 (1995) 15-20.
Uwe Kornak, et al.; Complete genomic structure of the CLCN6 and CLCN7 putative chloride channel genes; Biochimica of Biophysica Acta 1447 (1999) 100-106.
Erna Cleiren, et al.; Albers-Schönberg disease (autosomal dominant osteopetrosis, type II) results from mutuations in the CICN7 chloride channel gene; Human Molecular Genetics, 2001, vol. 10, No. 25 2681-2867.

(Continued)

*Primary Examiner*—Joanne Hama
(74) *Attorney, Agent, or Firm*—Birch, Stewart, Kolasch & Birch, LLP

(57) ABSTRACT

The present invention relates to a test system for the identification and testing of active compounds which act on synaptic transmission (active compounds for treatment of neuronal diseases), which influence endo/exocytosis, which influence processing of proteins and in particular of active compounds which can be used for treatment of osteoporosis or Paget's disease, for treatment of neurological and neuromuscular diseases and other nerve diseases or as psychotropic pharmaceuticals. The invention furthermore relates to a genetically modified non-human mammal, in which one or more chloride channels from the group consisting of C1C-3, C1C-4, C1C-6 and C1C-7 are not expressed or are expressed non-functionally, and somatic cell lines which are derived from such an animal, and the use thereof for the identification and testing of substances which are suitable for inhibiting chloride channels, in particular C1C-3, C1C-4, C1C-5, C1C-6 and/or C1C-7.

26 Claims, 1 Drawing Sheet

OTHER PUBLICATIONS

Shinichi Uchida, et al.; Cloning and Expression of a PKC-Regulated Chloride Channel; Japanese Journal of Physiology, 44, Suppl. 2, S55-S62, 1994.

Paul H. Schlesinger, et al.; Characterization of the Osteoclast Ruffled Border Chloride Channel and Its Role in Bone Resorption; The Journal of Biological Chemistry vol. 272, No. 30, Issue of Jul. 25 pp. 18636-18643, 1997.

S.H.S. Pearce; Straightening out the renal tubule: advances in the molecular basis of the inherited tubulopathies; Q.J. Med 1998; 91:5-12.

Dayue Duan, et al.; Molecular identification of a volume-regulated chloride channel; Nature/vol. 390/417-421.

Uwe Kornak, et al.; Loss of the ClC-7 Chloride Channel Leads to Osteopetrosis in Mice and Man; Cell, vol. 104, 205-215, Jan. 26, 2001, Copyright © 2001 by Cell Press, pp. 205-215.

Sandra M. Stobrawa, et al.; Disruption of CIC-3, a Chloride Channel Expressed on Synaptic Vesicles, Leads to a Loss of the Hippocampus; Neuron, vol. 29, 185-196, Jan. 2001, Copyright © 2001 by Cell Press, pp. 185-196.

Nils Piwon, et al.; CIC-5 Cl -channel disruption impairs endocytosis in a mouse model for Dent's disease; Nature vol. 408/ Nov. 16, 2000, pp. 369-373.

David Clapham; How to Lose Your Hippocampus by Working on Chloride Channels; Neuron, vol. 29, Jan. 1-6, 2001, Copyright © 2001 by Cell Press, pp. 1-3.

Hartinger, et al., "An Anion Binding Site That Regulates the Glutamate Transporter of Synaptic Vesicles," Journal of Biological Chemistry, vol. 268, No. 31, pp. 23122-23127, 1993.

Ratcliff, et al., "Production of a Severe Cystic Fibrosis Mutation in Mice by Gene Targeting, Nature Genetics," vol. 4, pp. 35-41, 1993.

Vincent, et al., "Antisense Suppression of Potassium Channel Expression Demonstrates Its Role in Maturation of the Action Potential, Journal of Neuroscience," vol. 20, pp. 6087-6094, 2000.

Wang, et al., "The Role of CIC-3 in Volume-Activated Chloride Currents and Volume Regulation in Bovine Epithelial Cells Demonstrated by Antisense Inhibition," Journal of Physiology, vol. 524.1, pp. 63-75, 2000.

Tottene, et al., "$\alpha_{1E}$ Subunits Form the Pore of Three Cerebellar R-Type Calcium Channels with Different Pharmacological and Permeation Properties," Journal of Neuroscience, vol. 20, pp. 171-178, 2000.

Clarke, et al., "Defective Epithelial Chloride Transport in a Gene-Targeted Mouse Model of Cystic Fibrosis," Science, vol. 257, pp. 1125-1128, 1992.

Miesenböck, et al., "Visualizing Secretion and Synaptic Transmission with pH-Sensitive Green Fluorescent Proteins," Nature, vol. 394, pp. 192-195, 1998.

Maycoz, et al., "Glutamate Uptake by Brain Synaptic Vesicles," Journal of Biological Chemistry, vol. 263, pp. 15423-15428, 1988.

Schaertl, et al., "A Novel and Robust Homogeneous Fluorescence-Based Assay Using Nanoparticles for Pharmaceutical Screening and Diagnosis," Journal of Biomolecular Screening, vol. 5, pp. 227-237, 2000.

Yamamoto, et al., "Characterization of Renal Chloride Channel (CLCN5) Mutations in Dent's Disease," Journal of the American Society of Nephrology, vol. 11, pp. 1460-1468, 2000.

Sun, et al., "CD38/ADP-Ribosyl Cyclase: A New Role in the Regulation of Osteoclastic Bone Resorption," Journal of Cell Biology, vol. 146, pp. 1161-1171, 1999.

Kask, et al., "Fluorescence-Intensity Distribution Analysis and Its Application in Biomolecular Detection Technology," PNAS, vol. 96, pp. 13756-13761, 1999.

Kawasaki, et al., "Cloning and Expression of a Protein Kinase C-Regulated Chloride Channel Abundantly Expressed in Rat Brain Neuronal Cells," Neuron, vol. 12, pp. 597-604, 1994.

Thomas-Reetz, et al., "A γ-Aminobutyric Acid Transporter Driven by a Proton Pump is Present in Synaptic-Like Microvesicles of Pancreatic β-Cells," Proceedings of the National Academy of Sciences USA, vol. 90, pp. 5317-5321, 1993.

Overly, et al., "Quantitative Measurement of Intraorganelle pH in the Endosomal-Lysosomal Pathway in Neurons by Using Ratiometric Imaging with Pyranine," Proceedings of the National Academy of Sciences USA, vol. 92, pp. 3156-3160, 1995.

Xia, et al., "Localization of Rat Cathepsin K in Osteoclasts and Resorption Pits: Inhibition of Bone Resorption and Cathepsin K-Activity by Peptidyl Vinyl Sulfones," Biological Chemistry, vol. 380, pp. 679-687, 1999.

Yeager, et al., "Constructing Immortalized Human Cell Lines," Current Opinion in Biotechnology, vol. 10, pp. 465-469, 1999.

Palo, et al., "Fluorescence Intensity Multiple Distributions Analysis: Concurrent Determination of Diffusion Times and Molecular Brightness," Biophysical Journal, vol. 79, pp. 2858-2866, 2000.

Diwu, et al., "A Novel Acidotropic pH Indicator and Its Potential Application in Labeling Acidic Organelles of Live Cells," Chemistry & Biology, vol. 6, pp. 411-418, 1999.

Reimer, et al., "Vascular Neurotransmitter Transport and the Presynaptic Regulation of Quantal Size," Current Opinion in Neurobiology, vol. 8, pp. 405-412, 1998.

Gasnier, "The Loading of Neurotransmitters Into Synaptic Vesicles," Biochimie, vol. 82, pp. 327-337, 2000.

Karlsson, "Real-Time Competitive Kinetic Analysis of Interactions Between Low-Molecular Weight Ligands in Solution and Surface-Immobilized Receptors," Analytical Biochemistry, vol. 221, pp. 142-151, 1994.

Frostell-Karlsson, et al., "Biosensor Analysis of the Interaction Between Immobilized Human Serum Albumin and Drug Compounds for Prediction of Human Serum Albumin Binding Levels," Journal of Medical Chemistry, vol. 43, pp. 1986-1992, 2000.

Parmjit, et al., "Direct Derivation of Conditionally Immortal Cell Lines from an H-2K$^b$-tsA58 Transgenic Mouse," Proceedings of the National Academy of Sciences USA, vol. 88, pp. 5096-5100, 1991.

Llopis, et al., "Measurement of Cytosolic, Mitochondrial, and Golgi pH in Single Living Cells with Green Fluorescent Proteins," Proceedings of the National Academy of Sciences USA, vol. 95, pp. 6803-6808, 1998.

Whitehead, et al., "Establishment of Conditionally Immortalized Epithelial Cell Lines from Both Colon and Small Intestine of Adult H-2K$^b$-tsA58 Transgenic Mice," Proceedings of the National Academy of Sciecnes, USA, vol. 90, pp. 587-591, 1993.

Markgren, et al., "Kinetic Analysis of the Interaction Between HIV-1 Protease and Inhibitors Using Optical Biosensor Technology," Analytical Biochemistry, vol. 279, pp. 71-78, 2000.

Williams, "Biotechnology Match Making: Screening Orphan Ligands and Receptors," Current Opinion in Biotechnology, vol. 11, p. 42-46, 2000.

Beerheide, et al., "Potential Drugs Against Cervical Cancer: Zinc-Ejecting Inhibitors of the Human Papillomavirus Type 16 E6 Oncoprotein," Journal of the National Cancer Institute, vol. 91, pp. 1211-1220, 1999.

Jen, et al., "Suppression of Gene Expression by Targeted Disruption of Messenger RNA: Available Options and Current Strategies," Stem Cells, vol. 18, pp. 307-319, 2000.

Deckert, et al., "Development and Validation of an IL-6 Immuno-Receptor Assay Based on Surface Plasmon Resonance," Journal of Pharmaceutical and Biomedical Analysis, vol. 23, pp. 403-412, 2000.

Shioi, et al., "Glutamate Uptake Into Synaptic Vesicles of Bovine Cerebral Cortex and Electrochemical Potential Difference of Proton Across the Membrane," Biochemistry Journal, vol. 258, pp. 499-504, 1989.

Kubisch, et al., C1C-1 Chloride Channel Mutations in Myotonia Congenita: Variable Penetrance of Mutations Shifting the Voltage Dependence, Human Molecular Genetics, vol. 7, pp. 1753-1760, 1998.

Lorenz, et al., "Genomic Organization of the Human Muscle Chloride Channel CIC-1 and Analysis of Novel Mutations Leading to Becker-Type Myotonia," Human Molecular Genetics, vol. 3, pp. 941-946, 1994.

Tycko, et al., "Rapid Acidification of Endocytic Vesicles Containing $\alpha_2$-Macroglobulin," Cell, vol. 28, pp. 643-651, 1982.

Boyde, et al., "Resorption of Dentine by Isolated Osteoclasts in vitro," British Dental Journal, vol. 156, pp. 216-220, 1984.

Chapman, et al., "Retrieval of TGN Proteins From the Cell Surfaces Requires Endosomal Acidification," The EMBO Journal, vol. 13, pp. 2305-2312, 1994.

Katakura, et al., "Immortalization by Gene Transfection," Methods in Cell Biology, vol. 57, pp. 69-91, 1998.

Hell, et al., "Uptake of GABA By Rat Brain Synaptic Vesicles Isolated By a New Procedure," The EMBO Journal, vol. 7, pp. 3023-3029, 1988.

Giovanna, et al., "Synergy Between $Apc^{min}$ and an Activated $ras$ Mutation Is Sufficient to Induce Colon Carcinomas," Molecular and Cellular Biology, vol. 16, pp. 884-891, 1996.

Nako, et al., "Inhibition by Antisense Oligonucleatides of Plasma Membrane $Ca^{2+}$ ATPase in Vascular Endothelial Cells," European Journal of Pharmacology, vol. 387, pp. 273-277, 2000.

Dorin, et al., "Cystic Fibrosis in the Mouse by Targeted Insertional Mutagenesis," Nature, vol. 359, pp. 211-215, 1992.

Johnson, et al., "Endosome Acidifcation and Receptor Trafficking: Bafilomycin $A_1$ Slows Receptor Externalization by a Mechanism Involving the Receptor's Internalization Motif," Molecular Biology of the Cell, vol. 4, pp. 1251-1266, 1993.

Wu, et al., "|39| Studying Organelle Physiology with Fusion Protein-Targeted Avidin and Fluorescent Biotic Conjugates," Methods in Enzymology, vol. 327, pp. 546-564, 2000.

Van Noorden, et al., "Localization of Cathepsin B Activity in Fibroblasts and Chondrocytes by Continuous Monitoring of the Formation of Final Fluorescent Reaction Product Using 5-Nitrosalicylaldehyde," Histochemical Journal, vol. 19, pp. 483-487, 1987.

Mellman, "The Importance of Being Acid: The Role of Acidification in Intracellular Membrane Traffic," Journal Experimental Biology, vol. 172, pp. 39-45, 1992.

Presley, et al., "Bafilomycin $A_1$ Treatment Retards Transferrin Receptor Recycling More Than Bulk Membrane Recycling," Journal of Biological Chemistry, vol. 272, pp. 13929-13936, 1997.

Tabb, et al., "Glutamate Transport into Synaptic Vesicles," Journal of Biological Chemistry, vol. 267, pp. 15412-15418, 1992.

Leconte, et al., "Impairment of Rod cGMP-Gated Channel α-Subunit Expression Leads to Photoreceptor and Bipolar Cell Degeneration," Investigative Ophthalmology & Visual Science, vol. 41, pp. 917-926, 2000.

Lloyd, et al., "Characterisation of Renal Chloride Channel, CLCN5, Mutations in Hypercalciuric Nephrolithiasis (kidney stones) Disorders," Human Molecular Genetics, vol. 6, pp. 1233-1239, 1997.

Brenner, et al., "Vasoregulation by the β1 Subunit of the Calcium-Activated Potassium Channel," Nature, vol. 407, pp. 870-876, 2000.

Brandt, et al., "ClC-6 and ClC-7 Are Two Novel Broadly Expressed Members of the CLC Chloride Channel Family," FEBS Letters, vol. 377, pp. 15-20, 1995.

Inoue, et al., "Visualization of Acidic Compartments in Cultured Osteoclasts by Use of an Acidotrophic Amine as a Marker for Low pH," Cell Tissue Research, vol. 298, pp. 527-537, 1999.

Pusch, et al., "Mutations in Dominant Human Myotonia Congenita Drastically Alter the Voltage Dependence of the ClC-1 Chloride Channel," Neuron, vol. 15, pp. 1455-1463, 1995.

Llyod, et al., "A Common Molecular Basis for Three Inherited Kidney Stone Diseases," Nature, vol. 39, pp. 445-449, 1996.

Meyer-Kleine, et al., "Spectrum of Mutations in the Major Human Skeletal Muscle Chloride Channel Gene (CLCN1) Leading to Myotonia," American Journal of Human Genetics, vol. 57, pp. 1325-1334, 1995.

Baron, et al., "Cell-Mediated Extracellular Acidification and Bone Resorption: Evidence for a Low pH in Resorbing Lacunae and Localization of a 100-kD Lysosomal Membrane Protein at the Osteoclast Ruffled Border," Journal of Cell Biology, vol. 101, pp. 2210-2222, 1985.

Demaurex, et al., "Mechanism of Acification of the *trans*-Golgi Network (TGN) in Situ Measurements of pH Using Retreival of TGN38 and Furin From the Cell Surface," Journal of Biological Chemistry, vol. 273, pp. 2044-2051, 1997.

Igarashi, et al., "Functional Characterization of Renal Chloride Channel, CLCN5, Mutations Associated with Dent's$_{Japan}$ Disease," Kidney International, vol. 54, pp. 1850-1856, 1998.

Failke, "Molecular Mechanisms of Ion Conduction in ClC-Type Chloride Channels: Lessons from Disease-Causing Mutations," Kidney International, vol. 57, pp. 780-786, 2000.

Kneen, et al., "Green Fluorescent Protein as a Noninvasive Intracellular pH Indicator," Biophysical Journal, vol. 74, pp. 1591-1599, 1998.

Zen, et al., "Second Messengers Regulate Endosomal Acidification in Swiss 3T3 Fibroblasts," Journal of Cell Biology, vol. 119, pp. 99-110, 1992.

Lewalle, et al., "Inhibition of P210 Expression in Chronic Myeloid Leukaemia: Oligonucleotides and/or Transduced Antisense Sequences," Leukemia and Lymphoma, vol. 11, pp. 139-143, 1993.

Marschall, et al., "Inhibition of Gene Expression with Ribozymes," Cellular and Molecular Neurobiology, vol. 14, pp. 523-538, 1994.

Borsani, et al., "Characterization of Human and Murine Gene (CLCN3) Sharing Similarities to Voltage-Gated Chloride Channels and to a Yeast Integral Membrane Protein," Genomics, vol. 27, pp. 131-141, 1995.

Siegel, et al., "A Genetically Encoded Optical Probe of Membrane Voltage," Neuron, vol. 19, pp. 735-741, 1997.

Presley, et al., "The *End2* Mutation in CHO Cells Slows the Exit of Transferrin Receptors from the Recycling Compartment but Bulk Membrane Recycling is Unaffected," Journal of Cell Biology, vol. 122, pp. 1231-1241, 1993.

Steinmeyer, et al., "Multimeric Structure of ClC-1 Chloride Channel Revealed by Mutations in Dominant Myotonia Congenita (Thomsen)," EMBO Journal, vol. 13, pp. 737-743, 1994.

Ratcliff, et al., "Disruption of the Cystic Fibrosis Transmembrane Conductance Regulator Gene in Embryonic Stem Cells by Gene Targeting," Transgenic Research, vol. 1, pp. 177-181, 1992.

Schwappach, et al., "Golgi Localization and Functionally Important Domains in the $NH_2$ and COOH Terminus of the Yeast CLC Putative Chloride Channel Geflp," Journal of Biological Chemistry, vol. 273, pp. 15110-15118, 1998.

Liu, et al., "Ribozyme Ablation Demonstrates That the Cardiac Subtype of the Voltage-Sensitive Calcium Channel Is the Molecular Transducer of 1,25-Dihydroxyvitamin $D_3$-Stimulated Calcium Influx in Osteoblastic Cells," Journal of Biological Chemistry, vol. 275, pp. 8711-8718, 2000.

Hell, et al., "Energy Dependence and Functional Reconstitution of the γ-Aminobutyric Acid Carrier from Synaptic Vesicles," Journal of Biological Chemistry, vol. 265, pp. 2111-2117, 1990.

Matsumura, et al., "Overt Nephrogenic Diabetes Insipidus in Mice Lacking the CLC-K1 Chloride Channel," Nature Genetics, vol. 21, pp. 95-98, 1999.

Clague, et al., "Vacuolar ATPase Activity Is Required for Endosomal Carrier Vesicle Formation," Journal of Biological Chemistry, vol. 269, pp. 21-24, 1994.

Laitala-Leinonen, et al., "Inhibition of Intravacuolar Acidification by Antisense RNA Decreases Osteoclast Differentiation and Bone Resorption In Vitro," Journal of Cell Science, vol. 112, pp. 3657-3666, 1999.

Ilvesaro, et al., "Bone-Resorbing Osteoclasts Contain Gap-Junctional Connexin-43," Journal of Bone and Mineral Research, vol. 15, pp. 919-926, 2000.

Udagawa, et al., "Osteoblasts/Stromal Cells Stimulate Osteoclast Activation Through Expression of Osteoclast Differentiation Factor/RANKL but Not Macrophage Colony-Stimulating Factor," Bone, vol. 25, pp. 517-523, 1999.

Lloyd, et al., Idiopathic Low Molecular Weight Proteinuria Associated with Hypercalciuric Nephrocalcinosis in Japanese Children Is Due to Mutations of the Renal Chloride Channel (CLCN5), Journal of Clinical Investigation, vol. 99, pp. 967-974, 1997.

Lee, et al., "Targeted Disruption of the *Kulqt1* Gene Causes Deafness and Gastric Hyperplasia in Mice," Journal of Clinical Investigation, vol. 106, pp. 1447-1455, 2000.

Montrose-Rafizadeh, et al., "Gene Targeting of a CFTR Allele in HT29 Human Epithelial Cells," Journal of Cellular Physiology, vol. 170, pp. 299-308, 1997.

Redey, et al., "Osteoclast Adhesion and Activity on Synthetic Hydroxyapatite, Carbonated Hydroxyapatite, and Natural Calcium Carbonate: Relationship to Surface Energies," Journal of Biomedical Research, vol. 45, pp. 140-147, 1999.

Brussaard, "Antisense Oligonucleotides Induce Functional Deletion of Ligand Gated Ion Channels in Cultured Neurons and Brain Explants," Journal of Neuroscience Methods, vol. 71, pp. 55-64, 1997.

Friedrich, et al., "Mutational Analysis Demonstrates That CIC-4 and CIC-5 Directly Mediate Plasma Membrane Currents," Journal of Biological Chemistry, vol. 27, pp. 896-902, 1999.

Gronemeier, et al., "Nonsense and Missense Mutations in the Muscular Chloride Channel Gene clc-1 of Myotonic Mice," Journal of Biological Chemistry, vol. 269, pp. 5963-5967, 1994.

Schapiro, et al., "Determinants of the pH of the Golgi Complex," Journal of Biological Chemistry, vol. 275, pp. 21025-21032, 2000.

Schmidt-Rose, et al., "Reconstitution of Functional Voltage-Gated Chloride Channels From Complementary Fragments of CLC-1," Journal of Biological Chemistry, vol. 272, pp. 20515-20521, 1997.

Sterrer, et al., "Fluorescence Correlation Spectroscopy (FCS)—A Highly Sensitive Method to Analyze Drug/Target Interactions," Journal of Receptor & Signal Transduction Research, vol. 17, pp. 511-520, 1997.

Chambers, et al., "Resorption of Bone by Isolated Rabbit Osteoclasts," Journal of Cell Science, vol. 66, pp. 383-399, 1984.

Vandewalle, "Immortalized Kidney Cells Derived from Transgenic Mice Harboring L-Type Pyruvate Kinase and Vimentin Promoters," Experimental Nephrology, vol. 7, pp. 386-393, 1999.

Gökhan, et al., "Generation and Regulation of Developing Immortalized Neural Cell Lines," Methods, vol. 16, pp. 345-358, 1998.

Okazaki, et al., "Thiazolidinediones Inhibit Osteoclast-Like Cell Formation and Bone Resorption in Vitro," Endocrinology, vol. 140, pp .5060-5065, 1999.

Luyckx, et al., "Diet-Dependent Hypercalciuria in Transgenic Mice with Reduced CLC5 Chloride Channel Expression," PNAS, vol. 96, pp. 12174-12179, 1999.

* cited by examiner

SEQUENCE LISTING

<160> NUMBER OF SEQ ID NOS: 14

<210> SEQ ID NO 1
<211> LENGTH: 3953
<212> TYPE: DNA
<213> ORGANISM: Homo sapiens

```
<220> FEATURE:
<221> NAME/KEY: gene
<222> LOCATION: (1)..(3953)
<223> OTHER INFORMATION: CLCN3
<220> FEATURE:
<221> NAME/KEY: CDS
<222> LOCATION: (489)..(2951)
<223> OTHER INFORMATION: ClC-3

<400> SEQUENCE: 1
ggggtcacgg gcgaactaga acactgggaa aggggctgca ggttccggac cggaccggcc      60
ctgacccgga ataatgagca aggagggtgt ggtgggttga agccatcct actttactcc      120 cgagttagag catggattca gttttagtct aaggggggaa gtgagattgg agatttttat     180
ttttaatttt gggcagaagc aggttgactc tagggatctc cagagcgaga ggatttaact     240
tcatgttgct cccgtgtttg aaggaggaca ataaaagtcc caccgggcaa aattttcgta     300
acctctgcgg tagaaaacgt caggtatctt ttaaatcgcg atagttttcg ctgtgtcagg     360
ctttcttcgg tggagctccg agggtagcta ggttctaggt ttgaaacaga tgcagaatcc     420
aaaggcagcg caaaaaacag ccaccgattt tgctatgtct ctgagctgcg agataatcag     480 acagctaa atg gag tct gag cag ctg ttc cat aga ggc tac tat aga aac       530
         Met Glu Ser Glu Gln Leu Phe His Arg Gly Tyr Tyr Arg Asn
           1               5                   10 agc tac aac agt ata aca agt gca agt agt gat gag gaa ctt tta gat       578
Ser Tyr Asn Ser Ile Thr Ser Ala Ser Ser Asp Glu Glu Leu Leu Asp
 15                  20                  25                  30 gga gca ggt gtt att atg gac ttt caa aca tct gaa gat gac aat tta       626
Gly Ala Gly Val Ile Met Asp Phe Gln Thr Ser Glu Asp Asp Asn Leu
             35                  40                  45 tta gat ggt gac act gca gtt gga act cat tat aca atg aca aat gga       674
Leu Asp Gly Asp Thr Ala Val Gly Thr His Tyr Thr Met Thr Asn Gly
         50                  55                  60 ggc agc att aac agt tct aca cat tta ctg gat ctt ttg gat gaa cca       722
Gly Ser Ile Asn Ser Ser Thr His Leu Leu Asp Leu Leu Asp Glu Pro
 65                  70                  75 att cca ggt gtt ggt aca tat gat gat ttc cat act att gat tgg gtg       770
Ile Pro Gly Val Gly Thr Tyr Asp Asp Phe His Thr Ile Asp Trp Val
         80                  85                  90 cga gaa aaa tgt aaa gac aga gaa agg cat aga cgg atc aac agc aaa       818
Arg Glu Lys Cys Lys Asp Arg Glu Arg His Arg Arg Ile Asn Ser Lys
 95                 100                 105                 110 aag aaa gaa tca gca tgg gaa atg aca aaa agt ttg tat gat gcg tgg       866
Lys Lys Glu Ser Ala Trp Glu Met Thr Lys Ser Leu Tyr Asp Ala Trp
            115                 120                 125 tca gga tgg cta gta gta aca cta aca gga ttg gca tca ggg gca ctg       914
Ser Gly Trp Leu Val Val Thr Leu Thr Gly Leu Ala Ser Gly Ala Leu
        130                 135                 140 gcc gga tta ata gac att gct gcc gat tgg atg act gac cta aag gag       962
Ala Gly Leu Ile Asp Ile Ala Ala Asp Trp Met Thr Asp Leu Lys Glu
    145                 150                 155 ggc att tgc ctt agt gcg ttg tgg tac aac cac gaa cag tgc tgt tgg      1010
Gly Ile Cys Leu Ser Ala Leu Trp Tyr Asn His Glu Gln Cys Cys Trp
160                 165                 170 gga tct aat gaa aca aca ttt gaa gag agg gat aaa tgt cca cag tgg      1058
Gly Ser Asn Glu Thr Thr Phe Glu Glu Arg Asp Lys Cys Pro Gln Trp
175                 180                 185                 190 aaa aca tgg gca gaa tta atc ata ggt caa gca gag ggt cct ggt tct      1106
Lys Thr Trp Ala Glu Leu Ile Ile Gly Gln Ala Glu Gly Pro Gly Ser
                195                 200                 205
```

```
                                                     -continued tat atc atg aac tac ata atg tac atc ttc tgg gcc ttg agt ttt gcc        1154
Tyr Ile Met Asn Tyr Ile Met Tyr Ile Phe Trp Ala Leu Ser Phe Ala
            210                 215                 220 ttt ctt gca gtt tcc ctg gta aag gta ttt gct cca tat gcc tgt ggc        1202
Phe Leu Ala Val Ser Leu Val Lys Val Phe Ala Pro Tyr Ala Cys Gly
225                 230                 235 tct gga att cca gag att aaa act att tta agt gga ttc atc atc aga        1250
Ser Gly Ile Pro Glu Ile Lys Thr Ile Leu Ser Gly Phe Ile Ile Arg
        240                 245                 250 ggt tac ttg gga aaa tgg act tta atg att aaa acc atc aca tta gtc        1298
Gly Tyr Leu Gly Lys Trp Thr Leu Met Ile Lys Thr Ile Thr Leu Val
255                 260                 265                 270 ctg gct gtg gca tca ggt ttg agt tta gga aaa gaa ggt ccc ctg gta        1346
Leu Ala Val Ala Ser Gly Leu Ser Leu Gly Lys Glu Gly Pro Leu Val
                275                 280                 285 cat gtt gcc tgt tgc tgc gga aat atc ttt tcc tac ctc ttt cca aag        1394
His Val Ala Cys Cys Cys Gly Asn Ile Phe Ser Tyr Leu Phe Pro Lys
            290                 295                 300 tat agc aca aac gaa gct aaa aaa agg gag gtg cta tca gct gcc tca        1442
Tyr Ser Thr Asn Glu Ala Lys Lys Arg Glu Val Leu Ser Ala Ala Ser
305                 310                 315 gct gca ggg gtt tct gta gct ttt ggt gca cca att gga gga gtt ctt        1490
Ala Ala Gly Val Ser Val Ala Phe Gly Ala Pro Ile Gly Gly Val Leu
        320                 325                 330 ttt agc ctg gaa gag gtt agc tat tat ttt cct ctc aaa act tta tgg        1538
Phe Ser Leu Glu Glu Val Ser Tyr Tyr Phe Pro Leu Lys Thr Leu Trp
335                 340                 345                 350 aga tca ttt ttt gct gct tta gtg gct gca ttt gtt ttg agg tcc atc        1586
Arg Ser Phe Phe Ala Ala Leu Val Ala Ala Phe Val Leu Arg Ser Ile
                355                 360                 365 aat cca ttt ggt aac agc cgt ctg gtc ctt ttt tat gtg gag tat cat        1634
Asn Pro Phe Gly Asn Ser Arg Leu Val Leu Phe Tyr Val Glu Tyr His
            370                 375                 380 aca cca tgg tac ctt ttt gaa ctg ttt cct ttt att ctt cta ggg gta        1682
Thr Pro Trp Tyr Leu Phe Glu Leu Phe Pro Phe Ile Leu Leu Gly Val
385                 390                 395 ttt gga ggg ctt tgg gga gcc ttt ttc att agg gca aat att gcc tgg        1730
Phe Gly Gly Leu Trp Gly Ala Phe Phe Ile Arg Ala Asn Ile Ala Trp
        400                 405                 410 tgt cgt cga cgc aag tcc acg aaa ttt gga aag tat ccc gtt ctg gaa        1778
Cys Arg Arg Arg Lys Ser Thr Lys Phe Gly Lys Tyr Pro Val Leu Glu
415                 420                 425                 430 gtc att att gtt gca gcc att act gct gtg ata gcc ttc cct aat cca        1826
Val Ile Ile Val Ala Ala Ile Thr Ala Val Ile Ala Phe Pro Asn Pro
                435                 440                 445 tac act agg cta aac acc agt gaa ctg atc aaa gag ctt ttt aca gac        1874
Tyr Thr Arg Leu Asn Thr Ser Glu Leu Ile Lys Glu Leu Phe Thr Asp
            450                 455                 460 tgt ggt ccc ctg gaa tcc tct tct ctt tgt gac tac aga aat gac atg        1922
Cys Gly Pro Leu Glu Ser Ser Ser Leu Cys Asp Tyr Arg Asn Asp Met
465                 470                 475 aat gcc agt aaa att gtc gat gac att cct gat cgt cca gca ggc att        1970
Asn Ala Ser Lys Ile Val Asp Asp Ile Pro Asp Arg Pro Ala Gly Ile
        480                 485                 490 gga gta tat tca gct ata tgg cag tta tgc ctg gca ctc ata ttt aaa        2018
Gly Val Tyr Ser Ala Ile Trp Gln Leu Cys Leu Ala Leu Ile Phe Lys
495                 500                 505                 510 atc ata atg aca gta ttc act ttt ggc atc aag gtt cca tca ggc ttg        2066
Ile Ile Met Thr Val Phe Thr Phe Gly Ile Lys Val Pro Ser Gly Leu
                515                 520                 525
```

```
ttc atc ccc agc atg gcc att gga gcg atc gca gga agg att gtg ggg    2114
Phe Ile Pro Ser Met Ala Ile Gly Ala Ile Ala Gly Arg Ile Val Gly
            530                 535                 540 att gcg gtg gag cag ctt gcc tac tat cac cac gac tgg ttt atc ttt    2162
Ile Ala Val Glu Gln Leu Ala Tyr Tyr His His Asp Trp Phe Ile Phe
        545                 550                 555 aag gag tgg tgt gag gtc ggg gct gat tgc att aca cct ggc ctt tat    2210
Lys Glu Trp Cys Glu Val Gly Ala Asp Cys Ile Thr Pro Gly Leu Tyr
    560                 565                 570 gcc atg gtt ggt gct gct gca tgc tta ggt ggt gtg aca aga atg act    2258
Ala Met Val Gly Ala Ala Cys Leu Gly Gly Val Thr Arg Met Thr
575                 580                 585                 590 gtc tcc ctg gtg gtt att gtt ttt gag ctt act gga ggc ttg gaa tat    2306
Val Ser Leu Val Val Ile Val Phe Glu Leu Thr Gly Gly Leu Glu Tyr
            595                 600                 605 att gtt ccc ctt atg gct gca gtc atg acc agt aaa tgg gtt gga gat    2354
Ile Val Pro Leu Met Ala Ala Val Met Thr Ser Lys Trp Val Gly Asp
        610                 615                 620 gcc ttt ggc agg gaa ggc att tat gaa gca cac atc cga tta aat gga    2402
Ala Phe Gly Arg Glu Gly Ile Tyr Glu Ala His Ile Arg Leu Asn Gly
    625                 630                 635 tac cct ttc ttg gat gca aaa gaa gaa ttc gaa ttc act cat acc acc    2450
Tyr Pro Phe Leu Asp Ala Lys Glu Glu Phe Glu Phe Thr His Thr Thr
640                 645                 650 ctg gct gct gac gtt atg aga cct cga agg aat gat cct ccc tta gct    2498
Leu Ala Ala Asp Val Met Arg Pro Arg Arg Asn Asp Pro Pro Leu Ala
655                 660                 665                 670 gtc ctg aca cag gac aat atg aca gtg gat gat ata gaa aac atg att    2546
Val Leu Thr Gln Asp Asn Met Thr Val Asp Asp Ile Glu Asn Met Ile
            675                 680                 685 aat gaa acc agc tac aat gga ttt cct gtc ata atg tca aaa gaa tct    2594
Asn Glu Thr Ser Tyr Asn Gly Phe Pro Val Ile Met Ser Lys Glu Ser
        690                 695                 700 cag aga tta gtg gga ttt gcc ctc aga aga gac ctg aca att gca ata    2642
Gln Arg Leu Val Gly Phe Ala Leu Arg Arg Asp Leu Thr Ile Ala Ile
    705                 710                 715 gaa agt gcc agg aaa aaa caa gaa ggt atc gtt ggc agt tct cgg gtg    2690
Glu Ser Ala Arg Lys Lys Gln Glu Gly Ile Val Gly Ser Ser Arg Val
720                 725                 730 tgt ttt gca cag cac acc cca tct ctt cca gca gaa agt cct cgg cca    2738
Cys Phe Ala Gln His Thr Pro Ser Leu Pro Ala Glu Ser Pro Arg Pro
735                 740                 745                 750 ttg aag ctt cga agc att ctt gac atg agc cct ttt aca gtg aca gac    2786
Leu Lys Leu Arg Ser Ile Leu Asp Met Ser Pro Phe Thr Val Thr Asp
            755                 760                 765 cac acc cca atg gag att gtg gtg gat att ttc cga aag ctg gga ctg    2834
His Thr Pro Met Glu Ile Val Val Asp Ile Phe Arg Lys Leu Gly Leu
        770                 775                 780 agg cag tgc ctt gta act cac aat ggg cgc ctc ctt ggc att ata aca    2882
Arg Gln Cys Leu Val Thr His Asn Gly Arg Leu Leu Gly Ile Ile Thr
    785                 790                 795 aaa aaa gat atc ctc cgg cat atg gcc cag acg gca aac caa gac ccc    2930
Lys Lys Asp Ile Leu Arg His Met Ala Gln Thr Ala Asn Gln Asp Pro
800                 805                 810 gct tca ata atg ttc aac tga atctcacaga tgaggagaga gaagaaacgg       2981
Ala Ser Ile Met Phe Asn
815                 820 aagaggaagt ttatttgttg aatagcacaa ctctttaacc tgagggagtc atctactttt  3041
```

-continued

```
tttcctcct ttacaaaaaa agaaaggaaa tataaaagcc gggttttttgc aacatggttt      3101 gcaaataatg ctggtggaat ggaggagttg tttggggagg gaaaggagag agaaggaaag      3161
gagtgaggta tttcccgtct aacagaaagc agcgtatcaa ctcctattgt tctgcactgg      3221
atgcattcag ctgaggatgt gcctgatagt gcaggcttgc gcctcaacag agatgacagc      3281
agagtcctcg agcacctggc ctgtttgctc acatgcaaga cacatacagc cctattctag      3341
aggatacttg aatggacctc tataaacgca aggttcttgc cttttttttaa tcaaaactgt      3401 tctgttttaat tcatgaattg tatagttaag cattaccttt ctacattcca gaagagcctt      3461
tatttctctc tctctctctc tctctctctc tctctctact gagctgtaac aaagcctctt      3521
taaatcggtg tatccttttg aagcagtcct ttctcatatt gagatgtact gtgattttac      3581
tgaggtttca tcaacaagaag ggagtgtttc ttgtgccatt aaccatgtag tttgtaccat      3641
cactaaatgc ttggaacagt acacatgcac cacaacaaag gctcatcaaa caggtaaagt      3701
ctcgaaggaa gcgagaacga aatctctcat tgtgtgccgt gtggctcaaa accgaaaaca      3761
atgaagcttg gttttaaagg ataaagttttt cttttttgtt ttcctctcag actttatgga      3821
taatgtgacc gggtcttatg caaatttttct atttctaaaa ctactactat gatatacaag      3881
tgctgttgag cataattaaa taaaatgctg ctgctttgac agtaaagaga aggaagtatt      3941
ctgaaaaaaa ac                                                          3953
```

<210> SEQ ID NO 2
<211> LENGTH: 820
<212> TYPE: PRT
<213> ORGANISM: Homo sapiens

<400> SEQUENCE: 2

```
Met Glu Ser Glu Gln Leu Phe His Arg Gly Tyr Tyr Arg Asn Ser Tyr
  1               5                  10                  15

Asn Ser Ile Thr Ser Ala Ser Ser Asp Glu Glu Leu Leu Asp Gly Ala
             20                  25                  30

Gly Val Ile Met Asp Phe Gln Thr Ser Glu Asp Asp Asn Leu Leu Asp
         35                  40                  45

Gly Asp Thr Ala Val Gly Thr His Tyr Thr Met Thr Asn Gly Gly Ser
     50                  55                  60

Ile Asn Ser Ser Thr His Leu Leu Asp Leu Leu Asp Glu Pro Ile Pro
 65                  70                  75                  80

Gly Val Gly Thr Tyr Asp Asp Phe His Thr Ile Asp Trp Val Arg Glu
                 85                  90                  95

Lys Cys Lys Asp Arg Glu Arg His Arg Arg Ile Asn Ser Lys Lys Lys
            100                 105                 110

Glu Ser Ala Trp Glu Met Thr Lys Ser Leu Tyr Asp Ala Trp Ser Gly
        115                 120                 125

Trp Leu Val Val Thr Leu Thr Gly Leu Ala Ser Gly Ala Leu Ala Gly
    130                 135                 140

Leu Ile Asp Ile Ala Ala Asp Trp Met Thr Asp Leu Lys Glu Gly Ile
145                 150                 155                 160

Cys Leu Ser Ala Leu Trp Tyr Asn His Glu Gln Cys Cys Trp Gly Ser
                165                 170                 175

Asn Glu Thr Thr Phe Glu Glu Arg Asp Lys Cys Pro Gln Trp Lys Thr
            180                 185                 190

Trp Ala Glu Leu Ile Ile Gly Gln Ala Glu Gly Pro Gly Ser Tyr Ile
        195                 200                 205
```

```
Met Asn Tyr Ile Met Tyr Ile Phe Trp Ala Leu Ser Phe Ala Phe Leu
    210                 215                 220

Ala Val Ser Leu Val Lys Val Phe Ala Pro Tyr Ala Cys Gly Ser Gly
225                 230                 235                 240

Ile Pro Glu Ile Lys Thr Ile Leu Ser Gly Phe Ile Ile Arg Gly Tyr
                    245                 250                 255

Leu Gly Lys Trp Thr Leu Met Ile Lys Thr Ile Thr Leu Val Leu Ala
                260                 265                 270

Val Ala Ser Gly Leu Ser Leu Gly Lys Glu Gly Pro Leu Val His Val
            275                 280                 285

Ala Cys Cys Gly Asn Ile Phe Ser Tyr Leu Phe Pro Lys Tyr Ser
        290                 295                 300

Thr Asn Glu Ala Lys Lys Arg Glu Val Leu Ser Ala Ser Ala Ala
305                 310                 315                 320

Gly Val Ser Val Ala Phe Gly Ala Pro Ile Gly Gly Val Leu Phe Ser
                325                 330                 335

Leu Glu Glu Val Ser Tyr Tyr Phe Pro Leu Lys Thr Leu Trp Arg Ser
                340                 345                 350

Phe Phe Ala Ala Leu Val Ala Ala Phe Val Leu Arg Ser Ile Asn Pro
            355                 360                 365

Phe Gly Asn Ser Arg Leu Val Leu Phe Tyr Val Glu Tyr His Thr Pro
    370                 375                 380

Trp Tyr Leu Phe Glu Leu Phe Pro Phe Leu Leu Gly Val Phe Gly
385                 390                 395                 400

Gly Leu Trp Gly Ala Phe Phe Ile Arg Ala Asn Ile Ala Trp Cys Arg
                405                 410                 415

Arg Arg Lys Ser Thr Lys Phe Gly Lys Tyr Pro Val Leu Glu Val Ile
                420                 425                 430

Ile Val Ala Ala Ile Thr Ala Val Ile Ala Phe Pro Asn Pro Tyr Thr
            435                 440                 445

Arg Leu Asn Thr Ser Glu Leu Ile Lys Glu Leu Phe Thr Asp Cys Gly
    450                 455                 460

Pro Leu Glu Ser Ser Ser Leu Cys Asp Tyr Arg Asn Asp Met Asn Ala
465                 470                 475                 480

Ser Lys Ile Val Asp Asp Ile Pro Asp Arg Pro Ala Gly Ile Gly Val
                485                 490                 495

Tyr Ser Ala Ile Trp Gln Leu Cys Leu Ala Leu Ile Phe Lys Ile Ile
                500                 505                 510

Met Thr Val Phe Thr Phe Gly Ile Lys Val Pro Ser Gly Leu Phe Ile
            515                 520                 525

Pro Ser Met Ala Ile Gly Ala Ile Ala Gly Arg Ile Val Gly Ile Ala
            530                 535                 540

Val Glu Gln Leu Ala Tyr Tyr His His Asp Trp Phe Ile Phe Lys Glu
545                 550                 555                 560

Trp Cys Glu Val Gly Ala Asp Cys Ile Thr Pro Gly Leu Tyr Ala Met
                565                 570                 575

Val Gly Ala Ala Ala Cys Leu Gly Gly Val Thr Arg Met Thr Val Ser
                580                 585                 590

Leu Val Val Ile Val Phe Glu Leu Thr Gly Gly Leu Glu Tyr Ile Val
                595                 600                 605

Pro Leu Met Ala Ala Val Met Thr Ser Lys Trp Val Gly Asp Ala Phe
610                 615                 620

Gly Arg Glu Gly Ile Tyr Glu Ala His Ile Arg Leu Asn Gly Tyr Pro
```

```
                625                 630                 635                 640
Phe Leu Asp Ala Lys Glu Glu Phe Glu Phe Thr His Thr Thr Leu Ala
                645                 650                 655

Ala Asp Val Met Arg Pro Arg Arg Asn Asp Pro Pro Leu Ala Val Leu
                660                 665                 670

Thr Gln Asp Asn Met Thr Val Asp Ile Glu Asn Met Ile Asn Glu
                675                 680                 685

Thr Ser Tyr Asn Gly Phe Pro Val Ile Met Ser Lys Glu Ser Gln Arg
                690                 695                 700

Leu Val Gly Phe Ala Leu Arg Arg Asp Leu Thr Ile Ala Ile Glu Ser
705                 710                 715                 720

Ala Arg Lys Lys Gln Glu Gly Ile Val Gly Ser Ser Arg Val Cys Phe
                725                 730                 735

Ala Gln His Thr Pro Ser Leu Pro Ala Glu Ser Pro Arg Pro Leu Lys
                740                 745                 750

Leu Arg Ser Ile Leu Asp Met Ser Pro Phe Thr Val Thr Asp His Thr
                755                 760                 765

Pro Met Glu Ile Val Val Asp Ile Phe Arg Lys Leu Gly Leu Arg Gln
                770                 775                 780

Cys Leu Val Thr His Asn Gly Arg Leu Leu Gly Ile Ile Thr Lys Lys
785                 790                 795                 800

Asp Ile Leu Arg His Met Ala Gln Thr Ala Asn Gln Asp Pro Ala Ser
                805                 810                 815

Ile Met Phe Asn
                820

<210> SEQ ID NO 3
<211> LENGTH: 2758
<212> TYPE: DNA
<213> ORGANISM: Mus musculus
<220> FEATURE:
<221> NAME/KEY: gene
<222> LOCATION: (1)..(2758)
<223> OTHER INFORMATION: Clcn3
<220> FEATURE:
<221> NAME/KEY: CDS
<222> LOCATION: (376)..(2658)

<400> SEQUENCE: 3
gctggagtgg gcggaggcgt gagaaccgcg ttactttcct cccgaggtgg agagagactg     60
ctcctgtagt ccttggagag cgcagtgagc ctccagtcgg ggcagaggcg ggttggtttg    120
agggcccgct ggagccgagg attgaacaac accctgaaac cagcctccgc cggtccgacc    180
tggccgcctt tacgtaacct ctcctgaaag ccggtagcag taaagtccgc cggggtggcc    240
acccggcagc ggtgtcccgg tgaagctccc ggggcggctg gcgcgcgatc gcaagcagat    300
gcggggtcca caggcagcgc agccaccagc cgcccagctt gctatgcctc tgagctgcaa    360
ggaactcatt ataca atg aca aat gga ggc agc att aat agc tct aca cac    411
               Met Thr Asn Gly Gly Ser Ile Asn Ser Ser Thr His
                 1               5                  10 ttg ctg gat ctt tta gat gag cct atc cca ggt gtc ggt acc tac gat    459
Leu Leu Asp Leu Leu Asp Glu Pro Ile Pro Gly Val Gly Thr Tyr Asp
         15                  20                  25 gat ttc cat act att gac tgg gtg cga gag aag tgt aag gac aga gaa    507
Asp Phe His Thr Ile Asp Trp Val Arg Glu Lys Cys Lys Asp Arg Glu
 30                  35                  40 agg cac aga cgg atc aac agt aaa aaa aaa gaa tca gca tgg gaa atg    555
Arg His Arg Arg Ile Asn Ser Lys Lys Lys Glu Ser Ala Trp Glu Met
```

-continued

|  |  |  |  |  |  |  |  |  |  |  |  |  |  |  |  |
|---|---|---|---|---|---|---|---|---|---|---|---|---|---|---|---|
|  | 45 |  |  |  | 50 |  |  |  | 55 |  |  |  | 60 |  |  |

```
aca aaa agt ctg tat gac gcc tgg tca gga tgg ctt gtc gtt aca ctg      603
Thr Lys Ser Leu Tyr Asp Ala Trp Ser Gly Trp Leu Val Val Thr Leu
                    65                  70                  75 acg gga ctg gca tca ggg gca cta gct gga ttg ata gac att gct gct      651
Thr Gly Leu Ala Ser Gly Ala Leu Ala Gly Leu Ile Asp Ile Ala Ala
                80                  85                  90 gac tgg atg act gac ctg aag gag ggc atc tgc ctc agt gca ttg tgg      699
Asp Trp Met Thr Asp Leu Lys Glu Gly Ile Cys Leu Ser Ala Leu Trp
                95                  100                 105 tac aac cat gaa cag tgt tgt tgg ggc tct aat gag aca acg ttt gaa      747
Tyr Asn His Glu Gln Cys Cys Trp Gly Ser Asn Glu Thr Thr Phe Glu
            110                 115                 120 gag agg gat aaa tgt cca cag tgg aaa aca tgg gca gag tta atc att      795
Glu Arg Asp Lys Cys Pro Gln Trp Lys Thr Trp Ala Glu Leu Ile Ile
125                 130                 135                 140 ggc caa gca gag ggc cct gga tct tat atc atg aac tac atc atg tat      843
Gly Gln Ala Glu Gly Pro Gly Ser Tyr Ile Met Asn Tyr Ile Met Tyr
                145                 150                 155 atc ttt tgg gct ttg agt ttt gcc ttt ctt gca gtt tct ttg gtg aaa      891
Ile Phe Trp Ala Leu Ser Phe Ala Phe Leu Ala Val Ser Leu Val Lys
                160                 165                 170 gta ttt gct cca tat gcc tgt ggc tct gga att cca gag att aaa act      939
Val Phe Ala Pro Tyr Ala Cys Gly Ser Gly Ile Pro Glu Ile Lys Thr
                175                 180                 185 att ttg agt gga ttt atc atc aga gga tac ttg gga aaa tgg act tta      987
Ile Leu Ser Gly Phe Ile Ile Arg Gly Tyr Leu Gly Lys Trp Thr Leu
            190                 195                 200 atg att aaa act atc acg tta gtg ctg gct gtg gca tca ggt ttg agt     1035
Met Ile Lys Thr Ile Thr Leu Val Leu Ala Val Ala Ser Gly Leu Ser
205                 210                 215                 220 tta gga aaa gaa ggt ccc ctg gta cat gtt gcc tgc tgc tgt gga aat     1083
Leu Gly Lys Glu Gly Pro Leu Val His Val Ala Cys Cys Cys Gly Asn
                225                 230                 235 atc ttt tcc tac ctc ttt cca aag tat agc acc aat gaa gct aaa aag     1131
Ile Phe Ser Tyr Leu Phe Pro Lys Tyr Ser Thr Asn Glu Ala Lys Lys
                240                 245                 250 agg gag gtg ctg tca gcc gcc tca gct gct ggg gtt tct gtg gct ttt     1179
Arg Glu Val Leu Ser Ala Ala Ser Ala Ala Gly Val Ser Val Ala Phe
                255                 260                 265 ggt gca ccg atc gga gga gtt ctt ttt agc ttg gag gag gtt agc tat     1227
Gly Ala Pro Ile Gly Gly Val Leu Phe Ser Leu Glu Glu Val Ser Tyr
                270                 275                 280 tat ttt cct ctc aaa act tta tgg aga tca ttt ttt gct gct ttg gtg     1275
Tyr Phe Pro Leu Lys Thr Leu Trp Arg Ser Phe Phe Ala Ala Leu Val
285                 290                 295                 300 gca gca ttt gtt ttg aga tcc atc aat cca ttt ggt aac agc cgt ctg     1323
Ala Ala Phe Val Leu Arg Ser Ile Asn Pro Phe Gly Asn Ser Arg Leu
                305                 310                 315 gtc ctc ttt tat gtg gag tat cat aca cca tgg tac ctt ttt gaa ctg     1371
Val Leu Phe Tyr Val Glu Tyr His Thr Pro Trp Tyr Leu Phe Glu Leu
                320                 325                 330 ttt cct ttt att ctc cta ggg gta ttt gga ggg ctt tgg gga gct ttt     1419
Phe Pro Phe Ile Leu Leu Gly Val Phe Gly Gly Leu Trp Gly Ala Phe
                335                 340                 345 ttt att agg gca aat att gcc tgg tgt cgt cga cgc aag tcc acc aaa     1467
Phe Ile Arg Ala Asn Ile Ala Trp Cys Arg Arg Arg Lys Ser Thr Lys
350                 355                 360 ttt gga aag tat cct gtt ctc gaa gtc att att gtt gca gcc att act     1515
```

```
                Phe Gly Lys Tyr Pro Val Leu Glu Val Ile Ile Val Ala Ala Ile Thr
                365                 370                 375                 380 gct gtg ata gcc ttc ccc aac cca tac aca agg ctc aac acc agt gaa           1563
Ala Val Ile Ala Phe Pro Asn Pro Tyr Thr Arg Leu Asn Thr Ser Glu
                        385                 390                 395 ctg att aaa gag ctg ttt aca gat tgt ggg ccg ttg gaa tcc tcc tct           1611
Leu Ile Lys Glu Leu Phe Thr Asp Cys Gly Pro Leu Glu Ser Ser Ser
                400                 405                 410 ctc tgt gac tac aga aat gac atg aat gcc agt aaa att gtt gac gat           1659
Leu Cys Asp Tyr Arg Asn Asp Met Asn Ala Ser Lys Ile Val Asp Asp
            415                 420                 425 att cct gac cgt cca gca ggc gtt gga gta tat tca gct atc tgg cag           1707
Ile Pro Asp Arg Pro Ala Gly Val Gly Val Tyr Ser Ala Ile Trp Gln
        430                 435                 440 ttg tgc cta gcg ctc ata ttt aaa ata ata atg aca gta ttc act ttt           1755
Leu Cys Leu Ala Leu Ile Phe Lys Ile Ile Met Thr Val Phe Thr Phe
445                 450                 455                 460 ggt atc aag gtc ccg tca ggc ttg ttt atc ccc agc atg gcc att gga           1803
Gly Ile Lys Val Pro Ser Gly Leu Phe Ile Pro Ser Met Ala Ile Gly
                        465                 470                 475 gcc att gca ggg aga att gtg ggg atc gct gtg gag cag ctt gcc tac           1851
Ala Ile Ala Gly Arg Ile Val Gly Ile Ala Val Glu Gln Leu Ala Tyr
                480                 485                 490 tat cac cac gac tgg ttt atc ttc aag gag tgg tgt gag gtt ggg gct           1899
Tyr His His Asp Trp Phe Ile Phe Lys Glu Trp Cys Glu Val Gly Ala
            495                 500                 505 gac tgc atc act ccc ggg ctg tat gcc atg gtt ggg gct gct gcg tgc           1947
Asp Cys Ile Thr Pro Gly Leu Tyr Ala Met Val Gly Ala Ala Ala Cys
        510                 515                 520 tta ggt ggt gtg aca aga atg act gtg tct ctg gtg gtt att gtt ttt           1995
Leu Gly Gly Val Thr Arg Met Thr Val Ser Leu Val Val Ile Val Phe
525                 530                 535                 540 gaa ctt act gga ggc ttg gaa tat att gtt cct ctt atg gct gca gta           2043
Glu Leu Thr Gly Gly Leu Glu Tyr Ile Val Pro Leu Met Ala Ala Val
                        545                 550                 555 atg acc agt aaa tgg gtt ggt gat gcc ttt ggt agg gaa ggt att tat           2091
Met Thr Ser Lys Trp Val Gly Asp Ala Phe Gly Arg Glu Gly Ile Tyr
                560                 565                 570 gaa gca cac atc cga cta aat ggg tac cct ttc ttg gat gca aaa gaa           2139
Glu Ala His Ile Arg Leu Asn Gly Tyr Pro Phe Leu Asp Ala Lys Glu
            575                 580                 585 gaa ttc act cat aca acc ctg gct gct gat gtt atg aga cct cga aga           2187
Glu Phe Thr His Thr Thr Leu Ala Ala Asp Val Met Arg Pro Arg Arg
        590                 595                 600 agt gac cct ccc tta gct gtt ttg aca cag gac aat atg aca gta gat           2235
Ser Asp Pro Pro Leu Ala Val Leu Thr Gln Asp Asn Met Thr Val Asp
605                 610                 615                 620 gac ata gaa aac atg att aat gaa acc agc tat aat ggc ttt cct gtt           2283
Asp Ile Glu Asn Met Ile Asn Glu Thr Ser Tyr Asn Gly Phe Pro Val
                        625                 630                 635 ata atg tca aaa gaa tct cag aga tta gtg gga ttt gcc ctc aga aga           2331
Ile Met Ser Lys Glu Ser Gln Arg Leu Val Gly Phe Ala Leu Arg Arg
                640                 645                 650 gac ctg act att gca ata gaa agt gcc aga aaa aaa caa gaa ggg att           2379
Asp Leu Thr Ile Ala Ile Glu Ser Ala Arg Lys Lys Gln Glu Gly Ile
            655                 660                 665 gtt ggc agt tct cgg gtg tgt ttt gca cag cat act cca tct ctt cca           2427
Val Gly Ser Ser Arg Val Cys Phe Ala Gln His Thr Pro Ser Leu Pro
        670                 675                 680
```

-continued

```
gca gaa agt cca cgg cca tta aaa ctg aga agc atc ctt gac atg agc    2475
Ala Glu Ser Pro Arg Pro Leu Lys Leu Arg Ser Ile Leu Asp Met Ser
685                 690                 695                 700 cct ttt aca gtg aca gac cac acc cca atg gag att gtg gta gac atc    2523
Pro Phe Thr Val Thr Asp His Thr Pro Met Glu Ile Val Val Asp Ile
            705                 710                 715 ttt cga aag ctt ggt ctg agg cag tgc ctt gta act cac aac gga cgc    2571
Phe Arg Lys Leu Gly Leu Arg Gln Cys Leu Val Thr His Asn Gly Arg
        720                 725                 730 ctc ctt ggc att ata aca aaa aaa gat atc ctc cgt cat atg gcc cag    2619
Leu Leu Gly Ile Ile Thr Lys Lys Asp Ile Leu Arg His Met Ala Gln
    735                 740                 745 acg gca aac caa gac ccc gct tca ata atg ttc aac tga gtcctgtaga     2668
Thr Ala Asn Gln Asp Pro Ala Ser Ile Met Phe Asn
750                 755                 760 tgaggacaga gaggagacag aagaggaagt tcgtttgttg aatagcacaa ttctttaatc  2728
tgcgggactc gtccactttt ttcttctttc                                   2758

<210> SEQ ID NO 4
<211> LENGTH: 760
<212> TYPE: PRT
<213> ORGANISM: Mus musculus

<400> SEQUENCE: 4

Met Thr Asn Gly Gly Ser Ile Asn Ser Ser Thr His Leu Leu Asp Leu
1               5                   10                  15

Leu Asp Glu Pro Ile Pro Gly Val Gly Thr Tyr Asp Asp Phe His Thr
            20                  25                  30

Ile Asp Trp Val Arg Glu Lys Cys Lys Asp Arg Glu Arg His Arg Arg
        35                  40                  45

Ile Asn Ser Lys Lys Lys Glu Ser Ala Trp Glu Met Thr Lys Ser Leu
    50                  55                  60

Tyr Asp Ala Trp Ser Gly Trp Leu Val Val Thr Leu Thr Gly Leu Ala
65                  70                  75                  80

Ser Gly Ala Leu Ala Gly Leu Ile Asp Ile Ala Ala Asp Trp Met Thr
                85                  90                  95

Asp Leu Lys Glu Gly Ile Cys Leu Ser Ala Leu Trp Tyr Asn His Glu
            100                 105                 110

Gln Cys Cys Trp Gly Ser Asn Glu Thr Thr Phe Glu Glu Arg Asp Lys
        115                 120                 125

Cys Pro Gln Trp Lys Thr Trp Ala Glu Leu Ile Ile Gly Gln Ala Glu
    130                 135                 140

Gly Pro Gly Ser Tyr Ile Met Asn Tyr Ile Met Tyr Ile Phe Trp Ala
145                 150                 155                 160

Leu Ser Phe Ala Phe Leu Ala Val Ser Leu Val Lys Val Phe Ala Pro
                165                 170                 175

Tyr Ala Cys Gly Ser Gly Ile Pro Glu Ile Lys Thr Ile Leu Ser Gly
            180                 185                 190

Phe Ile Ile Arg Gly Tyr Leu Gly Lys Trp Thr Leu Met Ile Lys Thr
        195                 200                 205

Ile Thr Leu Val Leu Ala Val Ala Ser Gly Leu Ser Leu Gly Lys Glu
    210                 215                 220

Gly Pro Leu Val His Val Ala Cys Cys Cys Gly Asn Ile Phe Ser Tyr
225                 230                 235                 240

Leu Phe Pro Lys Tyr Ser Thr Asn Glu Ala Lys Lys Arg Glu Val Leu
                245                 250                 255
```

-continued

Ser Ala Ala Ser Ala Ala Gly Val Ser Val Ala Phe Gly Ala Pro Ile
            260                 265                 270

Gly Gly Val Leu Phe Ser Leu Glu Glu Val Ser Tyr Tyr Phe Pro Leu
            275                 280                 285

Lys Thr Leu Trp Arg Ser Phe Phe Ala Ala Leu Val Ala Ala Phe Val
            290                 295                 300

Leu Arg Ser Ile Asn Pro Phe Gly Asn Ser Arg Leu Val Leu Phe Tyr
305                 310                 315                 320

Val Glu Tyr His Thr Pro Trp Tyr Leu Phe Glu Leu Phe Pro Phe Ile
                325                 330                 335

Leu Leu Gly Val Phe Gly Gly Leu Trp Gly Ala Phe Phe Ile Arg Ala
            340                 345                 350

Asn Ile Ala Trp Cys Arg Arg Lys Ser Thr Lys Phe Gly Lys Tyr
            355                 360                 365

Pro Val Leu Glu Val Ile Ile Val Ala Ala Ile Thr Ala Val Ile Ala
            370                 375                 380

Phe Pro Asn Pro Tyr Thr Arg Leu Asn Thr Ser Glu Leu Ile Lys Glu
385                 390                 395                 400

Leu Phe Thr Asp Cys Gly Pro Leu Glu Ser Ser Leu Cys Asp Tyr
                405                 410                 415

Arg Asn Asp Met Asn Ala Ser Lys Ile Val Asp Asp Ile Pro Asp Arg
            420                 425                 430

Pro Ala Gly Val Gly Val Tyr Ser Ala Ile Trp Gln Leu Cys Leu Ala
            435                 440                 445

Leu Ile Phe Lys Ile Ile Met Thr Val Phe Thr Phe Gly Ile Lys Val
450                 455                 460

Pro Ser Gly Leu Phe Ile Pro Ser Met Ala Ile Gly Ala Ile Ala Gly
465                 470                 475                 480

Arg Ile Val Gly Ile Ala Val Glu Gln Leu Ala Tyr Tyr His His Asp
                485                 490                 495

Trp Phe Ile Phe Lys Glu Trp Cys Glu Val Gly Ala Asp Cys Ile Thr
                500                 505                 510

Pro Gly Leu Tyr Ala Met Val Gly Ala Ala Ala Cys Leu Gly Gly Val
            515                 520                 525

Thr Arg Met Thr Val Ser Leu Val Val Ile Val Phe Glu Leu Thr Gly
530                 535                 540

Gly Leu Glu Tyr Ile Val Pro Leu Met Ala Ala Val Met Thr Ser Lys
545                 550                 555                 560

Trp Val Gly Asp Ala Phe Gly Arg Glu Gly Ile Tyr Glu Ala His Ile
                565                 570                 575

Arg Leu Asn Gly Tyr Pro Phe Leu Asp Ala Lys Glu Glu Phe Thr His
            580                 585                 590

Thr Thr Leu Ala Ala Asp Val Met Arg Pro Arg Arg Ser Asp Pro Pro
            595                 600                 605

Leu Ala Val Leu Thr Gln Asp Asn Met Thr Val Asp Asp Ile Glu Asn
            610                 615                 620

Met Ile Asn Glu Thr Ser Tyr Asn Gly Phe Pro Val Ile Met Ser Lys
625                 630                 635                 640

Glu Ser Gln Arg Leu Val Gly Phe Ala Leu Arg Arg Asp Leu Thr Ile
                645                 650                 655

Ala Ile Glu Ser Ala Arg Lys Lys Gln Glu Gly Ile Val Gly Ser Ser
            660                 665                 670

```
Arg Val Cys Phe Ala Gln His Thr Pro Ser Leu Pro Ala Glu Ser Pro
            675                 680                 685

Arg Pro Leu Lys Leu Arg Ser Ile Leu Asp Met Ser Pro Phe Thr Val
            690                 695                 700

Thr Asp His Thr Pro Met Glu Ile Val Val Asp Ile Phe Arg Lys Leu
705                 710                 715                 720

Gly Leu Arg Gln Cys Leu Val Thr His Asn Gly Arg Leu Leu Gly Ile
                725                 730                 735

Ile Thr Lys Lys Asp Ile Leu Arg His Met Ala Gln Thr Ala Asn Gln
                740                 745                 750

Asp Pro Ala Ser Ile Met Phe Asn
            755                 760

<210> SEQ ID NO 5
<211> LENGTH: 2588
<212> TYPE: DNA
<213> ORGANISM: Homo sapiens
<220> FEATURE:
<221> NAME/KEY: gene
<222> LOCATION: (1)..(2588)
<223> OTHER INFORMATION: CLCN4
<220> FEATURE:
<221> NAME/KEY: CDS
<222> LOCATION: (51)..(2051)
<223> OTHER INFORMATION: ClC-4

<400> SEQUENCE: 5
tacttcttcc aggcaccttg gctggggtca tcgatctcgc cgtggactgg atg acg          56
                                                        Met Thr
                                                        1 gac ctg aag gag ggg gtc tgc ctg tct gcc ttc tgg tat agc cat gag         104
Asp Leu Lys Glu Gly Val Cys Leu Ser Ala Phe Trp Tyr Ser His Glu
        5                   10                  15 cag tgt tgc tgg act tct aac gag acc act ttt gag gac aga gac aag         152
Gln Cys Cys Trp Thr Ser Asn Glu Thr Thr Phe Glu Asp Arg Asp Lys
    20                  25                  30 tgt ccc ctg tgg cag aaa tgg tcg gag ctg ctg gtg aat cag tca gag         200
Cys Pro Leu Trp Gln Lys Trp Ser Glu Leu Leu Val Asn Gln Ser Glu
35                  40                  45                  50 ggt gcc agt gct tac att ctg aat tac tta atg tac atc cta tgg gcg         248
Gly Ala Ser Ala Tyr Ile Leu Asn Tyr Leu Met Tyr Ile Leu Trp Ala
                55                  60                  65 ctg ctg ttt gca ttt ttg gct gtc tcc ctg gtg cgt gta ttt gca cca         296
Leu Leu Phe Ala Phe Leu Ala Val Ser Leu Val Arg Val Phe Ala Pro
            70                  75                  80 tat gcc tgt ggc tct ggc ata cca gag ata aag acc att ttg agc ggc         344
Tyr Ala Cys Gly Ser Gly Ile Pro Glu Ile Lys Thr Ile Leu Ser Gly
        85                  90                  95 ttt atc atc agg ggc tac ttg ggg aag tgg acc ctg cta atc aag aca         392
Phe Ile Ile Arg Gly Tyr Leu Gly Lys Trp Thr Leu Leu Ile Lys Thr
    100                 105                 110 gtc acg ctg gtg ctg gta gtg tcc tcc ggt ctg agc ctt ggg aag gaa         440
Val Thr Leu Val Leu Val Val Ser Ser Gly Leu Ser Leu Gly Lys Glu
115                 120                 125                 130 ggg ccg cta gtg cac gtg gct tgt tgc tgt ggc aac ttc ttc agc agc         488
Gly Pro Leu Val His Val Ala Cys Cys Cys Gly Asn Phe Phe Ser Ser
                135                 140                 145 ctt ttc tcc aag tac agc aag aat gag ggc aag agg cgg gag gtg ctt         536
Leu Phe Ser Lys Tyr Ser Lys Asn Glu Gly Lys Arg Arg Glu Val Leu
            150                 155                 160 tca gct gca gcg gct gct gga gtc tct gtt gcc ttt ggt gca cca att         584
```

```
                Ser Ala Ala Ala Ala Gly Val Ser Val Ala Phe Gly Ala Pro Ile
                    165                 170                 175 gga ggc gtg ctt ttc agt cta gaa gag gtc agt tac tac ttt ccc ctg          632
Gly Gly Val Leu Phe Ser Leu Glu Glu Val Ser Tyr Tyr Phe Pro Leu
180                 185                 190 aag acc ttg tgg agg tca ttt ttc gca gcc ctg gtg gcg gcc ttt acg          680
Lys Thr Leu Trp Arg Ser Phe Phe Ala Ala Leu Val Ala Ala Phe Thr
195                 200                 205                 210 ctg aga tcc atc aat ccc ttt ggg aat agc cgt ctc gtt ctc ttt tat          728
Leu Arg Ser Ile Asn Pro Phe Gly Asn Ser Arg Leu Val Leu Phe Tyr
                215                 220                 225 gtg gaa tac cac acg ccc tgg tac atg gct gaa ctc ttc ccc ttc atc          776
Val Glu Tyr His Thr Pro Trp Tyr Met Ala Glu Leu Phe Pro Phe Ile
            230                 235                 240 ctg ctt ggg gtc ttc ggg ggc ttg tgg gga acc ctc ttc atc cgc tgc          824
Leu Leu Gly Val Phe Gly Gly Leu Trp Gly Thr Leu Phe Ile Arg Cys
        245                 250                 255 aac atc gcc tgg tgc agg agg cgc aag acc acc agg ctg ggg aag tac          872
Asn Ile Ala Trp Cys Arg Arg Arg Lys Thr Thr Arg Leu Gly Lys Tyr
    260                 265                 270 ccg gtg ctg gag gtc att gtg gtg act gcc atc act gcc atc att gcc          920
Pro Val Leu Glu Val Ile Val Val Thr Ala Ile Thr Ala Ile Ile Ala
275                 280                 285                 290 tac ccc aat ccc tac aca cgc cag agc acc agc gag ctc att tct gag          968
Tyr Pro Asn Pro Tyr Thr Arg Gln Ser Thr Ser Glu Leu Ile Ser Glu
                295                 300                 305 ctg ttc aat gac tgt gga gcc ctt gag tct tcc cag ctc tgt gac tac         1016
Leu Phe Asn Asp Cys Gly Ala Leu Glu Ser Ser Gln Leu Cys Asp Tyr
            310                 315                 320 atc aat gac ccc aac atg act cgg cct gtg gat gac att cca gac cgg         1064
Ile Asn Asp Pro Asn Met Thr Arg Pro Val Asp Asp Ile Pro Asp Arg
        325                 330                 335 ccg gct ggt gtc ggt gtt tac acg gcc atg tgg cag ctg gcc ctg gca         1112
Pro Ala Gly Val Gly Val Tyr Thr Ala Met Trp Gln Leu Ala Leu Ala
    340                 345                 350 ctg atc ttc aaa atc gtc gtt acc ata ttt acc ttt ggc atg aag atc         1160
Leu Ile Phe Lys Ile Val Val Thr Ile Phe Thr Phe Gly Met Lys Ile
355                 360                 365                 370 ccg tcg ggc ctc ttc atc ccc agc atg gct gtg ggc gcg ata gcg ggc         1208
Pro Ser Gly Leu Phe Ile Pro Ser Met Ala Val Gly Ala Ile Ala Gly
                375                 380                 385 agg atg gtg gga att ggc gtg gag cag ctg gcc tac cat cac cat gac         1256
Arg Met Val Gly Ile Gly Val Glu Gln Leu Ala Tyr His His His Asp
            390                 395                 400 tgg atc atc ttc agg aac tgg tgc aga ccc ggt gca gac tgt gtc acg         1304
Trp Ile Ile Phe Arg Asn Trp Cys Arg Pro Gly Ala Asp Cys Val Thr
        405                 410                 415 cca ggg ctg tac gca atg gtg gga gct gcg gcc tgc ctc ggt gga gtt         1352
Pro Gly Leu Tyr Ala Met Val Gly Ala Ala Ala Cys Leu Gly Gly Val
    420                 425                 430 acc agg atg acg gtg tca ttg gtg gtc atc atg ttt gaa tta acc ggg         1400
Thr Arg Met Thr Val Ser Leu Val Val Ile Met Phe Glu Leu Thr Gly
435                 440                 445                 450 ggt ctg gag tac atc gtg ccc ctg atg gcg gcg gct gtg acc agc aag         1448
Gly Leu Glu Tyr Ile Val Pro Leu Met Ala Ala Ala Val Thr Ser Lys
                455                 460                 465 tgg gta gct gat gca ttt ggg aaa gaa ggc atc tac gag gcc cac atc         1496
Trp Val Ala Asp Ala Phe Gly Lys Glu Gly Ile Tyr Glu Ala His Ile
            470                 475                 480
```

-continued

```
cac tta aat ggg tac cct ttc ctt gac gtg aag gac gag ttt act cac    1544
His Leu Asn Gly Tyr Pro Phe Leu Asp Val Lys Asp Glu Phe Thr His
            485                 490                 495 cgc aca ctg gcc acc gac gtc atg cgg ccc cgg cgg gga gag ccg cca    1592
Arg Thr Leu Ala Thr Asp Val Met Arg Pro Arg Arg Gly Glu Pro Pro
500                 505                 510 ctg tcg gtg ctc acc cag gac agc atg act gtc gag gac gtg gag acg    1640
Leu Ser Val Leu Thr Gln Asp Ser Met Thr Val Glu Asp Val Glu Thr
515                 520                 525                 530 ctc atc aag gag acc gac tac aac ggc ttc ccc gtg gtg gtc tcc aga    1688
Leu Ile Lys Glu Thr Asp Tyr Asn Gly Phe Pro Val Val Val Ser Arg
                535                 540                 545 gac tcc gag cgc ctc att gga ttt gcc cag agg agg gaa ctg att ctc    1736
Asp Ser Glu Arg Leu Ile Gly Phe Ala Gln Arg Arg Glu Leu Ile Leu
            550                 555                 560 gca ata aag aac gcc aga cag agg cag gag ggc att gtg agc aat tcc    1784
Ala Ile Lys Asn Ala Arg Gln Arg Gln Glu Gly Ile Val Ser Asn Ser
        565                 570                 575 atc atg tac ttc acg gag gaa ccc ccc gag ctg ccg gcc aac agc cca    1832
Ile Met Tyr Phe Thr Glu Glu Pro Pro Glu Leu Pro Ala Asn Ser Pro
580                 585                 590 cat ccc ctg aag ctg cgg cgc atc ctg aac ctc agc ccg ttt aca gtg    1880
His Pro Leu Lys Leu Arg Arg Ile Leu Asn Leu Ser Pro Phe Thr Val
595                 600                 605                 610 aca gac cac act ccg atg gaa acg gtg gtg gat atc ttc cgg aaa ctg    1928
Thr Asp His Thr Pro Met Glu Thr Val Val Asp Ile Phe Arg Lys Leu
                615                 620                 625 ggg ctt cgg cag tgc ctg gtg acg cgg agc ggg aga ctt ctt ggc atc    1976
Gly Leu Arg Gln Cys Leu Val Thr Arg Ser Gly Arg Leu Leu Gly Ile
            630                 635                 640 atc aca aaa aag gat gtt ctg aga cat atg gcc cag atg gca aac cag    2024
Ile Thr Lys Lys Asp Val Leu Arg His Met Ala Gln Met Ala Asn Gln
        645                 650                 655 gac ccc gaa tcc atc atg ttt aat tag caacaaggtg gcaattattt           2071
Asp Pro Glu Ser Ile Met Phe Asn
660                 665 tcagaaaaac actgactgtg tcatttaaaa agaaataaat gatatgttat tatcccaatg   2131
aaagatcatg cattggggac agcagaaaca aaagcttttt tggaaaggcg gggaagaagg   2191
atgaaacctt taaaaacaaa aacaaaaaca tcaatgagta ggcatttat agctttaacc    2251 ccgtatgagt ttcaagctgt gtttcctaat gagtttgcta ctgctgtggg ggcatgtggg   2311
tgggtaaatg atgtaaatga tgtgatctgt acaagtatgt ggagcatgaa tgctgactca   2371
agaaactttt actccttctg ctcaaggctg atgtttgtaa cttatgaaca cacgtgaagt   2431
gttgagtcca aaagacaaag gggcatcggc atgtcagcgt ccttatttat tggttcttga   2491
agttttgctg ctatgttact gaatcatact aaagacattt gcgcttactt tgttgaaaaa   2551 gaaaagaaa ttaaatttga acacagtgaa agctgca                             2588

<210> SEQ ID NO 6
<211> LENGTH: 666
<212> TYPE: PRT
<213> ORGANISM: Homo sapiens

<400> SEQUENCE: 6

Met Thr Asp Leu Lys Glu Gly Val Cys Leu Ser Ala Phe Trp Tyr Ser
1               5                   10                  15

His Glu Gln Cys Cys Trp Thr Ser Asn Glu Thr Thr Phe Glu Asp Arg
            20                  25                  30
```

-continued

```
Asp Lys Cys Pro Leu Trp Gln Lys Trp Ser Glu Leu Leu Val Asn Gln
         35                  40                  45

Ser Glu Gly Ala Ser Ala Tyr Ile Leu Asn Tyr Leu Met Tyr Ile Leu
     50                  55                  60

Trp Ala Leu Leu Phe Ala Phe Leu Ala Val Ser Leu Val Arg Val Phe
 65                  70                  75                  80

Ala Pro Tyr Ala Cys Gly Ser Gly Ile Pro Glu Ile Lys Thr Ile Leu
                 85                  90                  95

Ser Gly Phe Ile Ile Arg Gly Tyr Leu Gly Lys Trp Thr Leu Leu Ile
            100                 105                 110

Lys Thr Val Thr Leu Val Leu Val Ser Ser Gly Leu Ser Leu Gly
        115                 120                 125

Lys Glu Gly Pro Leu Val His Val Ala Cys Cys Cys Gly Asn Phe Phe
    130                 135                 140

Ser Ser Leu Phe Ser Lys Tyr Ser Lys Asn Glu Gly Lys Arg Arg Glu
145                 150                 155                 160

Val Leu Ser Ala Ala Ala Ala Gly Val Ser Val Ala Phe Gly Ala
                165                 170                 175

Pro Ile Gly Gly Val Leu Phe Ser Leu Glu Glu Val Ser Tyr Tyr Phe
            180                 185                 190

Pro Leu Lys Thr Leu Trp Arg Ser Phe Phe Ala Ala Leu Val Ala Ala
        195                 200                 205

Phe Thr Leu Arg Ser Ile Asn Pro Phe Gly Asn Ser Arg Leu Val Leu
    210                 215                 220

Phe Tyr Val Glu Tyr His Thr Pro Trp Tyr Met Ala Glu Leu Phe Pro
225                 230                 235                 240

Phe Ile Leu Leu Gly Val Phe Gly Gly Leu Trp Gly Thr Leu Phe Ile
                245                 250                 255

Arg Cys Asn Ile Ala Trp Cys Arg Arg Arg Lys Thr Thr Arg Leu Gly
            260                 265                 270

Lys Tyr Pro Val Leu Glu Val Ile Val Val Thr Ala Ile Thr Ala Ile
        275                 280                 285

Ile Ala Tyr Pro Asn Pro Tyr Thr Arg Gln Ser Thr Ser Glu Leu Ile
    290                 295                 300

Ser Glu Leu Phe Asn Asp Cys Gly Ala Leu Glu Ser Ser Gln Leu Cys
305                 310                 315                 320

Asp Tyr Ile Asn Asp Pro Asn Met Thr Arg Pro Val Asp Asp Ile Pro
                325                 330                 335

Asp Arg Pro Ala Gly Val Gly Val Tyr Thr Ala Met Trp Gln Leu Ala
            340                 345                 350

Leu Ala Leu Ile Phe Lys Ile Val Val Thr Ile Phe Thr Phe Gly Met
        355                 360                 365

Lys Ile Pro Ser Gly Leu Phe Ile Pro Ser Met Ala Val Gly Ala Ile
    370                 375                 380

Ala Gly Arg Met Val Gly Ile Gly Val Glu Gln Leu Ala Tyr His His
385                 390                 395                 400

His Asp Trp Ile Ile Phe Arg Asn Trp Cys Arg Pro Gly Ala Asp Cys
                405                 410                 415

Val Thr Pro Gly Leu Tyr Ala Met Val Gly Ala Ala Ala Cys Leu Gly
            420                 425                 430

Gly Val Thr Arg Met Thr Val Ser Leu Val Val Ile Met Phe Glu Leu
        435                 440                 445
```

```
Thr Gly Gly Leu Glu Tyr Ile Val Pro Leu Met Ala Ala Val Thr
    450                 455                 460

Ser Lys Trp Val Ala Asp Ala Phe Gly Lys Glu Gly Ile Tyr Glu Ala
465                 470                 475                 480

His Ile His Leu Asn Gly Tyr Pro Phe Leu Asp Val Lys Asp Glu Phe
                485                 490                 495

Thr His Arg Thr Leu Ala Thr Asp Val Met Arg Pro Arg Gly Glu
            500                 505                 510

Pro Pro Leu Ser Val Leu Thr Gln Asp Ser Met Thr Val Glu Asp Val
            515                 520                 525

Glu Thr Leu Ile Lys Glu Thr Asp Tyr Asn Gly Phe Pro Val Val Val
    530                 535                 540

Ser Arg Asp Ser Glu Arg Leu Ile Gly Phe Ala Gln Arg Arg Glu Leu
545                 550                 555                 560

Ile Leu Ala Ile Lys Asn Ala Arg Gln Arg Gln Glu Gly Ile Val Ser
                565                 570                 575

Asn Ser Ile Met Tyr Phe Thr Glu Glu Pro Glu Leu Pro Ala Asn
            580                 585                 590

Ser Pro His Pro Leu Lys Leu Arg Arg Ile Leu Asn Leu Ser Pro Phe
            595                 600                 605

Thr Val Thr Asp His Thr Pro Met Glu Thr Val Val Asp Ile Phe Arg
    610                 615                 620

Lys Leu Gly Leu Arg Gln Cys Leu Val Thr Arg Ser Gly Arg Leu Leu
625                 630                 635                 640

Gly Ile Ile Thr Lys Lys Asp Val Leu Arg His Met Ala Gln Met Ala
                645                 650                 655

Asn Gln Asp Pro Glu Ser Ile Met Phe Asn
            660                 665
```

<210> SEQ ID NO 7
<211> LENGTH: 2739
<212> TYPE: DNA
<213> ORGANISM: Mus musculus
<220> FEATURE:
<221> NAME/KEY: gene
<222> LOCATION: (1)..(2739)
<223> OTHER INFORMATION: Clcn4-2
<220> FEATURE:
<221> NAME/KEY: CDS
<222> LOCATION: (378)..(2621)
<223> OTHER INFORMATION: Clc 4-2

<400> SEQUENCE: 7

```
taaatgtgac ttaataaatg gtgcaaaatt aaattttatt gcttgaggac agacgggcat      60
aaaggaaggg aaaagacatt taatgtaaag gcaacaacaa caacaacaaa actgtcccgg     120
atgaggaagg catttaagtc atttcagcca agctgaacac ggagacaggg ggatgacgct     180
gaacacttgc cccgccccgc ctgcctgcct gtcacccgcc tcgcgatgac gtcacacgac     240
ctgccgcaga cagccgcgct gaagagagga ggatgatcta ggacgctgtc cgggtggacg     300
gccacgccgc aagacgcggc cctgcaggag tgactagcac ggtcagggcg ggagccacga     360
gcgcctctgg gaacctc atg gac ttc ctc gag gag ccc ttc cct gac gtg      410
                   Met Asp Phe Leu Glu Glu Pro Phe Pro Asp Val
                    1               5                  10 ggg acc tac gag gac ttc cac acc ata gac tgg ctg agg gaa aag tcc      458
Gly Thr Tyr Glu Asp Phe His Thr Ile Asp Trp Leu Arg Glu Lys Ser
         15                  20                  25 cgg gat acc gac aga cat agg aag atc acc agc aaa agt aag gag tct      506
Arg Asp Thr Asp Arg His Arg Lys Ile Thr Ser Lys Ser Lys Glu Ser
```

```
Arg Asp Thr Asp Arg His Arg Lys Ile Thr Ser Lys Ser Lys Glu Ser
         30                  35                  40 att tgg gag ttc atc aag agc ctg ctg gac gcg tgg tcg gga tgg gtg      554
Ile Trp Glu Phe Ile Lys Ser Leu Leu Asp Ala Trp Ser Gly Trp Val
         45                  50                  55 gtg atg cta ctc att ggg ctg ctg gca ggt acc tta gct gga gtc atc      602
Val Met Leu Leu Ile Gly Leu Leu Ala Gly Thr Leu Ala Gly Val Ile
 60                  65                  70                  75 gat ctc gct gtg gat tgg atg acg gac ctc aag gag ggg gtc tgt ctg      650
Asp Leu Ala Val Asp Trp Met Thr Asp Leu Lys Glu Gly Val Cys Leu
                 80                  85                  90 tcc gca ttc tgg tac agc cat gaa cag tgc tgt tgg acc tcc aac gag      698
Ser Ala Phe Trp Tyr Ser His Glu Gln Cys Cys Trp Thr Ser Asn Glu
             95                 100                 105 acc act ttt gag gac agg gac aag tgt ccc ctg tgg cag aag tgg tca      746
Thr Thr Phe Glu Asp Arg Asp Lys Cys Pro Leu Trp Gln Lys Trp Ser
         110                 115                 120 gag ctt ctt ctg agc cag tca gag ggc gcc agc gct tac att ctg aat      794
Glu Leu Leu Leu Ser Gln Ser Glu Gly Ala Ser Ala Tyr Ile Leu Asn
     125                 130                 135 tac tta atg tac att cta tgg gcg ttg ctg ttt gca ttt ctg gct gtc      842
Tyr Leu Met Tyr Ile Leu Trp Ala Leu Leu Phe Ala Phe Leu Ala Val
140                 145                 150                 155 tcc ctg gta cgt gtg ttc gca ccg tat gcc tgt ggc tct ggc ata ccc      890
Ser Leu Val Arg Val Phe Ala Pro Tyr Ala Cys Gly Ser Gly Ile Pro
                 160                 165                 170 gag ata aag act att ttg agt ggc ttt atc atc agg ggc tac ttg ggg      938
Glu Ile Lys Thr Ile Leu Ser Gly Phe Ile Ile Arg Gly Tyr Leu Gly
             175                 180                 185 aaa tgg act ctt cta atc aag act gtc acc ctc gtg ctc gtc gta tcc      986
Lys Trp Thr Leu Leu Ile Lys Thr Val Thr Leu Val Leu Val Val Ser
         190                 195                 200 tct ggc ctg agc ctt ggc aaa gag ggc cca ctg gtg cat gtg gca tgt     1034
Ser Gly Leu Ser Leu Gly Lys Glu Gly Pro Leu Val His Val Ala Cys
     205                 210                 215 tgc tgt ggc aac ttc ttc agc agc ctt ttc tcc aag tat agc aag aat     1082
Cys Cys Gly Asn Phe Phe Ser Ser Leu Phe Ser Lys Tyr Ser Lys Asn
220                 225                 230                 235 gaa ggc aag agg cgt gag gtg ctt tca gct gca gct gct ggt gtc         1130
Glu Gly Lys Arg Arg Glu Val Leu Ser Ala Ala Ala Ala Gly Val
                 240                 245                 250 tct gtg gcc ttt ggt gct ccg ata gga ggt gtg ctc ttc agt cta gag     1178
Ser Val Ala Phe Gly Ala Pro Ile Gly Gly Val Leu Phe Ser Leu Glu
             255                 260                 265 gag gtc agt tac tac ttt ccc ttg aaa acc ttg tgg agg tca ttc ttt     1226
Glu Val Ser Tyr Tyr Phe Pro Leu Lys Thr Leu Trp Arg Ser Phe Phe
         270                 275                 280 gca gcc ctg gtg gct gcc ttc aca ctg cgc tcc atc aac ccc ttt gga     1274
Ala Ala Leu Val Ala Ala Phe Thr Leu Arg Ser Ile Asn Pro Phe Gly
     285                 290                 295 aat agc cgc ctg gtt ctc ttt tac gtg gag tat cat aca ccc tgg tac     1322
Asn Ser Arg Leu Val Leu Phe Tyr Val Glu Tyr His Thr Pro Trp Tyr
300                 305                 310                 315 atg gct gaa ctc ttc cct ttc atc ctg ctt gga gtc ttt ggg ggt tta     1370
Met Ala Glu Leu Phe Pro Phe Ile Leu Leu Gly Val Phe Gly Gly Leu
                 320                 325                 330 tgg gga acc ctc ttc aca cgc tgc aac att gct tgg tgc agg agg cgt     1418
Trp Gly Thr Leu Phe Thr Arg Cys Asn Ile Ala Trp Cys Arg Arg Arg
             335                 340                 345
```

```
aag acc acc agg ctg ggc agg tac cca gtg ttg gag gtt att gcg gtg     1466
Lys Thr Thr Arg Leu Gly Arg Tyr Pro Val Leu Glu Val Ile Ala Val
        350                 355                 360 aca gcc gtc acc gcc atc gtg gcc tac ccc aat ccc tac act cgc cag     1514
Thr Ala Val Thr Ala Ile Val Ala Tyr Pro Asn Pro Tyr Thr Arg Gln
365                 370                 375 agc acc agt gag ctc atc tct gag ctc ttc aac gat tgt ggg gct ctc     1562
Ser Thr Ser Glu Leu Ile Ser Glu Leu Phe Asn Asp Cys Gly Ala Leu
380                 385                 390                 395 gag tct tct cag ctc tgt gac tac atc aac gac ccc aac atg act cgg     1610
Glu Ser Ser Gln Leu Cys Asp Tyr Ile Asn Asp Pro Asn Met Thr Arg
                400                 405                 410 cct gtg gat gac att ccg gac cgg ccg gct ggg gtt gga gtt tac aca     1658
Pro Val Asp Asp Ile Pro Asp Arg Pro Ala Gly Val Gly Val Tyr Thr
            415                 420                 425 gcc atg tgg cag ctg gcc ttg gca ctg tac ttc aaa ata gtc att act     1706
Ala Met Trp Gln Leu Ala Leu Ala Leu Tyr Phe Lys Ile Val Ile Thr
        430                 435                 440 ata ttt acc ttt ggc atg aag att ccc tca ggt ctc ttc atc ccc agt     1754
Ile Phe Thr Phe Gly Met Lys Ile Pro Ser Gly Leu Phe Ile Pro Ser
445                 450                 455 atg gct gtc gga gcc atg gca ggc cgg atg gtg gga atc ggt gtg gag     1802
Met Ala Val Gly Ala Met Ala Gly Arg Met Val Gly Ile Gly Val Glu
460                 465                 470                 475 cag ctg gcc tac cat cac cat gac tgg atc atc ttc agg aac tgg tgc     1850
Gln Leu Ala Tyr His His His Asp Trp Ile Ile Phe Arg Asn Trp Cys
                480                 485                 490 agg cct gga gcg gac tgt gtc aca cca ggg ctt tat gcg atg gtg gga     1898
Arg Pro Gly Ala Asp Cys Val Thr Pro Gly Leu Tyr Ala Met Val Gly
            495                 500                 505 gct gca gcc tgt cta ggt ggg gtg act agg atg aca gtg tct cta gtg     1946
Ala Ala Ala Cys Leu Gly Gly Val Thr Arg Met Thr Val Ser Leu Val
        510                 515                 520 gtc att atg ttt gaa ctg act gga ggt ctg gag tat att gta ccc cta     1994
Val Ile Met Phe Glu Leu Thr Gly Gly Leu Glu Tyr Ile Val Pro Leu
525                 530                 535 atg gca gct gct gtc acc agc aag tgg gtg gct gat gcc ttt ggg aaa     2042
Met Ala Ala Ala Val Thr Ser Lys Trp Val Ala Asp Ala Phe Gly Lys
540                 545                 550                 555 gaa ggg att tat gaa gcc cac atc cat ctg aat ggg tac cca ttt ctt     2090
Glu Gly Ile Tyr Glu Ala His Ile His Leu Asn Gly Tyr Pro Phe Leu
                560                 565                 570 gat gtg aag gat gag ttc acc cac cgt acg ctg gcc act gat gtg atg     2138
Asp Val Lys Asp Glu Phe Thr His Arg Thr Leu Ala Thr Asp Val Met
            575                 580                 585 cgg ccc cgg agg gag gaa ccg cca tta tcg gta cta acc cag gac agc     2186
Arg Pro Arg Arg Glu Glu Pro Pro Leu Ser Val Leu Thr Gln Asp Ser
        590                 595                 600 atg act gtg gag gac gtg gag act ctc atc aag gag aca gac tac aac     2234
Met Thr Val Glu Asp Val Glu Thr Leu Ile Lys Glu Thr Asp Tyr Asn
605                 610                 615 ggc ttt cct gtg ctc gtc tcc aga gac tcg gag cgt ctc atc ggg ttt     2282
Gly Phe Pro Val Leu Val Ser Arg Asp Ser Glu Arg Leu Ile Gly Phe
620                 625                 630                 635 gcc cag agg cgg gag cta atc ttg gct ata aaa aat gcc agg cag agg     2330
Ala Gln Arg Arg Glu Leu Ile Leu Ala Ile Lys Asn Ala Arg Gln Arg
                640                 645                 650 caa gag ggc att gtg agc aat tcc atc atg tac ttc aca gag gag cct     2378
Gln Glu Gly Ile Val Ser Asn Ser Ile Met Tyr Phe Thr Glu Glu Pro
            655                 660                 665
```

| | | | | | | | | | | | | | | |
|---|---|---|---|---|---|---|---|---|---|---|---|---|---|---|
| cct | gag | ctg | cct | gcc | aac | agc | cca | cat | cca | ctg | aag | ctg | agg | cgc | att | 2426 |
| Pro | Glu | Leu | Pro | Ala | Asn | Ser | Pro | His | Pro | Leu | Lys | Leu | Arg | Arg | Ile |
| | 670 | | | | | 675 | | | | 680 | | | | |

| | | | | | | | | | | | | | | |
|---|---|---|---|---|---|---|---|---|---|---|---|---|---|---|
| ttc | aac | ctg | agc | cct | ttc | acg | gtc | aca | gat | cac | acc | ccc | atg | gag | acg | 2474 |
| Phe | Asn | Leu | Ser | Pro | Phe | Thr | Val | Thr | Asp | His | Thr | Pro | Met | Glu | Thr |
| 685 | | | | | 690 | | | | | 695 | | | | |

| | | | | | | | | | | | | | | |
|---|---|---|---|---|---|---|---|---|---|---|---|---|---|---|
| gtg | gtg | gac | att | ttc | cgg | aaa | ctg | ggg | ctc | cga | caa | tgc | ctg | gtg | aca | 2522 |
| Val | Val | Asp | Ile | Phe | Arg | Lys | Leu | Gly | Leu | Arg | Gln | Cys | Leu | Val | Thr |
| 700 | | | | | 705 | | | | | 710 | | | | | 715 |

| | | | | | | | | | | | | | | |
|---|---|---|---|---|---|---|---|---|---|---|---|---|---|---|
| cgg | agt | ggg | aga | ctt | ctt | ggg | atc | atc | aca | aaa | aag | gat | gtt | ctg | aga | 2570 |
| Arg | Ser | Gly | Arg | Leu | Leu | Gly | Ile | Ile | Thr | Lys | Lys | Asp | Val | Leu | Arg |
| | | | | 720 | | | | | 725 | | | | | 730 |

| | | | | | | | | | | | | | | |
|---|---|---|---|---|---|---|---|---|---|---|---|---|---|---|
| cac | atg | gcc | cag | atg | gca | aac | cag | gac | cct | gaa | tcc | atc | atg | ttt | aat | 2618 |
| His | Met | Ala | Gln | Met | Ala | Asn | Gln | Asp | Pro | Glu | Ser | Ile | Met | Phe | Asn |
| | | 735 | | | | | 740 | | | | | 745 | | | tag cactaagatg ggcattattt tgagaagtca ataattatat catttttaaa    2671 gaaataacca agtgatatat tatgatccta atgaaaaaac ttgcactgaa ggcaaaaaaa    2731 aaaaaaaa    2739

<210> SEQ ID NO 8
<211> LENGTH: 747
<212> TYPE: PRT
<213> ORGANISM: Mus musculus

<400> SEQUENCE: 8

Met Asp Phe Leu Glu Glu Pro Phe Pro Asp Val Gly Thr Tyr Glu Asp
 1               5                  10                  15

Phe His Thr Ile Asp Trp Leu Arg Glu Lys Ser Arg Asp Thr Asp Arg
            20                  25                  30

His Arg Lys Ile Thr Ser Lys Ser Lys Glu Ser Ile Trp Glu Phe Ile
        35                  40                  45

Lys Ser Leu Leu Asp Ala Trp Ser Gly Trp Val Val Met Leu Leu Ile
    50                  55                  60

Gly Leu Leu Ala Gly Thr Leu Ala Gly Val Ile Asp Leu Ala Val Asp
65                  70                  75                  80

Trp Met Thr Asp Leu Lys Glu Gly Val Cys Leu Ser Ala Phe Trp Tyr
                85                  90                  95

Ser His Glu Gln Cys Cys Trp Thr Ser Asn Glu Thr Thr Phe Glu Asp
            100                 105                 110

Arg Asp Lys Cys Pro Leu Trp Gln Lys Trp Ser Glu Leu Leu Leu Ser
        115                 120                 125

Gln Ser Glu Gly Ala Ser Ala Tyr Ile Leu Asn Tyr Leu Met Tyr Ile
    130                 135                 140

Leu Trp Ala Leu Leu Phe Ala Phe Leu Ala Val Ser Leu Val Arg Val
145                 150                 155                 160

Phe Ala Pro Tyr Ala Cys Gly Ser Gly Ile Pro Glu Ile Lys Thr Ile
                165                 170                 175

Leu Ser Gly Phe Ile Ile Arg Gly Tyr Leu Gly Lys Trp Thr Leu Leu
            180                 185                 190

Ile Lys Thr Val Thr Leu Val Leu Val Val Ser Ser Gly Leu Ser Leu
        195                 200                 205

Gly Lys Glu Gly Pro Leu Val His Val Ala Cys Cys Gly Asn Phe
    210                 215                 220

Phe Ser Ser Leu Phe Ser Lys Tyr Ser Lys Asn Glu Gly Lys Arg Arg
225                 230                 235                 240

-continued

```
Glu Val Leu Ser Ala Ala Ala Ala Gly Val Ser Val Ala Phe Gly
            245                 250                 255

Ala Pro Ile Gly Gly Val Leu Phe Ser Leu Glu Glu Val Ser Tyr Tyr
            260                 265                 270

Phe Pro Leu Lys Thr Leu Trp Arg Ser Phe Phe Ala Ala Leu Val Ala
            275                 280                 285

Ala Phe Thr Leu Arg Ser Ile Asn Pro Phe Gly Asn Ser Arg Leu Val
            290                 295                 300

Leu Phe Tyr Val Glu Tyr His Thr Pro Trp Tyr Met Ala Glu Leu Phe
305                 310                 315                 320

Pro Phe Ile Leu Leu Gly Val Phe Gly Gly Leu Trp Gly Thr Leu Phe
            325                 330                 335

Thr Arg Cys Asn Ile Ala Trp Cys Arg Arg Lys Thr Thr Arg Leu
            340                 345                 350

Gly Arg Tyr Pro Val Leu Glu Val Ile Ala Val Thr Ala Val Thr Ala
            355                 360                 365

Ile Val Ala Tyr Pro Asn Pro Tyr Thr Arg Gln Ser Thr Ser Glu Leu
    370                 375                 380

Ile Ser Glu Leu Phe Asn Asp Cys Gly Ala Leu Glu Ser Ser Gln Leu
385                 390                 395                 400

Cys Asp Tyr Ile Asn Asp Pro Asn Met Thr Arg Pro Val Asp Asp Ile
                405                 410                 415

Pro Asp Arg Pro Ala Gly Val Gly Val Tyr Thr Ala Met Trp Gln Leu
            420                 425                 430

Ala Leu Ala Leu Tyr Phe Lys Ile Val Ile Thr Ile Phe Thr Phe Gly
            435                 440                 445

Met Lys Ile Pro Ser Gly Leu Phe Ile Pro Ser Met Ala Val Gly Ala
    450                 455                 460

Met Ala Gly Arg Met Val Gly Ile Gly Val Glu Gln Leu Ala Tyr His
465                 470                 475                 480

His His Asp Trp Ile Ile Phe Arg Asn Trp Cys Arg Pro Gly Ala Asp
                485                 490                 495

Cys Val Thr Pro Gly Leu Tyr Ala Met Val Gly Ala Ala Ala Cys Leu
            500                 505                 510

Gly Gly Val Thr Arg Met Thr Val Ser Leu Val Val Ile Met Phe Glu
            515                 520                 525

Leu Thr Gly Gly Leu Glu Tyr Ile Val Pro Leu Met Ala Ala Ala Val
    530                 535                 540

Thr Ser Lys Trp Val Ala Asp Ala Phe Gly Lys Glu Gly Ile Tyr Glu
545                 550                 555                 560

Ala His Ile His Leu Asn Gly Tyr Pro Phe Leu Asp Val Lys Asp Glu
                565                 570                 575

Phe Thr His Arg Thr Leu Ala Thr Asp Val Met Arg Pro Arg Arg Glu
            580                 585                 590

Glu Pro Pro Leu Ser Val Leu Thr Gln Asp Ser Met Thr Val Glu Asp
            595                 600                 605

Val Glu Thr Leu Ile Lys Glu Thr Asp Tyr Asn Gly Phe Pro Val Leu
            610                 615                 620

Val Ser Arg Asp Ser Glu Arg Leu Ile Gly Phe Ala Gln Arg Arg Glu
625                 630                 635                 640

Leu Ile Leu Ala Ile Lys Asn Ala Arg Gln Arg Gln Glu Gly Ile Val
                645                 650                 655
```

```
Ser Asn Ser Ile Met Tyr Phe Thr Glu Glu Pro Pro Glu Leu Pro Ala
        660                 665                 670

Asn Ser Pro His Pro Lys Leu Arg Arg Ile Phe Asn Leu Ser Pro
    675                 680                 685

Phe Thr Val Thr Asp His Thr Pro Met Glu Thr Val Asp Ile Phe
    690                 695                 700

Arg Lys Leu Gly Leu Arg Gln Cys Leu Val Thr Arg Ser Gly Arg Leu
705                 710                 715                 720

Leu Gly Ile Ile Thr Lys Lys Asp Val Leu Arg His Met Ala Gln Met
                725                 730                 735

Ala Asn Gln Asp Pro Glu Ser Ile Met Phe Asn
                740                 745

<210> SEQ ID NO 9
<211> LENGTH: 5541
<212> TYPE: DNA
<213> ORGANISM: Homo sapiens
<220> FEATURE:
<221> NAME/KEY: CDS
<222> LOCATION: (27)..(2636)
<223> OTHER INFORMATION: ClC-6

<400> SEQUENCE: 9
gtccagagtg gcagtaaagg aggaag atg gcg ggg tgc agg ggg tct ctg tgc        53
                             Met Ala Gly Cys Arg Gly Ser Leu Cys
                               1               5 tgc tgc tgc agg tgg tgc tgc tgc ggt gag cgt gag acc cgc acc            101
Cys Cys Cys Arg Trp Cys Cys Cys Gly Glu Arg Glu Thr Arg Thr
 10              15                  20                  25 ccc gag gag ctg acc atc ctt gga gaa aca cag gag gag gag gat gag        149
Pro Glu Glu Leu Thr Ile Leu Gly Glu Thr Gln Glu Glu Glu Asp Glu
                 30                  35                  40 att ctt cca agg aaa gac tat gag agt ttg gat tat gat cgc tgt atc        197
Ile Leu Pro Arg Lys Asp Tyr Glu Ser Leu Asp Tyr Asp Arg Cys Ile
             45                  50                  55 aat gac cct tac ctg gaa gtt ttg gag acc atg gat aat aag aaa ggt        245
Asn Asp Pro Tyr Leu Glu Val Leu Glu Thr Met Asp Asn Lys Lys Gly
         60                  65                  70 cga aga tat gag gcg gtg aag tgg atg gtg gtg ttt gcc att gga gtc        293
Arg Arg Tyr Glu Ala Val Lys Trp Met Val Val Phe Ala Ile Gly Val
     75                  80                  85 tgc act ggc ctg gtg ggt ctc ttt gtg gac ttt ttt gtg cga ctc ttc        341
Cys Thr Gly Leu Val Gly Leu Phe Val Asp Phe Phe Val Arg Leu Phe
 90                  95                 100                 105 acc caa ctc aag ttc gga gtg gta cag aca tcg gtg gag gag tgc agc        389
Thr Gln Leu Lys Phe Gly Val Val Gln Thr Ser Val Glu Glu Cys Ser
                110                 115                 120 cag aaa ggc tgc ctc gct ctg tct ctc ctt gaa ctc ctg ggt ttt aac        437
Gln Lys Gly Cys Leu Ala Leu Ser Leu Leu Glu Leu Leu Gly Phe Asn
            125                 130                 135 ctc acc ttt gtc ttc ctg gca agc ctc ctt gtt ctc att gag ccg gtg        485
Leu Thr Phe Val Phe Leu Ala Ser Leu Leu Val Leu Ile Glu Pro Val
        140                 145                 150 gca gca ggt tcc ggg ata ccc gag gtc aaa tgc tat ctg aat ggc gta        533
Ala Ala Gly Ser Gly Ile Pro Glu Val Lys Cys Tyr Leu Asn Gly Val
    155                 160                 165 aag gtg cca gga atc gtc cgt ctc cgg acc ctg ctc tgc aag gtc ctt        581
Lys Val Pro Gly Ile Val Arg Leu Arg Thr Leu Leu Cys Lys Val Leu
170                 175                 180                 185 gga gtg ctg ttc agt gtg gct gga ggg ctc ttc gtg ggg aag gaa ggc        629
```

|  |  |  |  |  |  |  |  |  |  |  |  |  |  |  |  |
|---|---|---|---|---|---|---|---|---|---|---|---|---|---|---|---|
| Gly | Val | Leu | Phe | Ser | Val | Ala | Gly | Gly | Leu | Phe | Val | Gly | Lys | Glu | Gly |
|  |  |  | 190 |  |  |  | 195 |  |  |  | 200 |  |  |  |  |

| ccc | atg | atc | cac | agt | ggt | tcg | gtg | gtg | gga | gct | ggc | ctc | cct | cag | ttt | 677 |
|---|---|---|---|---|---|---|---|---|---|---|---|---|---|---|---|---|
| Pro | Met | Ile | His | Ser | Gly | Ser | Val | Val | Gly | Ala | Gly | Leu | Pro | Gln | Phe |  |
|  |  |  | 205 |  |  |  | 210 |  |  |  | 215 |  |  |  |  |  |

| cag | agc | atc | tcc | tta | cgg | aag | atc | cag | ttt | aac | ttc | ccc | tat | ttc | cga | 725 |
|---|---|---|---|---|---|---|---|---|---|---|---|---|---|---|---|---|
| Gln | Ser | Ile | Ser | Leu | Arg | Lys | Ile | Gln | Phe | Asn | Phe | Pro | Tyr | Phe | Arg |  |
|  |  | 220 |  |  |  |  | 225 |  |  |  |  | 230 |  |  |  |  |

| agc | gac | aga | gac | aag | aga | gac | ttt | gta | tca | gca | gga | gcg | gct | gct | gga | 773 |
|---|---|---|---|---|---|---|---|---|---|---|---|---|---|---|---|---|
| Ser | Asp | Arg | Asp | Lys | Arg | Asp | Phe | Val | Ser | Ala | Gly | Ala | Ala | Ala | Gly |  |
|  |  | 235 |  |  |  |  | 240 |  |  |  |  | 245 |  |  |  |  |

| gtt | gct | gca | gct | ttc | ggg | gcg | cca | atc | ggg | ggt | acc | ttg | ttc | agt | cta | 821 |
|---|---|---|---|---|---|---|---|---|---|---|---|---|---|---|---|---|
| Val | Ala | Ala | Ala | Phe | Gly | Ala | Pro | Ile | Gly | Gly | Thr | Leu | Phe | Ser | Leu |  |
| 250 |  |  |  | 255 |  |  |  | 260 |  |  |  | 265 |  |  |  |  |

| gag | gag | ggt | tcg | tcc | ttc | tgg | aac | caa | ggg | ctc | acg | tgg | aaa | gtg | ctc | 869 |
|---|---|---|---|---|---|---|---|---|---|---|---|---|---|---|---|---|
| Glu | Glu | Gly | Ser | Ser | Phe | Trp | Asn | Gln | Gly | Leu | Thr | Trp | Lys | Val | Leu |  |
|  |  |  |  | 270 |  |  |  | 275 |  |  |  | 280 |  |  |  |  |

| ttt | tgt | tcc | atg | tct | gcc | acc | ttc | acc | ctc | aac | ttc | ttc | cgt | tct | ggg | 917 |
|---|---|---|---|---|---|---|---|---|---|---|---|---|---|---|---|---|
| Phe | Cys | Ser | Met | Ser | Ala | Thr | Phe | Thr | Leu | Asn | Phe | Phe | Arg | Ser | Gly |  |
|  |  |  |  | 285 |  |  |  | 290 |  |  |  | 295 |  |  |  |  |

| att | cag | ttt | gga | agc | tgg | ggt | tcc | ttc | cag | ctc | cct | gga | ttg | ctg | aac | 965 |
|---|---|---|---|---|---|---|---|---|---|---|---|---|---|---|---|---|
| Ile | Gln | Phe | Gly | Ser | Trp | Gly | Ser | Phe | Gln | Leu | Pro | Gly | Leu | Leu | Asn |  |
|  |  |  | 300 |  |  |  | 305 |  |  |  | 310 |  |  |  |  |  |

| ttt | ggc | gag | ttt | aag | tgc | tct | gac | tct | gat | aaa | aaa | tgt | cat | ctc | tgg | 1013 |
|---|---|---|---|---|---|---|---|---|---|---|---|---|---|---|---|---|
| Phe | Gly | Glu | Phe | Lys | Cys | Ser | Asp | Ser | Asp | Lys | Lys | Cys | His | Leu | Trp |  |
|  | 315 |  |  |  |  | 320 |  |  |  |  | 325 |  |  |  |  |  |

| aca | gct | atg | gat | ttg | ggt | ttc | ttc | gtc | gtg | atg | ggg | gtc | att | ggg | ggc | 1061 |
|---|---|---|---|---|---|---|---|---|---|---|---|---|---|---|---|---|
| Thr | Ala | Met | Asp | Leu | Gly | Phe | Phe | Val | Val | Met | Gly | Val | Ile | Gly | Gly |  |
| 330 |  |  |  | 335 |  |  |  | 340 |  |  |  | 345 |  |  |  |  |

| ctc | ctg | gga | gcc | aca | ttc | aac | tgt | ctg | aac | aag | agg | ctt | gca | aag | tac | 1109 |
|---|---|---|---|---|---|---|---|---|---|---|---|---|---|---|---|---|
| Leu | Leu | Gly | Ala | Thr | Phe | Asn | Cys | Leu | Asn | Lys | Arg | Leu | Ala | Lys | Tyr |  |
|  |  |  | 350 |  |  |  | 355 |  |  |  | 360 |  |  |  |  |  |

| cgt | atg | cga | aac | gtg | cac | ccg | aaa | cct | aag | ctc | gtc | aga | gtc | tta | gag | 1157 |
|---|---|---|---|---|---|---|---|---|---|---|---|---|---|---|---|---|
| Arg | Met | Arg | Asn | Val | His | Pro | Lys | Pro | Lys | Leu | Val | Arg | Val | Leu | Glu |  |
|  |  | 365 |  |  |  |  | 370 |  |  |  |  | 375 |  |  |  |  |

| agc | ctc | ctt | gtg | tct | ctg | gta | acc | acc | gtg | gtg | gtg | ttt | gtg | gcc | tcg | 1205 |
|---|---|---|---|---|---|---|---|---|---|---|---|---|---|---|---|---|
| Ser | Leu | Leu | Val | Ser | Leu | Val | Thr | Thr | Val | Val | Val | Phe | Val | Ala | Ser |  |
|  |  | 380 |  |  |  |  | 385 |  |  |  |  | 390 |  |  |  |  |

| atg | gtg | tta | gga | gaa | tgc | cga | cag | atg | tcc | tct | tcg | agt | caa | atc | ggt | 1253 |
|---|---|---|---|---|---|---|---|---|---|---|---|---|---|---|---|---|
| Met | Val | Leu | Gly | Glu | Cys | Arg | Gln | Met | Ser | Ser | Ser | Ser | Gln | Ile | Gly |  |
|  | 395 |  |  |  |  | 400 |  |  |  |  | 405 |  |  |  |  |  |

| aat | gac | tca | ttc | cag | ctc | cag | gtc | aca | gaa | gat | gtg | aat | tca | agt | atc | 1301 |
|---|---|---|---|---|---|---|---|---|---|---|---|---|---|---|---|---|
| Asn | Asp | Ser | Phe | Gln | Leu | Gln | Val | Thr | Glu | Asp | Val | Asn | Ser | Ser | Ile |  |
| 410 |  |  |  | 415 |  |  |  | 420 |  |  |  | 425 |  |  |  |  |

| aag | aca | ttt | ttt | tgt | ccc | aat | gat | acc | tac | aat | gac | atg | gcc | aca | ctc | 1349 |
|---|---|---|---|---|---|---|---|---|---|---|---|---|---|---|---|---|
| Lys | Thr | Phe | Phe | Cys | Pro | Asn | Asp | Thr | Tyr | Asn | Asp | Met | Ala | Thr | Leu |  |
|  |  |  | 430 |  |  |  | 435 |  |  |  | 440 |  |  |  |  |  |

| ttc | ttc | aac | ccg | cag | gag | tct | gcc | atc | ctc | cag | ctc | ttc | cac | cag | gat | 1397 |
|---|---|---|---|---|---|---|---|---|---|---|---|---|---|---|---|---|
| Phe | Phe | Asn | Pro | Gln | Glu | Ser | Ala | Ile | Leu | Gln | Leu | Phe | His | Gln | Asp |  |
|  |  |  | 445 |  |  |  | 450 |  |  |  | 455 |  |  |  |  |  |

| ggt | act | ttc | agc | ccc | gtc | act | ctg | gcc | ttg | ttc | ttc | gtt | ctc | tat | ttc | 1445 |
|---|---|---|---|---|---|---|---|---|---|---|---|---|---|---|---|---|
| Gly | Thr | Phe | Ser | Pro | Val | Thr | Leu | Ala | Leu | Phe | Phe | Val | Leu | Tyr | Phe |  |
|  |  |  | 460 |  |  |  | 465 |  |  |  | 470 |  |  |  |  |  |

| ttg | ctt | gca | tgt | tgg | act | tac | ggc | att | tct | gtt | cca | agt | ggc | ctt | ttt | 1493 |
|---|---|---|---|---|---|---|---|---|---|---|---|---|---|---|---|---|
| Leu | Leu | Ala | Cys | Trp | Thr | Tyr | Gly | Ile | Ser | Val | Pro | Ser | Gly | Leu | Phe |  |
| 475 |  |  |  | 480 |  |  |  | 485 |  |  |  |  |  |  |  |  |

| gtg | cct | tct | ctg | ctg | tgt | gga | gct | gct | ttt | gga | cgt | tta | gtt | gcc | aat | 1541 |
|---|---|---|---|---|---|---|---|---|---|---|---|---|---|---|---|---|
| Val | Pro | Ser | Leu | Leu | Cys | Gly | Ala | Ala | Phe | Gly | Arg | Leu | Val | Ala | Asn |  |
| 490 |  |  |  | 495 |  |  |  | 500 |  |  |  | 505 |  |  |  |  |

```
gtc cta aaa agc tac att gga ttg ggc cac atc tat tcg ggg acc ttt    1589
Val Leu Lys Ser Tyr Ile Gly Leu Gly His Ile Tyr Ser Gly Thr Phe
            510                 515                 520 gcc ctg att ggt gca gcg gct ttc ttg ggc ggg gtg gtc cgc atg acc    1637
Ala Leu Ile Gly Ala Ala Ala Phe Leu Gly Gly Val Val Arg Met Thr
            525                 530                 535 atc agc ctc acg gtc atc ctg atc gag tcc acc aat gag atc acc tac    1685
Ile Ser Leu Thr Val Ile Leu Ile Glu Ser Thr Asn Glu Ile Thr Tyr
            540                 545                 550 ggg ctc ccc atc atg gtc aca ctg atg gtg gcc aaa tgg aca ggg gac    1733
Gly Leu Pro Ile Met Val Thr Leu Met Val Ala Lys Trp Thr Gly Asp
    555                 560                 565 ttt ttc aat aag ggc att tat gat atc cac gtg ggc ctg cga ggc gtg    1781
Phe Phe Asn Lys Gly Ile Tyr Asp Ile His Val Gly Leu Arg Gly Val
570                 575                 580                 585 ccg ctt ctg gaa tgg gag aca gag gtg gaa atg gac aag ctg aga gcc    1829
Pro Leu Leu Glu Trp Glu Thr Glu Val Glu Met Asp Lys Leu Arg Ala
                590                 595                 600 agc gac atc atg gag ccc aac ctg acc tac gtc tac ccg cac acc cgc    1877
Ser Asp Ile Met Glu Pro Asn Leu Thr Tyr Val Tyr Pro His Thr Arg
            605                 610                 615 atc cag tct ctg gtg agc atc ctg cgc acc acg gtc cac cat gcc ttc    1925
Ile Gln Ser Leu Val Ser Ile Leu Arg Thr Thr Val His His Ala Phe
            620                 625                 630 ccg gtg gtc aca gag aac cgc ggt aac gag aag gag ttc atg aag ggc    1973
Pro Val Val Thr Glu Asn Arg Gly Asn Glu Lys Glu Phe Met Lys Gly
            635                 640                 645 aac cag ctc atc agc aac aac atc aag ttc aag aaa tcc agc atc ctc    2021
Asn Gln Leu Ile Ser Asn Asn Ile Lys Phe Lys Lys Ser Ser Ile Leu
650                 655                 660                 665 acc cgg gct ggc gag cag cgc aaa cgg agc cag tcc atg aag tcc tac    2069
Thr Arg Ala Gly Glu Gln Arg Lys Arg Ser Gln Ser Met Lys Ser Tyr
            670                 675                 680 cca tcc agc gag cta cgg aac atg tgt gat gag cac atc gcc tct gag    2117
Pro Ser Ser Glu Leu Arg Asn Met Cys Asp Glu His Ile Ala Ser Glu
            685                 690                 695 gag cca gcc gag aag gag gac ctc ctg cag cag atg ctg gaa agg aga    2165
Glu Pro Ala Glu Lys Glu Asp Leu Leu Gln Gln Met Leu Glu Arg Arg
    700                 705                 710 tac act ccc tac ccc aac cta tac cct gac cag tcc cca agt gaa gac    2213
Tyr Thr Pro Tyr Pro Asn Leu Tyr Pro Asp Gln Ser Pro Ser Glu Asp
    715                 720                 725 tgg acc atg gag gag cgg ttc cgc cct ctg acc ttc cac ggc ctg atc    2261
Trp Thr Met Glu Glu Arg Phe Arg Pro Leu Thr Phe His Gly Leu Ile
730                 735                 740                 745 ctt cgg tcg cag ctt gtc acc ctg ctt gtc cga gga gtt tgt tac tct    2309
Leu Arg Ser Gln Leu Val Thr Leu Leu Val Arg Gly Val Cys Tyr Ser
            750                 755                 760 gaa agc cag tcg agc gcc agc cag ccg cgc ctc tcc tat gcc gag atg    2357
Glu Ser Gln Ser Ser Ala Ser Gln Pro Arg Leu Ser Tyr Ala Glu Met
            765                 770                 775 gcc gag gac tac ccg cgg tac ccc gac atc cac gac ctg gac ctg acg    2405
Ala Glu Asp Tyr Pro Arg Tyr Pro Asp Ile His Asp Leu Asp Leu Thr
            780                 785                 790 ctg ctc aac ccg cgc atg atc gtg gat gtc acc cca tac atg aac cct    2453
Leu Leu Asn Pro Arg Met Ile Val Asp Val Thr Pro Tyr Met Asn Pro
    795                 800                 805 tcg cct ttc acc gtc tcg ccc aac acc cac gtc tcc caa gtc ttc aac    2501
Ser Pro Phe Thr Val Ser Pro Asn Thr His Val Ser Gln Val Phe Asn
810                 815                 820                 825
```

```
ctg ttc aga acg atg ggc ctg cgc cac ctg ccc gtg gtg aac gct gtg    2549
Leu Phe Arg Thr Met Gly Leu Arg His Leu Pro Val Val Asn Ala Val
                830                 835                 840 gga gag atc gtg ggg atc atc aca cgg cac aac ctc acc tat gaa ttt    2597
Gly Glu Ile Val Gly Ile Ile Thr Arg His Asn Leu Thr Tyr Glu Phe
            845                 850                 855 ctg cag gcc cgg ctg agg cag cac tac cag acc atc tga cagcccagcc     2646
Leu Gln Ala Arg Leu Arg Gln His Tyr Gln Thr Ile
        860                 865 caccctctcc tggtgctgcc tggggaggca aatcatgctc actccggcgg gcacagctgg   2706
ctggggctgt tccggggcat ggaagattcc cagttaccca ctcactcaga aagccgggag   2766
tcatcggaca ccttgctggt cagaggccct ggggtggtt ttgaaccatc agagcttgga    2826
cttttctgac ttccccagca aggatcttcc cacttcctgc tccctgtgtt cccaccctcc   2886
agtgttggca caggcccacc cctggctcca ccagagccag aagcagaggt agaatcaggc   2946
gggccccggg ctgcactccg agcagtgttc ctggccatct ttgctacttt cctagagaac   3006
ccggctgttg cctaaaatgt gtgagaggga cttggccaag gcaaaagctg ggagatgcc    3066
agtgacaaca tacagttcat gactaggttt aggaattggg cactgagaaa attctcaata   3126
tttcagagag tccttccctt atttgggact cctaacacgg tatcctcgct agtttgtttt   3186
aagggaaaca ctctgctcct gggtgtgagc agaggctctg gtcttgccct gtggtttgac   3246
tctccttaga accaccgccc accagaaaca taaaggatta aaatcacact aataacccct   3306
ggatggtcaa tctgataata ggatcagatt tacgtctacc ctaattctta acattgcagc   3366
tttctctcca tctgcagatt attcccagtc tcccagtaac acgtttctac ccagatcctt   3426
tttcatttcc ttaagttttg atctccgtct tcctgatgaa gcaggcagag ctcagaggat   3486
cttggcatca cccaccaaag ttagctgaaa gcagggcact cctggataaa gcagcttcac   3546
tcaactctgg ggaatgctac cattttttt ccaaagtaga aaggaagcac ttctgagcca    3606
gtgaccactg aaaggtatgt gctatgataa agcagatggc ctatttgagg aagagggtgt   3666
ctgcccttca caaacacctc tctctcccct gcactagctg tcccaagctt acatacagag   3726
gcccttcagg agggcctcct gtgccgcagg gagggtgcgt ggggaagatg cttcctgcca   3786
gcacgtgcct gaaggtttca catgaagcat gggaagcgca ccctgtcgtt cagtgacgtc   3846
attcttctcc aggctggccc gccccctctg actaggcacc caaagtgagc atctgggcat   3906
tgggcattca tgcttatctt cccccacctt ctacatggta tcagtcccag caggcatccc   3966
tgggcagac gtgctttggc tcaagatggc cttcatttac gtttagtttt ttttaaaacc    4026
gtggaggttg cccacgggcc tcggcacctg gccctggcag cacagctctc aggcccagcc   4086
ctgggcgacc tccttggcca agtctgcctt tcaccctggg gtgagcatca gtcctggctc   4146
tgctggtcca gatcttgcgc tcagcacact ctagggaata attccactcc agagatgggg   4206
ctgcttcaag gtcttttcta gctgattgtg gcccctccat tttccccatt tcttatctc    4266
cctgaccaaa attgctttga cttctaaatg tttctgcttc ccagaatgca cctgacttat   4326
gaaatgggga taatactccc aggaaatagc gcaggacatc acaaggacca aaaggcaat    4386
tcttatttaa atgttactat ttggccagct gctgctgtgt tttatggcag tgttcagagc   4446
ttgatcacgt tatttcttcc ttttattaag aaggaagcca attgtccaag tcaggagaat   4506
ggtgtgatca cctgtcacag acactttgtc ccctctcccc gccccttcct ggagctggca   4566
gagctaacgc cctgcaggag gaccccggcc tctcgagggc tggatcagca gccgcctgcc   4626
```

-continued

```
ctgaggctgc cccggtgaat gttattggaa ttcatccctc gtgcacatcc tgttgtgttt    4686
aagtcaccag atattttgtt cccatcagtt tagcccagag atagacagta gaatgcaaat    4746
acctccctcc cctaaactga ctggacggct gccaaggagg ccccaaaccc aggccccatg    4806
caaaggcacg tggtttcctt ttctcctctc tctgcatctg cgctttccag ataagcccaa    4866
agacagcaac ttctccactc atgacaaatc aactgtgacc ctcgctcctt ccatttctgt    4926
ccattagaaa ccagccttt cagcatctca cccattagca gccccatcac ccagtgatca    4986
gtcgcctcag taaagcagat ctgtggatgg ggagcctacg ggtggtaaga agtggtgttt    5046
tgtgtttcat ctccagcttg gtgttccatg gcccctaggc gaggtgatca gggagtgggg    5106
ccaatgggcc cccggccctg gctttgggac cttgtgctga gggatgattt gctcctgacc    5166
ttgattaact taacagttcc cagctggaag ggacactttc aggacccagt ccactgtatg    5226
gcatttgtga tgcagaatta tgcactgaca tgaccctggg tgacaggaaa gcctttcgag    5286
aggcccaagg tggcctcgcc agccctgcag tattgatgtg cagtattgca ccacagctct    5346
gcggaccttg gccattgccg cagtcgcagc ttccttttt ctgtttgcac tgtttgtttg    5406
tatgatgtta gctaattcca ctgtgtatat aaattgtatt ttttttaatt tgtaaaatgc    5466
tatttttatt tgaacctttg gaacttggga gttctcattg taaccctaac atgtgagaat    5526
aaaatgtctt ctgtc                                                     5541
```

<210> SEQ ID NO 10
<211> LENGTH: 869
<212> TYPE: PRT
<213> ORGANISM: Homo sapiens

<400> SEQUENCE: 10

```
Met Ala Gly Cys Arg Gly Ser Leu Cys Cys Cys Arg Trp Cys Cys
 1               5                  10                  15

Cys Cys Gly Glu Arg Glu Thr Arg Thr Pro Glu Glu Leu Thr Ile Leu
                20                  25                  30

Gly Glu Thr Gln Glu Glu Glu Asp Glu Ile Leu Pro Arg Lys Asp Tyr
            35                  40                  45

Glu Ser Leu Asp Tyr Asp Arg Cys Ile Asn Asp Pro Tyr Leu Glu Val
        50                  55                  60

Leu Glu Thr Met Asp Asn Lys Lys Gly Arg Arg Tyr Glu Ala Val Lys
    65                  70                  75                  80

Trp Met Val Val Phe Ala Ile Gly Val Cys Thr Gly Leu Val Gly Leu
                85                  90                  95

Phe Val Asp Phe Phe Val Arg Leu Thr Gln Leu Lys Phe Gly Val
                100                 105                 110

Val Gln Thr Ser Val Glu Glu Cys Ser Gln Lys Gly Cys Leu Ala Leu
            115                 120                 125

Ser Leu Leu Glu Leu Leu Gly Phe Asn Leu Thr Phe Val Phe Leu Ala
        130                 135                 140

Ser Leu Leu Val Leu Ile Glu Pro Val Ala Ala Gly Ser Gly Ile Pro
    145                 150                 155                 160

Glu Val Lys Cys Tyr Leu Asn Gly Val Lys Val Pro Gly Ile Val Arg
                165                 170                 175

Leu Arg Thr Leu Leu Cys Lys Val Leu Gly Val Leu Phe Ser Val Ala
                180                 185                 190

Gly Gly Leu Phe Val Gly Lys Glu Gly Pro Met Ile His Ser Gly Ser
            195                 200                 205
```

-continued

```
Val Val Gly Ala Gly Leu Pro Gln Phe Gln Ser Ile Ser Leu Arg Lys
    210                 215                 220

Ile Gln Phe Asn Phe Pro Tyr Phe Arg Ser Asp Arg Asp Lys Arg Asp
225                 230                 235                 240

Phe Val Ser Ala Gly Ala Ala Gly Val Ala Ala Phe Gly Ala
                    245                 250                 255

Pro Ile Gly Gly Thr Leu Phe Ser Leu Glu Glu Gly Ser Ser Phe Trp
                260                 265                 270

Asn Gln Gly Leu Thr Trp Lys Val Leu Phe Cys Ser Met Ser Ala Thr
            275                 280                 285

Phe Thr Leu Asn Phe Phe Arg Ser Gly Ile Gln Phe Gly Ser Trp Gly
290                 295                 300

Ser Phe Gln Leu Pro Gly Leu Leu Asn Phe Gly Glu Phe Lys Cys Ser
305                 310                 315                 320

Asp Ser Asp Lys Lys Cys His Leu Trp Thr Ala Met Asp Leu Gly Phe
                325                 330                 335

Phe Val Val Met Gly Val Ile Gly Gly Leu Leu Gly Ala Thr Phe Asn
                340                 345                 350

Cys Leu Asn Lys Arg Leu Ala Lys Tyr Arg Met Arg Asn Val His Pro
            355                 360                 365

Lys Pro Lys Leu Val Arg Val Leu Glu Ser Leu Leu Val Ser Leu Val
370                 375                 380

Thr Thr Val Val Phe Val Ala Ser Met Val Leu Gly Glu Cys Arg
385                 390                 395                 400

Gln Met Ser Ser Ser Gln Ile Gly Asn Asp Ser Phe Gln Leu Gln
                405                 410                 415

Val Thr Glu Asp Val Asn Ser Ser Ile Lys Thr Phe Cys Pro Asn
                420                 425                 430

Asp Thr Tyr Asn Asp Met Ala Thr Leu Phe Phe Asn Pro Gln Glu Ser
            435                 440                 445

Ala Ile Leu Gln Leu Phe His Gln Asp Gly Thr Phe Ser Pro Val Thr
    450                 455                 460

Leu Ala Leu Phe Phe Val Leu Tyr Phe Leu Ala Cys Trp Thr Tyr
465                 470                 475                 480

Gly Ile Ser Val Pro Ser Gly Leu Phe Val Pro Ser Leu Leu Cys Gly
                485                 490                 495

Ala Ala Phe Gly Arg Leu Val Ala Asn Val Leu Lys Ser Tyr Ile Gly
                500                 505                 510

Leu Gly His Ile Tyr Ser Gly Thr Phe Ala Leu Ile Gly Ala Ala Ala
        515                 520                 525

Phe Leu Gly Gly Val Val Arg Met Thr Ile Ser Leu Thr Val Ile Leu
    530                 535                 540

Ile Glu Ser Thr Asn Glu Ile Thr Tyr Gly Leu Pro Ile Met Val Thr
545                 550                 555                 560

Leu Met Val Ala Lys Trp Thr Gly Asp Phe Phe Asn Lys Gly Ile Tyr
                565                 570                 575

Asp Ile His Val Gly Leu Arg Gly Val Pro Leu Leu Glu Trp Glu Thr
                580                 585                 590

Glu Val Glu Met Asp Lys Leu Arg Ala Ser Asp Ile Met Glu Pro Asn
            595                 600                 605

Leu Thr Tyr Val Tyr Pro His Thr Arg Ile Gln Ser Leu Val Ser Ile
        610                 615                 620

Leu Arg Thr Thr Val His His Ala Phe Pro Val Val Thr Glu Asn Arg
```

-continued

```
                         625                 630                 635
                                 640
   Gly Asn Glu Lys Glu Phe Met Lys Gly Asn Gln Leu Ile Ser Asn Asn
                     645                 650                 655
   Ile Lys Phe Lys Lys Ser Ser Ile Leu Thr Arg Ala Gly Glu Gln Arg
                 660                 665                 670
   Lys Arg Ser Gln Ser Met Lys Ser Tyr Pro Ser Ser Glu Leu Arg Asn
             675                 680                 685
   Met Cys Asp Glu His Ile Ala Ser Glu Glu Pro Ala Glu Lys Glu Asp
         690                 695                 700
   Leu Leu Gln Gln Met Leu Glu Arg Arg Tyr Thr Pro Tyr Pro Asn Leu
   705                 710                 715                 720
   Tyr Pro Asp Gln Ser Pro Ser Glu Asp Trp Thr Met Glu Glu Arg Phe
                     725                 730                 735
   Arg Pro Leu Thr Phe His Gly Leu Ile Leu Arg Ser Gln Leu Val Thr
                 740                 745                 750
   Leu Leu Val Arg Gly Val Cys Tyr Ser Glu Ser Gln Ser Ser Ala Ser
             755                 760                 765
   Gln Pro Arg Leu Ser Tyr Ala Glu Met Ala Glu Asp Tyr Pro Arg Tyr
         770                 775                 780
   Pro Asp Ile His Asp Leu Asp Leu Thr Leu Leu Asn Pro Arg Met Ile
   785                 790                 795                 800
   Val Asp Val Thr Pro Tyr Met Asn Pro Ser Pro Phe Thr Val Ser Pro
                     805                 810                 815
   Asn Thr His Val Ser Gln Val Phe Asn Leu Phe Arg Thr Met Gly Leu
                 820                 825                 830
   Arg His Leu Pro Val Val Asn Ala Val Gly Glu Ile Val Gly Ile Ile
             835                 840                 845
   Thr Arg His Asn Leu Thr Tyr Glu Phe Leu Gln Ala Arg Leu Arg Gln
         850                 855                 860
   His Tyr Gln Thr Ile
   865

<210> SEQ ID NO 11
<211> LENGTH: 2750
<212> TYPE: DNA
<213> ORGANISM: Rattus norvegicus
<220> FEATURE:
<221> NAME/KEY: CDS
<222> LOCATION: (69)..(2480)
<223> OTHER INFORMATION: ClC-7

<400> SEQUENCE: 11
ggggcgcggg tcacgggaac gctgccgggc tgccggctgt tcttgtggag tttggtcctc    60 agtgggcc atg gcc aac gtt tct aag aaa gtg tct tgg tcc ggc cga gat   110
         Met Ala Asn Val Ser Lys Lys Val Ser Trp Ser Gly Arg Asp
             1               5                  10 cgc gat gac gag gag ggg gcg ccg ctg ctt cga agg acg ggg caa cct   158
Arg Asp Asp Glu Glu Gly Ala Pro Leu Leu Arg Arg Thr Gly Gln Pro
 15                  20                  25                  30 gac gag gag acg ccg ctg ctg aac gga gcc ggg ccg ggc gcg cgc cag   206
Asp Glu Glu Thr Pro Leu Leu Asn Gly Ala Gly Pro Gly Ala Arg Gln
                 35                  40                  45 tct cat tct gca ctt ttc cga att gga cag atg aac aac gtg gag ctg   254
Ser His Ser Ala Leu Phe Arg Ile Gly Gln Met Asn Asn Val Glu Leu
             50                  55                  60 gat gat gaa ctc ctg gac ccg gaa gtg gac cct cct cac acc ttc ccc   302
Asp Asp Glu Leu Leu Asp Pro Glu Val Asp Pro Pro His Thr Phe Pro
```

-continued

|  |  |  |  |  |  |  |  |  |  |  |  |
|---|---|---|---|---|---|---|---|---|---|---|---|
|  |  | 65 |  |  |  | 70 |  |  |  | 75 |  | aag gag att cca cac aac gag aag ctc ctc tcc ctc aag tat gag agc    350
Lys Glu Ile Pro His Asn Glu Lys Leu Leu Ser Leu Lys Tyr Glu Ser
         80                  85                  90 ctg gac tat gac aat agt gag aat cag ctc ttc ctg gag gag gaa aga    398
Leu Asp Tyr Asp Asn Ser Glu Asn Gln Leu Phe Leu Glu Glu Glu Arg
 95                 100                 105                 110 cga atc aac cac acg gct ttc cgg aca gtg gag atc aag cgc tgg gtt    446
Arg Ile Asn His Thr Ala Phe Arg Thr Val Glu Ile Lys Arg Trp Val
                    115                 120                 125 atc tgt gcc ctc att gga atc ctc aca ggc cta gta gcc tgc ttc att    494
Ile Cys Ala Leu Ile Gly Ile Leu Thr Gly Leu Val Ala Cys Phe Ile
            130                 135                 140 gac att gta gtg gag aac ctg gca ggc ctc aag tac cga gtc atc aag    542
Asp Ile Val Val Glu Asn Leu Ala Gly Leu Lys Tyr Arg Val Ile Lys
        145                 150                 155 gac aac atc gac aag ttc aca gag aag ggc ggc ctg tcc ttc tcc ctc    590
Asp Asn Ile Asp Lys Phe Thr Glu Lys Gly Gly Leu Ser Phe Ser Leu
    160                 165                 170 ctg ctg tgg gcc aca ctg aac tct gcc ttc gtg ctc gtg ggg tct gtg    638
Leu Leu Trp Ala Thr Leu Asn Ser Ala Phe Val Leu Val Gly Ser Val
175                 180                 185                 190 att gtg gcc ttc ata gag cca gtt gct gct ggc agc gga atc cct cag    686
Ile Val Ala Phe Ile Glu Pro Val Ala Ala Gly Ser Gly Ile Pro Gln
                195                 200                 205 atc aag tgc ttc ctc aat ggg gtg aag atc ccc cac gtg gtg cgg ctc    734
Ile Lys Cys Phe Leu Asn Gly Val Lys Ile Pro His Val Val Arg Leu
            210                 215                 220 aag acg ctg gtg atc aag gtg tct ggc gtg att ctg tct gtg gta ggg    782
Lys Thr Leu Val Ile Lys Val Ser Gly Val Ile Leu Ser Val Val Gly
        225                 230                 235 gga ctg gct gtg gga aag gaa ggg cca atg atc cac tca gga tcc gtg    830
Gly Leu Ala Val Gly Lys Glu Gly Pro Met Ile His Ser Gly Ser Val
    240                 245                 250 att gct gca ggg att tca cag gga agg tcg acg tca ctc aag cga gat    878
Ile Ala Ala Gly Ile Ser Gln Gly Arg Ser Thr Ser Leu Lys Arg Asp
255                 260                 265                 270 ttt aag atc ttt gaa tat ttc cgc aga gat aca gag aag cgg gat ttt    926
Phe Lys Ile Phe Glu Tyr Phe Arg Arg Asp Thr Glu Lys Arg Asp Phe
                275                 280                 285 gtc tca gct gga gct gca gct gga gtg tct gct gcg ttt gga gca cct    974
Val Ser Ala Gly Ala Ala Ala Gly Val Ser Ala Ala Phe Gly Ala Pro
            290                 295                 300 gtg ggt ggg gtc ctg ttc agc ctg gaa gag ggc gcc tcc ttc tgg aat   1022
Val Gly Gly Val Leu Phe Ser Leu Glu Glu Gly Ala Ser Phe Trp Asn
        305                 310                 315 cag ttc ctg aca tgg aga att ttc ttt gct tcc atg att tcg acc ttt   1070
Gln Phe Leu Thr Trp Arg Ile Phe Phe Ala Ser Met Ile Ser Thr Phe
    320                 325                 330 aca ctg aat ttt gtt ctg agc atc tac cat gga aac atg tgg gac ctg   1118
Thr Leu Asn Phe Val Leu Ser Ile Tyr His Gly Asn Met Trp Asp Leu
335                 340                 345                 350 tcc agc cct ggc ctc ata aat ttt gga aga ttc gac tca gag aaa atg   1166
Ser Ser Pro Gly Leu Ile Asn Phe Gly Arg Phe Asp Ser Glu Lys Met
                355                 360                 365 gcc tac aca atc cat gag att cct gtc ttc atc gcc atg ggt gtg gtg   1214
Ala Tyr Thr Ile His Glu Ile Pro Val Phe Ile Ala Met Gly Val Val
            370                 375                 380 ggt ggc att ctt gga gcc gtg ttc aat gcc ttg aat tac tgg cta act   1262

-continued

```
Gly Gly Ile Leu Gly Ala Val Phe Asn Ala Leu Asn Tyr Trp Leu Thr
        385                 390                 395 atg ttt cga atc agg tac atc cac cgg ccc tgc ctc caa gtg att gag      1310
Met Phe Arg Ile Arg Tyr Ile His Arg Pro Cys Leu Gln Val Ile Glu
400                 405                 410 gcc atg ctg gtg gca gct gtc aca gcc aca gtt gca ttt gtc ttg att      1358
Ala Met Leu Val Ala Ala Val Thr Ala Thr Val Ala Phe Val Leu Ile
415                 420                 425                 430 tac tcg tct cga gat tgc cag ccc ctg cag ggg agc tcc atg tcc tac      1406
Tyr Ser Ser Arg Asp Cys Gln Pro Leu Gln Gly Ser Ser Met Ser Tyr
                435                 440                 445 cca ctc cag ctc ttc tgt gca gat ggc gaa tac aac tca atg gcc gca      1454
Pro Leu Gln Leu Phe Cys Ala Asp Gly Glu Tyr Asn Ser Met Ala Ala
        450                 455                 460 gcc ttc ttt aac acc cct gag aag agc gtc gtc agc ctg ttc cac gac      1502
Ala Phe Phe Asn Thr Pro Glu Lys Ser Val Val Ser Leu Phe His Asp
465                 470                 475 cca cca ggc tcc tat aat ccc atg act ctc ggc ctg ttc acc ctg gtc      1550
Pro Pro Gly Ser Tyr Asn Pro Met Thr Leu Gly Leu Phe Thr Leu Val
480                 485                 490 tac ttc ttc ctg gcc tgc tgg acc tat ggc ctc aca gta tct gct ggt      1598
Tyr Phe Phe Leu Ala Cys Trp Thr Tyr Gly Leu Thr Val Ser Ala Gly
495                 500                 505                 510 gtc ttc atc cca tcc ctg ctc att ggg gct gcc tgg ggc cga ctc ttt      1646
Val Phe Ile Pro Ser Leu Leu Ile Gly Ala Ala Trp Gly Arg Leu Phe
                515                 520                 525 ggc atc tcc atg tcc tac ctc aca gga gca gcg atc tgg gca gat ccg      1694
Gly Ile Ser Met Ser Tyr Leu Thr Gly Ala Ala Ile Trp Ala Asp Pro
        530                 535                 540 ggt aaa tac gcc ctg atg gga gct gct gct cag ctt ggt ggg atc gtg      1742
Gly Lys Tyr Ala Leu Met Gly Ala Ala Ala Gln Leu Gly Gly Ile Val
545                 550                 555 agg atg acc ctt agc ctg aca gtc atc atg atg gag gcc acc agc aac      1790
Arg Met Thr Leu Ser Leu Thr Val Ile Met Met Glu Ala Thr Ser Asn
        560                 565                 570 gtg acc tac ggt ttt ccc atc atg ttg gtg ctg atg act gcc aag att      1838
Val Thr Tyr Gly Phe Pro Ile Met Leu Val Leu Met Thr Ala Lys Ile
575                 580                 585                 590 gtg ggt gat gtc ttc att gag ggc ctc tat gac atg cac atc cag ctg      1886
Val Gly Asp Val Phe Ile Glu Gly Leu Tyr Asp Met His Ile Gln Leu
                595                 600                 605 caa agt gtg ccc ttc cta cac tgg gaa gcc ccg gtc acc tca cat tcg      1934
Gln Ser Val Pro Phe Leu His Trp Glu Ala Pro Val Thr Ser His Ser
        610                 615                 620 ctc act gcc agg gaa gta atg agc acg cct gtg acc tgc ctg agg agg      1982
Leu Thr Ala Arg Glu Val Met Ser Thr Pro Val Thr Cys Leu Arg Arg
625                 630                 635 aga gag aag gtt ggc atc atc gtg gat gtc cta agt gac aca gcg tct      2030
Arg Glu Lys Val Gly Ile Ile Val Asp Val Leu Ser Asp Thr Ala Ser
                640                 645                 650 aat cac aat ggg ttc cct gtg gtg gag gat gta gga gac acc cag cca      2078
Asn His Asn Gly Phe Pro Val Val Glu Asp Val Gly Asp Thr Gln Pro
655                 660                 665                 670 gcc aga ctc caa ggc cta atc ctg cgt tcc cag ctc atc gtg ctc ctg      2126
Ala Arg Leu Gln Gly Leu Ile Leu Arg Ser Gln Leu Ile Val Leu Leu
                675                 680                 685 aag cac aag gtg ttt gtg gag agg tcc aac atg ggt ttg gtg cag cgg      2174
Lys His Lys Val Phe Val Glu Arg Ser Asn Met Gly Leu Val Gln Arg
        690                 695                 700
```

```
aga ctg agg ctg aaa gac ttt cgc gat gcc tac cca cgc ttc ccc cca    2222
Arg Leu Arg Leu Lys Asp Phe Arg Asp Ala Tyr Pro Arg Phe Pro Pro
    705                 710                 715 atc cag tcc atc cac gta tcc cag gat gag cgg gag tgc acc atg gac    2270
Ile Gln Ser Ile His Val Ser Gln Asp Glu Arg Glu Cys Thr Met Asp
720                 725                 730 ctt tct gag ttc atg aac cct tct ccc tac act gtg cca cag gag gca    2318
Leu Ser Glu Phe Met Asn Pro Ser Pro Tyr Thr Val Pro Gln Glu Ala
735                 740                 745                 750 tct ctt cct cga gtg ttc aag ctg ttc cgg gct ctg ggc ctg agg cac    2366
Ser Leu Pro Arg Val Phe Lys Leu Phe Arg Ala Leu Gly Leu Arg His
            755                 760                 765 ctg gtc gta gta gac aac cac aat cag gtg gtc ggg ctg gtg acc agg    2414
Leu Val Val Val Asp Asn His Asn Gln Val Val Gly Leu Val Thr Arg
        770                 775                 780 aag gac cta gca aga tac cgc cta gga aaa gga ggc cta gaa gag ctt    2462
Lys Asp Leu Ala Arg Tyr Arg Leu Gly Lys Gly Gly Leu Glu Glu Leu
    785                 790                 795 tca ctg gcc cag acg tga gggctggccc ccacccttgg gcagcggcac           2510
Ser Leu Ala Gln Thr
    800 cccggcccct ctgcacctcc tcccagggtc cctggtctca gccaaagcct tgccctgggc  2570 agtgcagcaa caggagcaaa tgccctcccc gggcttggct ggtgtggggc ccagaccctt  2630 tgtcctgggc agttggttta catcatcagc atttccctat tccctgaacc tgcagtcctc  2690 agacttgtcc cactcctggg tcccttctcc caggatgtaa agtgtgtttt cacaccccct  2750
```

<210> SEQ ID NO 12
<211> LENGTH: 803
<212> TYPE: PRT
<213> ORGANISM: Rattus norvegicus

<400> SEQUENCE: 12

```
Met Ala Asn Val Ser Lys Lys Val Ser Trp Ser Gly Arg Asp Arg Asp
1               5                   10                  15

Asp Glu Glu Gly Ala Pro Leu Leu Arg Arg Thr Gly Gln Pro Asp Glu
            20                  25                  30

Glu Thr Pro Leu Leu Asn Gly Ala Gly Pro Gly Ala Arg Gln Ser His
        35                  40                  45

Ser Ala Leu Phe Arg Ile Gly Gln Met Asn Asn Val Glu Leu Asp Asp
    50                  55                  60

Glu Leu Leu Asp Pro Glu Val Asp Pro Pro His Thr Phe Pro Lys Glu
65                  70                  75                  80

Ile Pro His Asn Glu Lys Leu Leu Ser Leu Lys Tyr Glu Ser Leu Asp
                85                  90                  95

Tyr Asp Asn Ser Glu Asn Gln Leu Phe Leu Glu Glu Arg Arg Ile
            100                 105                 110

Asn His Thr Ala Phe Arg Thr Val Glu Ile Lys Arg Trp Val Ile Cys
        115                 120                 125

Ala Leu Ile Gly Ile Leu Thr Gly Leu Val Ala Cys Phe Ile Asp Ile
    130                 135                 140

Val Val Glu Asn Leu Ala Gly Leu Lys Tyr Arg Val Ile Lys Asp Asn
145                 150                 155                 160

Ile Asp Lys Phe Thr Glu Lys Gly Gly Leu Ser Phe Ser Leu Leu Leu
                165                 170                 175

Trp Ala Thr Leu Asn Ser Ala Phe Val Leu Val Gly Ser Val Ile Val
            180                 185                 190
```

```
Ala Phe Ile Glu Pro Val Ala Ala Gly Ser Gly Ile Pro Gln Ile Lys
            195                 200                 205

Cys Phe Leu Asn Gly Val Lys Ile Pro His Val Val Arg Leu Lys Thr
210                 215                 220

Leu Val Ile Lys Val Ser Gly Val Ile Leu Ser Val Val Gly Gly Leu
225                 230                 235                 240

Ala Val Gly Lys Glu Gly Pro Met Ile His Ser Gly Ser Val Ile Ala
            245                 250                 255

Ala Gly Ile Ser Gln Gly Arg Ser Thr Ser Leu Lys Arg Asp Phe Lys
            260                 265                 270

Ile Phe Glu Tyr Phe Arg Arg Asp Thr Glu Lys Arg Asp Phe Val Ser
            275                 280                 285

Ala Gly Ala Ala Gly Val Ser Ala Ala Phe Gly Ala Pro Val Gly
            290                 295                 300

Gly Val Leu Phe Ser Leu Glu Glu Gly Ala Ser Phe Trp Asn Gln Phe
305                 310                 315                 320

Leu Thr Trp Arg Ile Phe Phe Ala Ser Met Ile Ser Thr Phe Thr Leu
            325                 330                 335

Asn Phe Val Leu Ser Ile Tyr His Gly Asn Met Trp Asp Leu Ser Ser
            340                 345                 350

Pro Gly Leu Ile Asn Phe Gly Arg Phe Asp Ser Glu Lys Met Ala Tyr
            355                 360                 365

Thr Ile His Glu Ile Pro Val Phe Ile Ala Met Gly Val Val Gly Gly
370                 375                 380

Ile Leu Gly Ala Val Phe Asn Ala Leu Asn Tyr Trp Leu Thr Met Phe
385                 390                 395                 400

Arg Ile Arg Tyr Ile His Arg Pro Cys Leu Gln Val Ile Glu Ala Met
            405                 410                 415

Leu Val Ala Ala Val Thr Ala Thr Val Ala Phe Val Leu Ile Tyr Ser
            420                 425                 430

Ser Arg Asp Cys Gln Pro Leu Gln Gly Ser Ser Met Ser Tyr Pro Leu
            435                 440                 445

Gln Leu Phe Cys Ala Asp Gly Glu Tyr Asn Ser Met Ala Ala Ala Phe
450                 455                 460

Phe Asn Thr Pro Glu Lys Ser Val Val Ser Leu Phe His Asp Pro Pro
465                 470                 475                 480

Gly Ser Tyr Asn Pro Met Thr Leu Gly Leu Phe Thr Leu Val Tyr Phe
            485                 490                 495

Phe Leu Ala Cys Trp Thr Tyr Gly Leu Thr Val Ser Ala Gly Val Phe
            500                 505                 510

Ile Pro Ser Leu Leu Ile Gly Ala Ala Trp Gly Arg Leu Phe Gly Ile
            515                 520                 525

Ser Met Ser Tyr Leu Thr Gly Ala Ala Ile Trp Ala Asp Pro Gly Lys
530                 535                 540

Tyr Ala Leu Met Gly Ala Ala Ala Gln Leu Gly Gly Ile Val Arg Met
545                 550                 555                 560

Thr Leu Ser Leu Thr Val Ile Met Met Glu Ala Thr Ser Asn Val Thr
            565                 570                 575

Tyr Gly Phe Pro Ile Met Leu Val Leu Met Thr Ala Lys Ile Val Gly
            580                 585                 590

Asp Val Phe Ile Glu Gly Leu Tyr Asp Met His Ile Gln Leu Gln Ser
            595                 600                 605
```

```
Val Pro Phe Leu His Trp Glu Ala Pro Val Thr Ser His Ser Leu Thr
    610                 615                 620

Ala Arg Glu Val Met Ser Thr Pro Val Thr Cys Leu Arg Arg Arg Glu
625                 630                 635                 640

Lys Val Gly Ile Ile Val Asp Val Leu Ser Asp Thr Ala Ser Asn His
                645                 650                 655

Asn Gly Phe Pro Val Val Glu Asp Val Gly Asp Thr Gln Pro Ala Arg
                660                 665                 670

Leu Gln Gly Leu Ile Leu Arg Ser Gln Leu Ile Val Leu Leu Lys His
            675                 680                 685

Lys Val Phe Val Glu Arg Ser Asn Met Gly Leu Val Gln Arg Arg Leu
690                 695                 700

Arg Leu Lys Asp Phe Arg Asp Ala Tyr Pro Arg Phe Pro Pro Ile Gln
705                 710                 715                 720

Ser Ile His Val Ser Gln Asp Glu Arg Glu Cys Thr Met Asp Leu Ser
                725                 730                 735

Glu Phe Met Asn Pro Ser Pro Tyr Thr Val Pro Gln Glu Ala Ser Leu
                740                 745                 750

Pro Arg Val Phe Lys Leu Phe Arg Ala Leu Gly Leu Arg His Leu Val
            755                 760                 765

Val Val Asp Asn His Asn Gln Val Val Gly Leu Val Thr Arg Lys Asp
770                 775                 780

Leu Ala Arg Tyr Arg Leu Gly Lys Gly Gly Leu Glu Glu Leu Ser Leu
785                 790                 795                 800

Ala Gln Thr

<210> SEQ ID NO 13
<211> LENGTH: 2393
<212> TYPE: DNA
<213> ORGANISM: Homo sapiens
<220> FEATURE:
<221> NAME/KEY: CDS
<222> LOCATION: (1)..(2370)
<223> OTHER INFORMATION: ClC-7

<400> SEQUENCE: 13 gac gag gag gcg gcg ccg ctg ctg cgg agg acg gcg cgg ccc ggc ggg      48
Asp Glu Glu Ala Ala Pro Leu Leu Arg Arg Thr Ala Arg Pro Gly Gly
1               5                   10                  15 ggg acg ccg ctg ctg aac ggg gct ggg ccc ggg gct gcg cgc cag tca      96
Gly Thr Pro Leu Leu Asn Gly Ala Gly Pro Gly Ala Ala Arg Gln Ser
                20                  25                  30 cca cgt tct gcg ctt ttc cga gtc gga cat atg agc agc gtg gag ctg     144
Pro Arg Ser Ala Leu Phe Arg Val Gly His Met Ser Ser Val Glu Leu
            35                  40                  45 gat gat gaa ctt ttg gac ccg gat atg gac cct cca cat ccc ttc ccc     192
Asp Asp Glu Leu Leu Asp Pro Asp Met Asp Pro Pro His Pro Phe Pro
        50                  55                  60 aag gag atc cca cac aac gag aag ctc ctg tcc ctc aag tat gag agc     240
Lys Glu Ile Pro His Asn Glu Lys Leu Leu Ser Leu Lys Tyr Glu Ser
65                  70                  75                  80 ttg gac tat gac aac agt gag aac cag ctg ttc ctg gag gag gag cgg     288
Leu Asp Tyr Asp Asn Ser Glu Asn Gln Leu Phe Leu Glu Glu Glu Arg
                85                  90                  95 cgg atc aat cac acg gcc ttc cgg acg gtg gag atc aag cgc tgg gtc     336
Arg Ile Asn His Thr Ala Phe Arg Thr Val Glu Ile Lys Arg Trp Val
                100                 105                 110 atc tgc gcc ctc att ggg atc ctc acg ggc ctc gtg gcc tgc ttc att     384
```

```
Ile Cys Ala Leu Ile Gly Ile Leu Thr Gly Leu Val Ala Cys Phe Ile
        115                 120                 125 gac atc gtg gtg gaa aac ctg gct ggc ctc aag tac agg gtc atc aag        432
Asp Ile Val Val Glu Asn Leu Ala Gly Leu Lys Tyr Arg Val Ile Lys
130                 135                 140 ggc aat atc gac aag ttc aca gag aag ggc gga ctg tcc ttc tcc ctg        480
Gly Asn Ile Asp Lys Phe Thr Glu Lys Gly Gly Leu Ser Phe Ser Leu
145                 150                 155                 160 ttg ctg tgg gcc acg ctg aac gcc gcc ttc gtg ctc gtg ggc tct gtg        528
Leu Leu Trp Ala Thr Leu Asn Ala Ala Phe Val Leu Val Gly Ser Val
                165                 170                 175 att gtg gct ttc ata gag ccg gtg gct gct ggc agc gga atc ccc cag        576
Ile Val Ala Phe Ile Glu Pro Val Ala Ala Gly Ser Gly Ile Pro Gln
                180                 185                 190 atc aag tgc ttc ctc aac ggg gtg aag atc ccc cac gtg gtg cgg ctc        624
Ile Lys Cys Phe Leu Asn Gly Val Lys Ile Pro His Val Val Arg Leu
            195                 200                 205 aag acg ttg gtg atc aaa gtg tcc ggt gtg atc ctg tcc gtg gtc ggg        672
Lys Thr Leu Val Ile Lys Val Ser Gly Val Ile Leu Ser Val Val Gly
        210                 215                 220 ggc ctg gcc gtg gga aag gaa ggg ccg atg atc cac tca ggt tca gtg        720
Gly Leu Ala Val Gly Lys Glu Gly Pro Met Ile His Ser Gly Ser Val
225                 230                 235                 240 att gcc gcc ggg atc tct cag gga agg tca agc tca ctg aaa cga gat        768
Ile Ala Ala Gly Ile Ser Gln Gly Arg Ser Ser Ser Leu Lys Arg Asp
                245                 250                 255 ttc aag atc ttc gag tac ctc cgc aga gac aca gag aag cgg gac ttc        816
Phe Lys Ile Phe Glu Tyr Leu Arg Arg Asp Thr Glu Lys Arg Asp Phe
                260                 265                 270 gtc tcc gca ggg gct gcg gcc gga gtg tca gcg gcg ttt gga gcc ccc        864
Val Ser Ala Gly Ala Ala Ala Gly Val Ser Ala Ala Phe Gly Ala Pro
            275                 280                 285 gtg ggt ggg gtc ctg ttc agc ttg gag gag ggt gcg tcc ttc tgg aac        912
Val Gly Gly Val Leu Phe Ser Leu Glu Glu Gly Ala Ser Phe Trp Asn
        290                 295                 300 cag ttc ctg acc tgg agg atc ttc ttt gct tcc atg atc tcc acg ttc        960
Gln Phe Leu Thr Trp Arg Ile Phe Phe Ala Ser Met Ile Ser Thr Phe
305                 310                 315                 320 acc ctg aat ttt gtt ctg agc att tac cac ggg aac atg tgg gac ctg       1008
Thr Leu Asn Phe Val Leu Ser Ile Tyr His Gly Asn Met Trp Asp Leu
                325                 330                 335 tcc agc cca ggc ctc atc aac ttc gga agg ttt gac tcg gag aaa atg       1056
Ser Ser Pro Gly Leu Ile Asn Phe Gly Arg Phe Asp Ser Glu Lys Met
                340                 345                 350 gcc tac acg atc cac gag atc ccg gtc ttc atc gcc atg ggc gtg gtg       1104
Ala Tyr Thr Ile His Glu Ile Pro Val Phe Ile Ala Met Gly Val Val
            355                 360                 365 ggc ggt gtg ctt gga gca gtg ttc aat gcc ttg aac tac tgg ctg acc       1152
Gly Gly Val Leu Gly Ala Val Phe Asn Ala Leu Asn Tyr Trp Leu Thr
        370                 375                 380 atg ttt cga atc agg tac atc cac cgg ccc tgc ctg cag gtg att gag       1200
Met Phe Arg Ile Arg Tyr Ile His Arg Pro Cys Leu Gln Val Ile Glu
385                 390                 395                 400 gcc gtg ctg gtg gcc gcc gtc acg gcc aca gtt gcc ttc gtg ctg atc       1248
Ala Val Leu Val Ala Ala Val Thr Ala Thr Val Ala Phe Val Leu Ile
                405                 410                 415 tac tcg tcg cgg gat tgc cag ccc ctg cag ggg ggc tcc atg tcc tac       1296
Tyr Ser Ser Arg Asp Cys Gln Pro Leu Gln Gly Gly Ser Met Ser Tyr
                420                 425                 430
```

```
ccg ctg cag ctc ttt tgt gca gat ggc gag tac aac tcc atg gct gcg      1344
Pro Leu Gln Leu Phe Cys Ala Asp Gly Glu Tyr Asn Ser Met Ala Ala
        435                 440                 445 gcc ttc ttc aac acc ccg gag aag agc gtg gtg agc ctc ttc cac gac      1392
Ala Phe Phe Asn Thr Pro Glu Lys Ser Val Val Ser Leu Phe His Asp
450                 455                 460 ccg cca ggc tcc tac aac ccc ctg acc ctc ggc ctg ttc acg ctg gtc      1440
Pro Pro Gly Ser Tyr Asn Pro Leu Thr Leu Gly Leu Phe Thr Leu Val
465                 470                 475                 480 tac ttc ttc ctg gcc tgc tgg acc tac ggg ctc acg gtg tct gcc ggg      1488
Tyr Phe Phe Leu Ala Cys Trp Thr Tyr Gly Leu Thr Val Ser Ala Gly
                485                 490                 495 gtc ttc atc ccg tcc ctg ctc atc ggg gct gcc tgg ggc cgg ctc ttt      1536
Val Phe Ile Pro Ser Leu Leu Ile Gly Ala Ala Trp Gly Arg Leu Phe
            500                 505                 510 ggg atc tcc ctg tcc tac ctc acg ggg gcg gcg atc tgg gcg gac ccc      1584
Gly Ile Ser Leu Ser Tyr Leu Thr Gly Ala Ala Ile Trp Ala Asp Pro
        515                 520                 525 ggc aaa tac gcc ctg atg gga gct gct gcc cag ctg ggc ggg att gtg      1632
Gly Lys Tyr Ala Leu Met Gly Ala Ala Ala Gln Leu Gly Gly Ile Val
530                 535                 540 cgg atg aca ctg agc ctg acc gtc atc atg atg gag gcc acc agc aac      1680
Arg Met Thr Leu Ser Leu Thr Val Ile Met Met Glu Ala Thr Ser Asn
545                 550                 555                 560 gtg acc tac ggc ttc ccc atc atg ctg gtg ctc atg acc gcc aag atc      1728
Val Thr Tyr Gly Phe Pro Ile Met Leu Val Leu Met Thr Ala Lys Ile
                565                 570                 575 gtg ggc gac gtc ttc att gag ggc ctg tac gac atg cac att cag ctg      1776
Val Gly Asp Val Phe Ile Glu Gly Leu Tyr Asp Met His Ile Gln Leu
            580                 585                 590 cag agt gtg ccc ttc ctg cac tgg gag gcc ccg gtc acc tca cac tca      1824
Gln Ser Val Pro Phe Leu His Trp Glu Ala Pro Val Thr Ser His Ser
        595                 600                 605 ctc act gcc agg gag gtg atg agc aca cca gtg acc tgc ctg agg cgg      1872
Leu Thr Ala Arg Glu Val Met Ser Thr Pro Val Thr Cys Leu Arg Arg
610                 615                 620 cgt gag aag gtc ggc gtc att gtg gac gtg ctg agc gac acg gcg tcc      1920
Arg Glu Lys Val Gly Val Ile Val Asp Val Leu Ser Asp Thr Ala Ser
625                 630                 635                 640 aat cac aac ggc ttc ccc gtg gtg gag cat gcc gat gac acc cag cct      1968
Asn His Asn Gly Phe Pro Val Val Glu His Ala Asp Asp Thr Gln Pro
                645                 650                 655 gcc cgg ctc cag ggc ctg atc ctg cgc tcc cag ctc atc gtt ctc cta      2016
Ala Arg Leu Gln Gly Leu Ile Leu Arg Ser Gln Leu Ile Val Leu Leu
            660                 665                 670 aag cac aag gtg ttt gtg gag cgg tcc aac ctg ggc ctg gta cag cgg      2064
Lys His Lys Val Phe Val Glu Arg Ser Asn Leu Gly Leu Val Gln Arg
        675                 680                 685 cgc ctg agg ctg aag gac ttc cga gac gcc tac ccg cgc ttc cca ccc      2112
Arg Leu Arg Leu Lys Asp Phe Arg Asp Ala Tyr Pro Arg Phe Pro Pro
690                 695                 700 atc cag tcc atc cac gtg tcc cag gac gag cgg gag tgc acc atg gac      2160
Ile Gln Ser Ile His Val Ser Gln Asp Glu Arg Glu Cys Thr Met Asp
705                 710                 715                 720 ctc tcc gag ttc atg aac ccc tcc ccc tac acg gtg ccc cag gag gcg      2208
Leu Ser Glu Phe Met Asn Pro Ser Pro Tyr Thr Val Pro Gln Glu Ala
                725                 730                 735 tcg ctc cca cgg gtg ttc aag ctg ttc cgg gcc ctg ggc ctg cgg cac      2256
Ser Leu Pro Arg Val Phe Lys Leu Phe Arg Ala Leu Gly Leu Arg His
            740                 745                 750
```

```
ctg gtg gtg gtg gac aac cgc aat cag gtt gtc ggg ttg gtg acc agg    2304
Leu Val Val Val Asp Asn Arg Asn Gln Val Val Gly Leu Val Thr Arg
        755                 760                 765 aag gac ctc gcc agg tac cgc ctg gga aag aga ggc ttg gag gag ctc    2352
Lys Asp Leu Ala Arg Tyr Arg Leu Gly Lys Arg Gly Leu Glu Glu Leu
770                 775                 780 tcg ctg gcc cag acg tga ggcccagccc tgcccataat ggg                  2393
Ser Leu Ala Gln Thr
785

<210> SEQ ID NO 14
<211> LENGTH: 789
<212> TYPE: PRT
<213> ORGANISM: Homo sapiens

<400> SEQUENCE: 14
```

Asp Glu Glu Ala Ala Pro Leu Leu Arg Arg Thr Ala Arg Pro Gly Gly
 1               5                   10                  15

Gly Thr Pro Leu Leu Asn Gly Ala Gly Pro Gly Ala Ala Arg Gln Ser
                20                  25                  30

Pro Arg Ser Ala Leu Phe Arg Val Gly His Met Ser Ser Val Glu Leu
            35                  40                  45

Asp Asp Glu Leu Leu Asp Pro Asp Met Asp Pro Pro His Pro Phe Pro
        50                  55                  60

Lys Glu Ile Pro His Asn Glu Lys Leu Leu Ser Leu Lys Tyr Glu Ser
 65                 70                  75                  80

Leu Asp Tyr Asp Asn Ser Glu Asn Gln Leu Phe Leu Glu Glu Glu Arg
                85                  90                  95

Arg Ile Asn His Thr Ala Phe Arg Thr Val Glu Ile Lys Arg Trp Val
            100                 105                 110

Ile Cys Ala Leu Ile Gly Ile Leu Thr Gly Leu Val Ala Cys Phe Ile
        115                 120                 125

Asp Ile Val Val Glu Asn Leu Ala Gly Leu Lys Tyr Arg Val Ile Lys
    130                 135                 140

Gly Asn Ile Asp Lys Phe Thr Glu Lys Gly Gly Leu Ser Phe Ser Leu
145                 150                 155                 160

Leu Leu Trp Ala Thr Leu Asn Ala Ala Phe Val Leu Val Gly Ser Val
                165                 170                 175

Ile Val Ala Phe Ile Glu Pro Val Ala Ala Gly Ser Gly Ile Pro Gln
            180                 185                 190

Ile Lys Cys Phe Leu Asn Gly Val Lys Ile Pro His Val Val Arg Leu
        195                 200                 205

Lys Thr Leu Val Ile Lys Val Ser Gly Val Ile Leu Ser Val Val Gly
    210                 215                 220

Gly Leu Ala Val Gly Lys Glu Gly Pro Met Ile His Ser Gly Ser Val
225                 230                 235                 240

Ile Ala Ala Gly Ile Ser Gln Gly Arg Ser Ser Ser Leu Lys Arg Asp
                245                 250                 255

Phe Lys Ile Phe Glu Tyr Leu Arg Arg Asp Thr Glu Lys Arg Asp Phe
            260                 265                 270

Val Ser Ala Gly Ala Ala Gly Val Ser Ala Phe Gly Ala Pro
        275                 280                 285

Val Gly Gly Val Leu Phe Ser Leu Glu Glu Gly Ala Ser Phe Trp Asn
    290                 295                 300

Gln Phe Leu Thr Trp Arg Ile Phe Phe Ala Ser Met Ile Ser Thr Phe

-continued

```
            305                 310                 315                 320
Thr Leu Asn Phe Val Leu Ser Ile Tyr His Gly Asn Met Trp Asp Leu
                    325                 330                 335
Ser Ser Pro Gly Leu Ile Asn Phe Gly Arg Phe Asp Ser Glu Lys Met
                340                 345                 350
Ala Tyr Thr Ile His Glu Ile Pro Val Phe Ile Ala Met Gly Val Val
            355                 360                 365
Gly Gly Val Leu Gly Ala Val Phe Asn Ala Leu Asn Tyr Trp Leu Thr
        370                 375                 380
Met Phe Arg Ile Arg Tyr Ile His Arg Pro Cys Leu Gln Val Ile Glu
385                 390                 395                 400
Ala Val Leu Val Ala Ala Val Thr Ala Thr Val Ala Phe Val Leu Ile
                    405                 410                 415
Tyr Ser Ser Arg Asp Cys Gln Pro Leu Gln Gly Gly Ser Met Ser Tyr
                420                 425                 430
Pro Leu Gln Leu Phe Cys Ala Asp Gly Glu Tyr Asn Ser Met Ala Ala
            435                 440                 445
Ala Phe Phe Asn Thr Pro Glu Lys Ser Val Val Ser Leu Phe His Asp
        450                 455                 460
Pro Pro Gly Ser Tyr Asn Pro Leu Thr Leu Gly Leu Phe Thr Leu Val
465                 470                 475                 480
Tyr Phe Phe Leu Ala Cys Trp Thr Tyr Gly Leu Thr Val Ser Ala Gly
                    485                 490                 495
Val Phe Ile Pro Ser Leu Leu Ile Gly Ala Ala Trp Gly Arg Leu Phe
                500                 505                 510
Gly Ile Ser Leu Ser Tyr Leu Thr Gly Ala Ala Ile Trp Ala Asp Pro
            515                 520                 525
Gly Lys Tyr Ala Leu Met Gly Ala Ala Ala Gln Leu Gly Gly Ile Val
        530                 535                 540
Arg Met Thr Leu Ser Leu Thr Val Ile Met Met Glu Ala Thr Ser Asn
545                 550                 555                 560
Val Thr Tyr Gly Phe Pro Ile Met Leu Val Leu Met Thr Ala Lys Ile
                    565                 570                 575
Val Gly Asp Val Phe Ile Glu Gly Leu Tyr Asp Met His Ile Gln Leu
                580                 585                 590
Gln Ser Val Pro Phe Leu His Trp Glu Ala Pro Val Thr Ser His Ser
            595                 600                 605
Leu Thr Ala Arg Glu Val Met Ser Thr Pro Val Thr Cys Leu Arg Arg
        610                 615                 620
Arg Glu Lys Val Gly Val Ile Val Asp Val Leu Ser Asp Thr Ala Ser
625                 630                 635                 640
Asn His Asn Gly Phe Pro Val Val Glu His Ala Asp Asp Thr Gln Pro
                    645                 650                 655
Ala Arg Leu Gln Gly Leu Ile Leu Arg Ser Gln Leu Ile Val Leu Leu
                660                 665                 670
Lys His Lys Val Phe Val Glu Arg Ser Asn Leu Gly Leu Val Gln Arg
            675                 680                 685
Arg Leu Arg Leu Lys Asp Phe Arg Asp Ala Tyr Pro Arg Phe Pro Pro
        690                 695                 700
Ile Gln Ser Ile His Val Ser Gln Asp Glu Arg Glu Cys Thr Met Asp
705                 710                 715                 720
Leu Ser Glu Phe Met Asn Pro Ser Pro Tyr Thr Val Pro Gln Glu Ala
                    725                 730                 735
```

```
Ser Leu Pro Arg Val Phe Lys Leu Phe Arg Ala Leu Gly Leu Arg His
            740                 745                 750

Leu Val Val Val Asp Asn Arg Asn Gln Val Val Gly Leu Val Thr Arg
            755                 760                 765

Lys Asp Leu Ala Arg Tyr Arg Leu Gly Lys Arg Gly Leu Glu Glu Leu
        770                 775                 780

Ser Leu Ala Gln Thr
785
```

ANIMAL MODEL AND CELL-LINE EXPRESSING MODIFIED CHLORINE CHANNEL

This application is a continuation of PCT/DK02/00038 (WO 02/059612) as filed on Jan. 17, 2002 which application claims benefit to German (DE) patent application 101 02 977.2 as filed on Jan. 23, 2001. The disclosures of the PCT/DK02/00038 and 101 02 977.2 applications are incorporated by reference.

The present invention relates to a test system for the identification and testing of active compounds, which act on synaptic transmission (active compounds for treatment of neuronal diseases), which influence endo/exocytosis, which influence processing of proteins and in particular of active compounds which can be used for treatment of osteoporosis or Pagers disease, for treatment of neurological and neuromuscular diseases and other nerve diseases or as psychotropic pharmaceuticals. The invention furthermore relates to a non-human mammal, preferably a rodent, in which one or more chloride channels from the group consisting of CIC-3, CIC-4, CIC-6 and CIC-7 are not expressed or are expressed non-functionally, and to somatic cell lines which are derived, for example, from such an animal, and to the use thereof for the identification and testing of substances which are suitable for influencing in their activity, in particular inhibiting or activating, chloride channels, in particular CIC, CIC-3, CIC-5, CIC-6 and/or CIC-7.

Osteoporosis is a disease in which increased degradation of bone occurs, leading to fragility. Osteoporosis is widespread in elderly persons, in particular in elderly women (of hormonal origin). For this reason, sex hormones, which can indeed stop the process of bone degradation, but in most cases have serious undesirable side effects, are often administered to elderly female patients. Specific osteoporosis; medicaments have not hitherto been developed.

In the context of the present invention, it has now been found, surprisingly, that mutations in the nucleic acid sequence encoding the CIC-7 protein (chloride channel CIC-7) leads to the expression of a non-functional protein, or completely suppresses expression of such protein thereby causing a very severe form of osteopetrosis in mice. On the basis of these surprising results, it was found that patients with severe juvenile osteopetrosis also have mutations in the CIC-7 gene.

The chloride channel CIC-7 is a predominantly intracellular chloride channel present in late endosomes and lysosomes. CIC-7 is expressed ubiquitously, and in particular also occurs in osteoclasts, the bone-degrading cells. Mutations that lead to the expression of a non-functional CIC-7 protein or that completely suppress expression (called "knock-out" or "KO" in the following), prevent osteoclasts from being able to degrade bone. More detailed studies have shown that GIC-7 is incorporated together with the proton pump into the so-called "ruffled membrane". The ruffled membrane borders the resorption lacunae and acid equivalents are transported into the resorption lacunae via a proton-pump, and the electroneural transport of HCl into the lacunae is ensured by a parallel chloride conductance carried by CIC-7. An acidic pH in the lacunae is essential or the bone degradation. If an appropriate chloride conductance is absent, the proton pump cannot pump effectively, with the consequence that osteoclasts cannot acidify the resorption lacunae and cannot destroy the bone.

By knock-out of CIC-7, severe degeneration of the retina furthermore occurs, and neurodegeneration in the central nervous system (CNS) is moreover observed. These observations can be attributed to the fact that the late-endosomal and lysosomal acidification and degradation is impaired in many tissues by CIC-7 knock-out.

In the context of the present invention, it has also been found that chloride channels of the CLC gene family are also involved in the acidification of synaptic vesicles. This has been demonstrated, for example, by knock-out of the CIC-3 channel. With this knock-out, changes in synaptic transmission in the central nervous system and neuronal degeneration occur. It has furthermore been found that other CIC channels, such as CIC-4 and CIC-7, are present in synaptic vesicles. Synaptic vesicles take up neurotransmitters, which are then released into the synaptic gap via exocytosis and, thus, modulate (stimulate or inhibit) the downstream nerve cell. The uptake of neurotransmitters into synaptic vesicles is driven by the pH gradient and the potential gradient across the membrane of the synaptic vesicles (cf. literature references (62)-(67)), so that the activity of chloride channels in synaptic vesicles influences signal transduction in the nervous system.

By the studies set up in the context of the present invention, it is now possible to provide a test system, which enables identification and testing of substances that inhibit one or more chloride channels from the group consisting of CIC-1, CIC-2, CIC-Ka, CIC-Kb, CIC-3, CIC-4, CIC-5, CIC-6 and/or CIC-7—in particular the predominantly intracellular chloride channels CIC-3, CIC-4, CIC-5, CIC-6 and/or CIC-7- or of otherwise influencing them in activity, i.e. for example activating them or modifying their regulation. In particular, for the first time a test system and a process are provided for the identification and testing of substances, which (completely or partly) inhibit the chloride channel CIC-7, in particular substances which are suitable for treatment of osteoporosis or Paget's disease. Such a test system also enables identification of substances that influence neuronal signal transduction, and are therefore suitable for treatment of neuronal diseases.

The invention is based on the consideration that a (partial) inhibition of the CIC-7 chloride channel inhibits osteoclast function and, therefore, counteracts bone degradation. Research along the same line is being conducted in the pharmaceutical industry, where effective inhibitors of the proton pump are being searched for. By the present knowledge, it is now possible for the first time to identify substances which act specifically on the CIC-7 chloride channel and cause partial or complete inhibition or activate the channel or modify regulation thereof. A total KO of CIC-7 also Influences other tissue and causes e.g. degeneration of the retina and degeneration of the CNS. Therefore pharmacological inhibition of CIC-7 (i.e. by administration of CIC-7 inhibitors) could potentially have similar effects. This problem can be solved on the one hand by only partial inhibition of the channel, and on the other hand by using active compounds or pharmaceuticals which do not reach undesirable target organs (i.e. eye and brain) (e.g. because of the blood-brain barrier). Further, as CIC-7 exerts its role in bone degradation in the plasma membrane of osteoclasts, but is in intracellular vesicles in neurons, drugs may be designed that do not enter cells and therefore act specifically on osteoclast-expressed CIC-7.

The invention is furthermore based on the assumption that synaptic transmission in the nervous system can be influenced by an inhibition or stimulation of chloride channels. Interventions into synaptic transmission are a widely used principle of the pharmacology for treatment of neurological and neuromuscular diseases. Thus drugs that influence the corresponding uptake of transporters into synaptic vesicles or that influence re-uptake of the secreted neurotransmitter from the synaptic cleft into the cell are employed. Uptake of neurotransmitters into the synaptic vesicles takes place via transporters located in the membrane thereof, which in general are coupled with and driven by the electrochemical gradients for protons across the vesicle membrane (cf. publications (81) and (82)). If these gradients are changed, the uptake of transmitters are modified, in some cases differentially. On the one hand, particular CLC channels are possibly present only in particular subpopulations of nerve cells or synaptic vesicles (e.g. for particular neurotransmitters), and on the other hand the electrochemical-gradient for protons consists of two components ($\Delta$pH and $\Delta\psi$), to which the various transporters are coupled. The uptake of acetylcholine is thus chiefly driven via the pH gradient, while the uptake of glutamate is chiefly driven by the electrical potential $\Delta\psi$.

The electrochemical gradient for protons in synaptic vesicles is built up by the proton pump in conjunction with chloride channels. The presence of a chloride conductivity reduces the electrical component $\Delta\psi$ of the gradient and increases the $\Delta$pH component. Inhibition of a chloride channel in synaptic vesicles thus reduces $\Delta$pH, but increases $\Delta\psi$ as a result e.g. the uptake of acetylcholine is reduced but the uptake of glutamate is increased, provided that the channel occurs on both vesicle types. According to a particular embodiment, conversely, a specific stimulation of individual chloride channels is also envisaged. This would result e.g. in a reduction in glutamate uptake and an increase in acetylcholine uptake.

In addition to the possibility of modulating the concentration of neurotransmitters in synaptic vesicles, such substances can also influence the transport of the vesicles within the cell, e.g. also endo- and exocytosis. This follows from the observation that in the event of CIC-5 KO, endocytotic trafficking is is greatly reduced (cf. (8)), and from the fact that the endocytotic and exocytotic pathway can be impaired considerably by reducing the vesicular pH (cf. publications (69) to (74)).

Substances, which influence and in particular inhibit, the activity of the CIC chloride channels CIC-3, CIC-4, CIC-6 and/or CIC-7, which occur predominantly intracellularly, are thus suitable as therapeutic agents for neurological, and neuromuscular diseases and other nerve diseases and, in the case of CIC-7, for osteoporosis, Paget's disease, and other bone-degrading diseases. In the context of the invention, these channel proteins are therefore useful as molecular targets in order to discover and develop substances for the treatment of such diseases.

Several assays are suitable as methods for discovering and testing such substances. According to one embodiment of the invention, binding of the substances to the target molecule is tested by methods well-known to the skilled person. For this, the channel proteins are expressed endogenously, e.g. by osteoclasts, or heterologously, e.g. by bacteria, yeasts or mammalian cells, and purified. Appropriate processes are well-known to the skilled person. In a preferred embodiment of the invention binding of the substances to the proteins can be investigated by well-known methods of fluorescence correlation spectroscopy and fluorescence intensity distribution analysis (cf. references (85) to (88)). In another preferred embodiment, the measurement is carried out by similarly well-known methods of plasmon resonance measurement (cf. references (89) to (94)). In yet another embodiment, the binding of ligands to the CIC channels CIC3, CIC-4, CIC-6 and/or CIC-7 is measured by the use of labeled ligands, the label being radioactive, fluorescent or any other label that can be identified specifically when compared the same un-labelled ligand. Methods are well-known to the person skilled in the art.

Another preferred method of this invention for the identification of substances which act on the chloride channels CIC-3, CIC-4, CIC-6 and/or CIC-7 comprises test systems in which the corresponding channel protein is expressed functionally, either endogenously or heterologously. Such systems are also appropriate for testing the substances found in the above binding processes for functional effects. In this case, measurement is carried out via the function of the channel protein, which changes either currents, potentials or pH values in particular systems, which then either are measured directly, or their effect on the detection systems is measured. In another preferred method of this invention measurements as above are not performed on the wild-type form of the channel, but on a mutant channel protein that may for instance reside in a different compartment (e.g. plasma membrane) that is easier to study.

In another preferred method of this invention, the structure of CIC-3, CIC-4, CIC-6, and/or CIC-7 may be used to identify or optimize substances binding to the channel protein by molecular modeling.

Another preferred method of this Invention for the identification of substances which act on the chloride channels CIC-3, CIC-4, CIC-6 and/or CIC-7 comprises test systems in which the corresponding channel protein is expressed functionally, but the other channel proteins are either present to a lesser degree or are not present at all. Such systems are also appropriate for testing the substances found in the above binding processes for functional effects. In this case, measurement is carried out via the function of the channel protein, which changes either currents, potentials or pH values in particular systems, which then either are measured directly, or their effect on the detection systems is measured.

In a preferred embodiment of the invention, the activity of the substance on a channel CIC-x (x=3, 4, 6 or 7) is measured on cells or preparations derived therefrom (such as membrane preparations or vesicles) which exclusively or preferentially (predominantly) express only the channel CIC-x (e.g. CIC-7 in the search for osteoporosis medicaments).

The specificity is tested by measuring the activity of test substances, for example, on cells which exclusively or preferentially (predominantly) express only the CIC-7 channel. These cells or cell lines are obtained, for example, by isolation of the is germ cells and somatic cells, which contain nucleic acid sequences encoding chloride channels, from non-human mammals, preferably rodents (in; particular mice). In these cells as many as possible of the chloride channel encoding nucleic acid genes—with the exception of the chloride channel for which a specific inhibitor is being searched for—are modified by mutation, truncation, complete deletion and/or partial deletion such that the particular chloride channels are not expressed or are expressed, non-functionally. Non-functionally in this context means that the the chloride channel protein is expressed such that the transport function of the chloride channel is reduced or suppressed completely. These genetic or genetically engineered modifications are also called knock-out. Corresponding genetically modified mice (as an example of a non-human mammal) are also called knock-out mice or KO mice. Natural mutants, for example, exist as knock-outs of the CIC-1 channel in mice and humans, i.e. a non-functional or absent expression of the CIC-1 channel occurs naturally in a certain percentage of the population, which leads to myotonia congenita. In the case of a knockout of the CIC-K1 channel or of the CIC-KB channel, diabetes Insipidus (in mice) or Bartter's syndrome (in humans) occurs. A knock-out of CIC-5 in humans leads to Dent's disease.

The specificity of substances binding to or modifying CIC channels can of course also be measured by other methods, for example on the isolated channel protein, which can be obtained e.g. by over-expression. Appropriate processes for cloning and expression of the nucleic acid sequence encoding the corresponding channel protein are known in the greatest of detail to the skilled person. The specificity can furthermore also be determined directly using suitable assays, such as e.g. the "pit assay" (see below), which are well-known to the skilled person.

The experimentally generated knock-out of ion channels and in particular of chloride channels is well-known to the skilled person and is described, for example, in publications (1) to (8) cited in the appendix. It is furthermore known that numerous modifications of the nucleic acid sequences, which code for chloride channels lead to a lack of function or expression of the proteins (cf. publications (9) to (24)). The general structural build-up and the transmembrane topology of the chloride channels is shown in the diagram in FIG. 1. For example, individual point mutations in domains D3 to D5 already lead to disturbances in or a lack of expression or to expression of a protein which has no chloride channel properties. The same effect can be achieved by truncation in the region of domains D10 to D12 or generally by truncation in transmembrane-spanning domains. The gene, i.e. the nucleic acid sequence which codes for the chloride channel, can of course also be deleted completely or replaced by a nucleic acid sequence, which codes for another protein, or the promoter region which controls the gene expression can be mutated. The aim of the genetic modification is to suppress the protein expression or to effect non-functional expression of the protein. Alternatively, a so-called knock-down with which the genetic engineering modifications lead merely to a restriction in the chloride is channel function, without completely suppressing the transport properties, is also possible. Such knock-down strategies are well-known to the skilled person and include e.g. antisense strategies or ribozyme strategies, i.e. knock-down using antisense oligonucleotides and ribozymes, but are not limited to these. Methods used in the knock-down are described in more detail in publications (25) to (36) cited in the appendix, to which reference is expressly made here.

In the context of the present invention, it is possible to use both somatic cell lines, which are produced from a genetically modified non-human mammal, (rodent, in particular mouse) and those cell lines in which the expression of the corresponding channels CICxxx has subsequently been reduced or abolished by genomic mutations of the somatic cell line and/or the expression of the channels has been down-regulated by other processes, such as e.g. via antisense technology or ribozyme or RNAi strategies. This down-regulation or reduction of expression can in particular also be inducible and, thus, prevent or alleviate problems of cell survival and other problems, which can arise from switching off several chloride channels at the same time. These cell lines can also be of human origin.

The identification and testing of substances for chloride channel-specific actions preferably starts from genetically-modified non-human mammals or from cell lines in which preferably two or three chloride channels are not expressed or are expressed non-functionally. In the case of the chloride channel CIC-7, the expression of this chloride channel should not be impaired, so that a knock-out or knock-down of one or more other chloride channels, for example from the group consisting of CIC-3, CIC-4, CIC-5 and CIC-6, must take place. Corresponding conditions also apply if substances which act specifically on another channel are to be identified and tested. Thus, for a test with respect to CIC-4 e.g. cell lines which express only the CIC-4 channel must be established. Testing of the substances can be carried out either directly on these cells or on preparations obtained from these cells, such as e.g. vesicles, membrane preparations, in particular synaptic vesicle preparations, or purified proteins. Processes for the isolation of these preparations are well-known to the skilled person.

The specificity of the action against a particular CIC chloride channel is tested using on the one hand, as described for discovering the substances, cell lines which chiefly or exclusively contain only this particular chloride channel in the intracellular compartments tested, or using the abovementioned preparations derived therefrom. Substances which show the expected effect in these cell lines or on preparations derived therefrom are then tested on other cell lines or preparations derived therefrom which do not have this channel. If they are specific, they should have no effect on these cell lines. More specific assays follow, depending on the channel: If e.g. the effect on the CIC-7 channel is to be tested with respect to osteoporosis, cultured wild-type (WT) osteoclasts can be tested in a "pit assay" (cf. publications (52) to (58)) on dentine, ivory, bone or other suitable substrates and, for example, the formation of holes in the substrate can be investigated or the acidification of the resorption lacunae can be investigated with appropriate dyes (e.g. acridine orange) (cf. publications (59) to (61)).

If inhibition of chloride channels of synaptic vesicles (such as e.g. CIC-3) is aimed at, the acidification of purified synaptic vesicles in suspension can be measured with dyes in the next step (cf. publications (62) to (64)). An inhibition of the channel should manifest itself in an inhibition of the rate of acidification, and the specificity can be checked by isolating synaptic vesicles from the corresponding KO mouse. The substance should have no effect on the rate of acidification of synaptic vesicles isolated from those mice. In further steps, the specificity for particular types of synaptic vesicles can be tested by determining the uptake of (e.g. radioactively labelled) neurotransmitters in synaptic vesicles in the presence and absence of the substance. The corresponding methods are well-known to the skilled person (cf. e.g. publications (65) to (68)).

Somatic cell lines can be isolated from various tissues of KO mice, and the material is obtained in a form which is as sterile as possible and is introduced, either in the native form or preferentially after enzymatic digestion, into appropriate cell culture containers (e.g. dishes) together with nutrient media (e.g. Dulbecco's MEM, preferably at least initially with added antibiotics) and incubated at 37° C. and 5% $CO_2$. The cells are multiplied with standard techniques of cell culture, according to a particular embodiment of the invention the cell line being immortalized by transfection with appropriate genes (e.g. SV40 largeT antigen, or telomerase) (cf. publications (37) to (39)). As an alternative, KO mice can be crossed with a mouse strain which expresses an appropriate immortalization gene (such as e.g. the immorto mouse, cf. publications (40) to (42), and also other mice (cf. publication (43)) which express these genes, possibly under the control of an inducible promoter).

In particular, these cell lines can be further developed as a test system by transfecting them with appropriate constructs which express proteins which serve directly or indirectly as an indicator for the measurement method. For example, it is possible to express chimaeric proteins which, on the basis of particular protein sequence signals, are diverted specifically into particular compartments. The other part of the chimaeric unit contains either an appropriate indicator protein directly, such as e.g. pH-sensitive fluorescent proteins, such as particular GFP mutants (cf. publications (44) to (46)), or binding sites for diverting indicator substances, such as e.g. antibodies (cf. publication (49)) or biotin-coupled dyes (cf. publication (47)) into these compartments (cf. (44) to (51)).

A particular embodiment of the invention thus relates to the use of the abovementioned non-human mammals or somatic cell lines (of human or non-human origin) for identification of substances which act on synaptic transmission. A test system and a process are provided for the first time for the identification and testing of substances which inhibit or otherwise influence in activity (i.e. for example activate or modify its/their regulation) the chloride channel CIC-3, CIC-4, CIC-6 and/or CIC-7, in particular substances which are suitable for treatment of neurological and neuromuscular diseases and other nerve diseases or as psychotropic pharmaceuticals.

Compounds that may be useful for the treatment of osteoporosis may be distinguished from other compounds by their effectiveness in influencing CIC-7. That is to say, for example, active compounds against CIC-3 (which occurs on synaptic vesicles) will not interfere with the extracellular acidification of osteoclasts. On the other hand, substances which act on CIC-7 can optionally be modified such that they cannot cross the blood-brain barrier and therefore cannot act in the CNS. Such methods are well-known to the skilled person. It is also conceivable that substances are diverted (directed or sorted) specifically into certain neurone groups (e.g. by binding to specific surface receptors), or the substances are first metabolized to the active substance via specific enzymatic activities present in specific subsets of neurones.

A test of the specificity can be carried out, as mentioned above, on the one hand with the aid of appropriate cell lines which express only particular channel types, on preparations derived therefrom (see above) or in specific test systems, such as osteoclasts in culture, or on synaptic vesicle preparations from WT and KO animals.

The present invention relates in particular to a nucleic acid sequence which codes for a protein from the group consisting of the chloride channels CIC-3, CIC-4, CIC-6 and CIC-7, wherein the nucleic acid sequence is modified by mutation, truncation or complete or partial deletion.

The invention furthermore relates to a genetically modified non-human mammal, the gametes and somatic cells of which contain nucleic acid sequences which code for a protein from the group consisting of the chloride channels CIC-1, CIC-2, CIC-Ka, CIC-Kb, CIC-3, CIC-4, CIC-5, CIC-6 and/or CIC-7, wherein the nucleic acid sequence(s) which code(s) for CIC-3, CIC-4, CIC-6 and/or CIC-7 is (are) modified (with respect to the naturally occurring nucleic acid sequence) by mutation, truncation and/or complete or partial deletion.

According to a preferred embodiment of the invention the genetically modified, non-human mammal additionally contains the nucleic acid sequence(s) which code(s) for CIC-1, CIC-2, CIC-Ka, CIC-Kb and/or CIC-5 and which is (are) modified by mutation, truncation and/or complete or partial deletion.

According to the invention, somatic cell lines which do not express one or more chloride channels from the group consisting of CIC-1, CIC-2, CIC-Ka, CIC-Kb, CIC-3, CIC-4, CIC-5, CIC-6 and CIC-7 are established or derived from the mammal, which in particular is a rodent and particularly preferably a mouse. As already described, it is also possible to derive from these non-human mammals preparations, such as e.g. vesicle and other membrane preparations, in particular also synaptic vesicle preparations, which have an appropriate expression pattern in respect of the chloride channels and are therefore just as suitable as the KO animals or cell lines as such.

The invention furthermore relates to somatic cell lines in which either the expression of the chloride channels CIC-1, CIC-2, CIC-Ka, CIC-Kb, CIC-3, CIC-4, CIC-5, CIC-6 and CIC-7, in particular from the group consisting of CIC-3, CIC-4, CIC-6 and CIC-7, is reduced by genomic mutations of the somatic cell line and/or the expression of the channels is down-regulated by other processes, such as e.g. via antisense technology or ribozyme strategies. This down-regulation can in particular also be inducible in order to prevent or alleviate problems with the vitality of the cells and other problems which can arise by switching off several chloride channels at the same time.

The abovementioned cell lines can also be of human origin.

The invention furthermore relates to the use of a genetically modified, non-human mammal, the germ cells and somatic cells of which contain nucleic acid sequences which code for a protein from the group consisting of the chloride channels CIC-1, CIC-2, CIC-Ka, CIC-Kb, CIC-3, CIC-4, CIC-5, CIC-6 and/or CIC-7, wherein one or more of these nucleic acid sequences is/are modified (with respect to the naturally occurring nucleic acid sequence) by mutation, truncation and/or complete or partial deletion, for the identification and testing of substances which are suitable for inhibiting one or more chloride channels.

Mammals in which one or more of the nucleic acid sequences which code for proteins from the group consisting of the chloride channels CIC-1, CIC-2, CIC-Ka, CIC-Kb, CIC-3, CIC-4, CIC-5, CIC-6 and CIC-7 is modified (with respect to the naturally occurring nucleic acid sequence) by mutation, truncation and/or complete or partial deletion, in each case one of the sequences which code for CIC-7, CIC-3, CIC-3 or CIC-6 not being modified, so that this chloride channel is expressed normally, i.e. functionally.

Instead of mammals, the abovementioned cell lines (human and non-human) or preparations derived therefrom (see above) can also be used.

Finally, the invention relates to a process for the identification and testing of substances which are suitable for inhibiting or otherwise influencing in its/their activity, i.e. for example activating or modifying their regulation, one or more chloride channels from the group consisting of CIC-3, CIC-4, CIC-6 and CIC-7. In this process, on cell lines or cells (or preparations derived therefrom, in particular membrane preparations, such as vesicles; see above) which express only one chloride channel from the group consisting of CIC-3, CIC-4, CIC-6 and CIC-7, the luminal pH of the compartments which express the channel and/or the potential across the membrane enclosing the channel is determined. These cell lines or cells are then brought into contact with the substances to be tested, and the luminal pH of the compartment, which expresses the channel and/or the potential across the membrane enclosing the channel is determined again. A change in one or both of the physical parameters means that the test substance influences the chloride channel in question. An increase in the pH means that it is a substance which (partially) hinders or (partially) inhibits the chloride channel. Lowering of the pH indicates an acidification of the compartment and therefore a substance which activates the chloride channel. Measurement of an increase in the potential likewise means that it is a substance which (partly) hinders or (partly) inhibits the chloride channel. Lowering of the potential indicates a substance. Which activates the chloride channel. The activity of a substance in respect of its ability to influence the chloride channel in question is higher the lower the concentration of substance that has to be added in order to effect a change in the physical parameter or parameters.

The process according to the invention is based on the principle that a change in the activity of intracellular chloride channels can change the luminal pH of the compartments which express them and/or the potential across the membrane enclosing them. Chloride channels allow a charge compensation for the proton pumps occurring in the same vesicles (e.g. of the endo- or exocytotic pathway), which has the effect of a higher pump output and therefore a higher acidification of the compartment. At the same time, they lower the electrical potential across this membrane. An inhibition or switching off of the chloride channels would therefore result in a reduced acidification and a higher electrical potential, but a stimulation of their activity would result in an increased acidification and a lowering of the electrical potential. In the present invention the effect of the substances to be tested on the corresponding chloride channels is measured indirectly via one or more effects of the changed acidification and/or potential of intracellular compartments. In order to identify specific substances for a particular channel type, in the preferred use the compartments measured should as far as possible contain only one chloride channel against which the test is being carried out. The chloride channel specificity is demonstrated by carrying out control studies on cell lines which express another channel. If the compartments express more than one chloride channel, further measurements must be carried out on other KO cell lines or mice, as described above.

The process according to the invention for the identification and testing of substances which are suitable for inhibiting one or more chloride channels from the group consisting of CIC-3, CIC-4, CIC-5, CIC-6 and/or CIC-7 is characterized in that a) on cells which express only one or chiefly or predominantly only one of the chloride channels mentioned, the luminal pH of the compartments which express the channel and/or the potential across the membrane enclosing the channel is measured, b) the cells are brought into contact with a substance and c) the luminal pH of the compartments which express the channel and/or the potential across the membrane enclosing the channel is measured again on the cells, the difference between the pH and/or the membrane potential before and after addition of the substance determining the activity of the substance.

As already mentioned, one process variant consists of direct measurement of the pH of intracellulular organelles or measurement of the cell effects which occur as a result of the change in pH. Several methods are possible for measurement of the pH. There are, for example, dyes of which the fluorescence is pH-dependent or which concentrate selectively in compartments with particular pH values when the cells are Incubated with them or their precursor stages (examples: acridine orange, Lysotracker and other dye from Molecular Probes, Eugene, Oreg., USA). A higher specificity for particular compartments can be achieved e.g. by endocytotic uptake of dyes (staining of, endocytotic compartments, depending on the uptake time, early or late up to lysosomal compartments; cf. e.g. publications (71), (75), (76)). An even higher specificity for particular compartments can be achieved by binding the dyes via coupled molecular groups (such as e.g. specific antibodies or biotin) to particular target molecules, which occur in an increased amount or exclusively in particular compartments, i.e. which are expressed in the cell line (e.g. by permanent transfection), the cell line being brought into contact with the dye. These target molecules can also be prepared via molecular cell biology techniques, e.g. by fusing a target control signal, which directs the molecule into a particular compartment via an appropriate machinery of the cell, to a corresponding binding motif (e.g. epitope for antibodies or avidin) by a molecular biology method and then expressing the construct in the corresponding cell line used for testing the substances. Using such techniques, it is possible to examine and measure predominantly or even very specifically only those compartments that contain the channel of interest The accumulation of particular substances In compartments with a particular pH (such as e.g. acridine orange or Lysotracker from Molecular Probes) or indirect tests in which pH-dependent reactions in the compartments are utilized to produce indicator substances (e.g. by pH-dependent proteolytic cleavage), which are then easy to detect (e.g. using dyes (cf. publications (95) and (96)), although the detection is not limited thereto), are also used e.g. as a further technique for pH measurement.

Alternatively or in addition, the membrane potential in these compartments can be measured, e.g. via potential-sensitive dyes (cf. e.g. publication (67)). Alternatively, protein-coded potential sensors (cf. e.g. publication (77)), which are possibly also diverted or sorted specifically, are also possible here.

The present invention provides for the first time a test system with which active compounds which are suitable for the preparation of medicaments for treatment of osteoporosis or Paget's disease or for the preparation of medicaments for treatment of neurological and neuromuscular diseases and other nerve diseases or for the preparation of psychotropic pharmaceuticals can be identified and tested. The invention thus also relates to the use of substances, which completely or partly inhibit the chloride channel CIC-7 for the preparation of medicaments for treatment of osteoporosis or Pager's disease, and to the use of substances which completely or partly inhibit the chloride channel CIC-3, CIC-4, CIC-6 and/or CIC-7 for the preparation of medicaments for treatment of neurological and neuromuscular diseases and other nerve diseases or of psychotropic pharmaceuticals. The invention furthermore relates to pharmaceutical compositions (medicaments) for treatment of osteoporosis or Paget's disease which comprise one or more substances which completely or partly inhibit the chloride channel CIC-7, and to medicaments for treatment of neurological and neuromuscular diseases and other nerve diseases and psychotropic pharmaceuticals which comprise one or more substances which completely or partly inhibit the chloride channel CIC-3, CIC-4, CIC-6 and/or CIC-7. The medicaments comprise the active compounds in a formulation suitable for oral or intravenous administration, optionally together with pharmaceutically tolerated carrier substances.

The invention is explained in more detail below with the aid of examples.

EXAMPLES

Example 1

Figure 1:
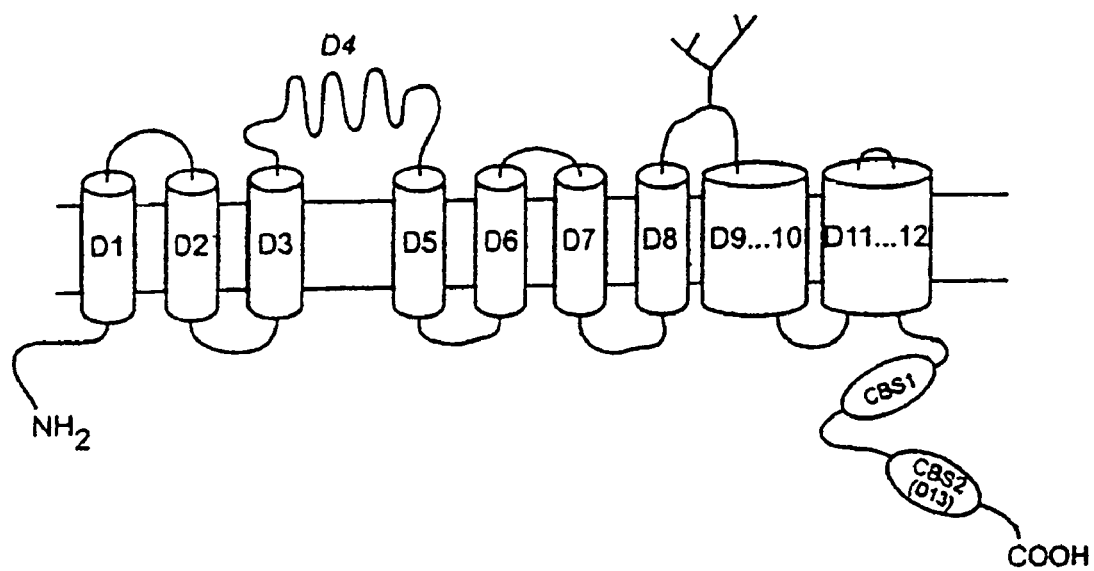
FIG. 1: Transmembrane topology model of CLC channels according to the biochemical study of Schmidt-Rose and Jentsch (T. Schmidt-Rose and T. J. Jentsch, Proc. Natl. Acad. Sci. USA 94 (1997) 7633-7638). N- and C-termini are located intracellularly. Initial hydropathy analysis of CIC-0 showed the presence of up to 13 transmembrane domains (D1-D13). Apart from some prokaryotic CICs, all known CIC proteins have two CBS domains (cf. A. Bateman, Trends Biochem. Sci. 22 (1997) 12-13 and C. P. Ponting, Mol. Med. 75 (1997) 160163) on the C terminus.

Protocol for Generating Knock-Outs by the Example of CIC-7

The CIC-7 knock-out mouse was produced by standard methods which are well-known to the skilled person and are described in detail, inter alia, in method books (cf. e.g. publication (78)). This technique requires several steps. In the first step a DNA construct which, in addition to the target sequence (in this case the genomic sequence of the mouse which contains the gene which codes for the CIC-7 channel), contain appropriate selection markers. In the second step an allele of the target gene is modified in pluripotent embryonal stem cells of the mouse by homologous recombination with the aid of this DNA construct such that it can no longer code for a functional protein. In the third step these recombinant embryonal stem cells are injected into mouse blastocysts, which are then transplanted into the uterus of pseudo-pregnant foster mothers (mice). These then give birth to descendants which are chimaeric, i.e. In addition to the genetically modified cells which originate from the stem cells injected, also contain normal, genetically non-manipulated cells of the blastocysts injected. These chimaeric mice are paired with normal "wild-type" (WT) mice. The descendants are tested (e.g. by southern blotting or by PCR techniques) as to whether the genetically modified, that is, to say functionally destroyed, gene has been inherited via the germ line. In the positive case these are now heterozygotic animals in which the channel gene on one of the two chromosomes is destroyed. Heterozygotic mice are crossed with one another to finally obtain homozygotic knock-out animals in which the corresponding channel genes are destroyed on both chromosomes.

In the case of the CIC-7 KO mouse, the construct was prepared as follows: With the aid of a rat cDNA probe (protein sequence published in reference (79)); Accession No. for protein and cDNA: Z67744 GenBank), a commercially obtainable genomic phage library in the vector λFIXII of the mouse strain 129/Sv (Stratagene, 11011 North Torrey Pines Road, La Jolla, Calif. 92037, USA) was scanned by standard methods of plating out, stripping off filters and hybridization with the radioactively labelled cDNA probe. Several phage clones which hybridized under high stringency were isolated, purified and analysed with standard methods of restriction mapping, partial sequencing and amplification of selected fragments by the PCR. A genomic clone which contained a piece approximately 14 kb in size of the genomic sequence of CIC-7, including the exon 2 (cf. (80)), was selected for preparation of the construct. For this, the genomic clone was digested with the two restriction enzymes BglII and BsrGI, as a result of which the part of the sequence which contains the coding exons 3, 4, 5, 6 and 7 was removed. This part was replaced with a DNA fragment approximately 1.6 kb in size which contains a neomycin resistance cassett driven by the phosphoglycerate promoter, by ligating the cassette into the genomic sequence by appropriate enzymatic reactions using standard processes. After transformation of bacteria with the corresponding vector containing this construct, bacterial colonies containing the correct construct were isolated, the DNA was extracted, and after digestion with HindIII, a thymidine kinase cassette was attached at the 5' end of the construct for negative selection. After renewed transformation, isolation and checking of the now finished construct, pluripotent embryonal stem cells (mouse) were transfected with it by electroporation and plated out and multiplied under appropriate culture conditions (culture on "feeder layers" in the presence of leukaemia inhibitory factor (LIF) to prevent differentiation). The cells were selected with G418 (selection for the presence of the neomycin resistance cassette) and gancyclovir (selection for the absence of the thymidine kinase cassette). Resistant clones were isolated, drawn out and analysed by southern blot analysis for homologous recombination on the CIC-7 locus. Correct clones in which the CIC-7 gene on one chromosome was destroyed (i.e. exons 3-7 were replaced by the neomycin cassette), were expanded by growing and injected into mouse blastocysts, as described above, under microscopic control with micromanipulators. The subsequent procedure was as described above. Since the genetic modification was inherited via the germ line, a CIC-7 KO mouse was produced in this way. The absence of the CIC-7 channel protein was demonstrated with the aid of a specific antibody established against an amino-terminal peptide of CIC-7. The CIC-7 KO mouse unexpectedly showed the phenotype of a potent osteopetrosis, accompanied by a retina degeneration and signs of degenerative changes in the central nervous system.

Example 2

Generation of a CIC3 KO Mouse

In a manner similar to that described in example 1, a CIC-3 KO mouse in which exon 3, which codes for sequences in the first transmembrane domain (cf. publications (83) and (84)), was deleted was also produced. This construct furthermore leads to a premature stop in translation, so that a very small, truncated protein was predicted. CIC-3 protein was no longer to be detected in the KO mouse with a specific antibody established against an amino-terminal peptide of CIC-3. The CIC-3 KO mouse showed a degeneration of the hippocampus and a degeneration of the retina. It was possible to demonstrate that the CIC-3 chloride channel occurs in intracellular, predominantly endosomal compartments and synaptic vesicles. pH measurements showed that the absence of CIC-3 caused a reduction In the acidification of synaptic vesicles.

REFERENCES (1) Clarke L L, Grubb B R, Gabriel S E, Smithies O, Koller B H, Boucher R C (1992) Defective epithelial chloride transport in a gene-targeted mouse model of cystic fibrosis. Science 257:1125-1128.
(2) Dorin J R, Dickinson P, Alton E W, Smith S N, Geddes D M, Stevenson B J, Kimber W L, Fleming S, Clarke A R, Hooper M L, et al (1992) Cystic fibrosis in the mouse by targeted insertional mutagenesis. Nature 359:211-215
(3) Ratcliff R, Evans M J, Doran J, Wainwright B J, Williamson R, Colledge W H (1992) Disruption of the cystic fibrosis transmembrane conductance regulator gene in embryonic stem cells by gene targeting. Transgenic Res. 1:177-181.
(4) Ratcliff R, Evans M J, Cuthbert, A W, MacVinish U, Foster D, Anderson JR, Colledge W H (1993) Production of a severe cystic fibrosis mutation in mice by gene targeting. Nature Genet. 4:3541.
(5) Matsumura Y, Uchida S, Kondo Y, Miyazaki H, Ko S B, Hayama A, Morimoto T, Liu W. Arisawa M, Sasaki S, (5) Marumo F (1999) Overt nephrogenic diabetes insipidus in mice lacking the CLC-K1 chloride channel. Nature Genet. 21:95-98.

(6) Brenner R, Perez G J, Bonev A D, Eckman D M, Kosek J C, Wiler S W, Patterson A J, Nelson M T, Aldrich R W (2000) Vasoregulation by the beta1 subunit of the calcium-activated potassium channel. Nature 407:870-876.

(7) Lee M P, Ravenel J D, Hu R J, Lustig L R, Tomaselli G, Berger. R D, Brandenburg S A, Utzi T J, Bunton T E, Umb C, Francis H, Gorelikow M, Gu H, Washington K, Argani P, Goldenring J R, Coffey R J, Feinberg AP (2000) Targeted disruption of the kylqt1 gene causes deafness and gastric hyperplasia in mice. J Clin Invest 106:1447-1455.

(8) Piwon N, GOnther W, Schwake M, Bösl MR, Jentsch T J (2000) CIC-5 CI—channel disruption impairs endocytosis In a mouse model for Dent's disease. Nature 408:369-373.

(9) Steinmeyer K, Lorenz C, Pusch M, Koch M C, Jentsch T J (1994) Multfineric structure of CIC-1 chloride channel revealed by mutations in dominant myotonia congenita (Thomsen). EMBO J. 13:737-743.

(10) Gronemeier M, Condie A, Prosser J, Steinmeyer K, Jentsch T J, Jockusch H (1994) Nonsense and missense mutations in the muscular chloride channel gene CIC-1 of myotonic mice. J Biol Chem 269:5963-5967.

(11) Lorenz C, Meyer-Kleine C, Steinmeyer K, Koch M C, Jentsch T J (1994) Genomic organization of the human muscle chloride channel CIC-1 and analysis of novel mutations leading to Becker-type myotonia. Hum Mol Genet 3:941-946.

(12) Meyer-Kleine C, Steinmeyer K, Ricker K, Jentsch T J, Koch M C. (1995) Spectrum of mutations in the major human skeletal muscle chloride channel gene (CLCN1) leading to myotonia. Am J Hum Genet. 57:1325-1334.

(13) Pusch M, Steinmeyer K, Koch M C, Jentsch T J. (1995) Mutations in dominant human myotonia congenita drastically alter the voltage dependence of the CIC-1 chloride channel. Neuron 15:1455-1463.

(14) Uoyd S E, Pearce S H, Fisher S E, Steinmeyer K, Schwappach B, Scheinman S J, Harding B, Bolino A, bevoto M, Goodyer P, Rigden S P, Wrong O, Jentsch T J, Craig I W, Thakker R V. A common molecular basis for three inherited kidney stone diseases. Nature 379:445449.

(15) Lloyd S E, Pearce S H, Gunther W, Kawaguchi H, Igarashi T, Jentsch T J, Thakker R V. (1997) Idiopathic low molecular weight proteinuria associated with hypercalciuric nephrocalcinosis in Japanese children is due to mutations of the renal chloride channel (CLCN5). J Clin Invest. 99:967-974.

(16) Uoyd S E, Gunther W, Pearce S H, Thomson A, Bianchi M L, Bosio M, Craig I W, Fisher S E, Scheinman S J, Wrong O, Jentsch T J, Thakker R V. (1997) Characterisation of renal chloride channel, CLCN5, mutations in hypercalciuric nephrolithiasis (kidney stones) disorders. Hum Mol Genet 6:1233-1239.

(17) Schmidt-Rose T, Jentsch T J. (1997) Reconstition of functional voltage-gated chloride channels from complementary fragments of CLC-1. J Biol Chem 272:20515-20521.

(18) Schwappach B, Stobrawa S, Hechenberger M, Steinmeyer K, Jentsch T J.(1998) Golgi localization and functionally important domains in the NH2 and COOH terminus of the yeast CLC putative chloride channel Gef1p. J Biol Chem 273:15110-15118.

(19) Kubisch C, Schmidt-Rose T, Fontaine B. Bretag A H, Jentsch T J. (1998) CIC-1 chloride channel mutations in myotonia congenita: variable penetrance of mutations shifting the voltage dependence. Hum Mol Genet. 7:1753-1760.

(20) Igarashi T, Gunther W, Sekine T, Inatomi J, Shiraga H, Takahashi S, Suzuki J, Tsuru N, Yanagihara T, Shimazu M, Jentsch T J, Thakker R V.(1998) Functional characterization of renal chloride channel, CLCN5, mutations associated with Dent's Japan disease. Kidney Int. 54:1850-1856.

(21) Friedrich T, Breiderhoff T, Jentsch T J.(1999) Mutational analysis demonstrates that CIC-4 and CIC-5 directly mediate plasma membrane currents. J Biol Chem 274:896-902.

(22) Yamamoto K, Cox J P, Friedrich T, Christie P T, Bald M, Houtman P N, Lapsley M J, Patzer L, Tsimaratos M, VanT Hoff W G, Yamaoka K, Jentsch T J, Thakker R V. (2000) Characterization of renal chloride channel (CLCN5) mutations in Dents disease. J Am Soc Nephrol 11:1460-1468.

(23) Piwon N, Günther W, Schwake M, Bosl M R, Jentsch TJ.(2000) CIC-5 CI-channel disruption impairs endocytosis in a mouse model for Dent's disease. Nature 408:369-373.

(24) Fahike C.(2000) Molecular mechanisms of ion conduction In CIC-type chloride channels: lessons from diseaseausing mutations. Kidney Int 57:780-786.

(25) Jen K Y, Gewirtz AM. (2000) Suppression of gene expression by targeted disruption of messenger RNA: available options and current strategies. Stem Cells 18:307-319.

(26) Marschall P, Thomson J B, Eckstein F. Inhibition of gene expression with ribozymes. Cell Mol Neurobiol. 14:523-538.

(27) Lewalle P, Marfiat P (1993) Inhibition of P210 expression in chronic myeloid leukaemia: oligonucleotides and/ or transduced antisense sequences. Leuk Lymphoma 11 Suppl 1:139-43.

(28) Montrose-Rafizadeh C, Kole J, Bartkowsid L M, Lee L H, Blackmon D L, Behnken S E, Gearhart J D, Cohn J A, Montrose M H (1997). Gene targeting of a CFTR allele in HT29 human epithelial cells. J Cell Physiol 170:299-308

(29) Luyckx V A, Leclercq B, Dowland L K, Yu A S (1999) Diet-dependent hypercalciuria in transgenic mice with reduced CLC5 chloride channel expression. Proc Natl Acad Sci USA 96:12174-12179

(30) Liu R. U W, Karin N J, Bergh J J, Adler-Storthz K, Farach-Carson M C (2000) Ribozyme ablation demonstrates that the cardiac subtype of the voltage-sensitive calcium channel is the molecular transducer of 1,25-dihydroxyvitamin D3-stimulated calcium influx in osteoblastic cells. J Biol Chem 275:8711-8718

(31) Nakao M, Furukawa K, Satoh E, Ono K, Iijima T (2000) Inhibition by antisense oligonucleotides of plasma membrane Ca2+ ATPase in vascular endothelial cells. Eur J Pharmacol 387:273-277.

(32) Tottene A, Volsen S, Pietrobon D (2000) alpha1E subunits form the pore of three cerebellar R-type calcium channels with different pharmacological and permeation properties. J Neurosci 20:171-178.

(33) Brussaard A B (1997) Antisense oligonucleotides induce functional deletion of ligand gated ion channels in cultured neurons and brain explants. J Neurosci Methods. 71:55-64.

(34) Vincent A, Lautermilch N J, Spitzer N C (2000) Antisense suppression of potassium channel expression demonstrates its role in maturation of the action potential. J Neurosci 20:6087-6094.

(35) Wang L, Chen L, Jacob T J (2000) The role of CIC-3 in volume activated chloride currents and volume regulation in bovine epithelial cells demonstrated by antisense inhibition. J. Physiol. 524: 63-75.

(36) Leconte L, Barnstable C J.(2000) Impairment of rod cGMP-gated channel alpha-subunit expression leads to photoreceptor and bipolar cell degeneration. Invest Ophthalmol Vis Sci 41:917-926.

(37) Gokhan S, Song Q, Mehler M F (1998) Generation and regulation of developing immortalized neural cell lines. Methods 16:345-358.

(38) Katakura Y. Alam S, Shirahata S. (1998) Immortalization by gene transfection. Methods Cell Biol 57:69-91.

(39) Yeager T R, Reddel R R (1999) Constructing immortalized human cell lines. Curr Opin Biotechnol 10:465469.

(40) Jat P S, Noble M D, Atallots P, Tanaka Y, Yannoutsos N, Larsen L, Kioussis D. (1991) Direct derivation of conditionally immortal cell lines from an H-2 Kb-tsA58 transgenic mouse. Proc Natl Acad Sci USA 88:5096-5100.

(41) Whitehead R H, VanEeden P E, Noble M D, Ataliotis P, Jat PS. (1993) Establishment of conditionally immortalized epithelial cell lines from both colon and small intestine of adult H-2Kb-tsA58 transgenic mice. Proc Natl Acad Sci USA 90:587-591.

(42) D'Abaco G M, Whitehead R H, Burgess A W (1996) Synergy between Apc min and an activated ras mutation is sufficient to induce colon carcinomas. Mol Cell Biol 16:884-891.

(43) Vandewalle A.(1999) Immortalized kidney cells derived from transgenic mice harboring L-type pyruvate kinaseand vimentin promoters. Exp Nephrol 7:386-393.

(44) Miesenbock G, De Angelis D A, Rothman J E (1998) Visualizing secretion and synaptic transmission with pH-sensitive green fluorescent proteins. Nature 394: 192-195.

(45) Uopis J, McCaffery J M, Miyawaki A, Farquhar M G, Tsien RY. (1998) Measurement of cytosolic, mitochondrial, and Golgi pH in single living cells with green fluorescent proteins. Proc Natl Acad Sci USA. 95:6803-6808.

(46) Kneen M, Farinas J, U Y, Verkman A S (1998) Green fluorescent protein as a noninvasive intracellular pH indicator. Biophys J 74:1591-1599.

(47) Wu M M, Uopis J, Adams S R, McCaffery J M, Teter K, Kulomaa M S, Machen T E, Moore H P, Tsien R Y.(2000) Studying organelle physiology with fusion protein-targeted avidin and fluorescent biotin conjugates. Methods Enzymol. 327:546-564.

(48) Schapiro F B, Grinstein S.(2000) Determinants of the pH of the Goigi complex. J Biol Chem 275:21025-21032.

(49) Demaurex N, Furuya W. D'Souza S, Bonifacino J S, Grinstein S (1998) Mechanism of acidification of the trans-Golgi network (TGN). In situ measurements of pH using retrieval of TGN38 and furin from the cell surface. J Biol Chem 273:2044-2051.

(50) Diwu Z, Chen C S, Zhang C, Kiaubert D H, Haugland RP. (1999) A novel acidotropic pH indicator and its potential application in labeling acidic organelles of live cells. Chem Biol 6:411-418.

(51) Overly C C, Lee K D, Berthiaume E, Hollenbeck PJ. (1995) Quantitative measurement of intraorganelle pH in the endosomal-iysosomal pathway in neurons by using ratiometric imaging with pyranine. Proc Natl Acad Sci USA 92:3156-3160.

(52) Boyde A, Ali N N, Jones S J.(1984) Resorption of dentine by isolated osteoclasts in vitro. Br Dent J 156:216-220

(53) Chambers T J, Revell P A, Fuller K, Athanasou N A. (1984) Resorption of bone by isolated rabbit osteoclasts. J Cell Sci. 1984 March;66:383-399.

(54) Sun L, Adebanjo O A, Moonga B S, Corisdeo S, Anandatheerthavarada H K, Biswas G, Arakawa T, Hakeda Y, Koval A, Sodam B, Bevis P J, Moser A J, Lai F A, Epstein S, Troen B R, Kumegawa M, Zaidi M (1999) CD38/ADP-ribosyl cyclase: A new role in the regulation of osteoclastic bone resorption. J Cell Biol 146:1161-1172

(55) Okazaki R, Toriumi M, Fukumoto S, Miyamoto M, Fujita T, Tanaka K, Takeuchi Y (1999) Thiazolidinediones inhibit osteoclast-like cell formation and bone resorption in vitro. Endocrinology 140:5060-5065

(56) Udagawa N, Takahashi N, Jimi E, Matsuzaki K, Tsurukai T, Itoh K, Nakagawa N, Yasuda H, Goto M, Tsuda E, Higashio K, Gillespie M T, Martin T J, Suda T (1999) Osteoblasts/stromal cells stimulate osteoclast activation through expression of osteoclast differentiation factor/RANKL but not macrophage colony-stimulating factor receptor activator of NF-kappa B ligand. Bone 25:517-523

(57) Redey S A, Razzouk S, Rey C, Bemache-Assollant D, Leroy G, Nardin M, Coumot G (1999) Osteoclast adhesion and activity on synthetic hydroxyapatite, carbonated hydroxyapatite, and natural calcium carbonate: relationship to surface energies. J Biomed Mater Res 45:140-147

(58) llvesaro J, Vaananen K, Tuukkanen J (2000) Bone-resorbing osteoclasts contain gap-junctonal connexin-43. J Bone Miner Res 15:919-926.

(59) Baron R, Neff L, Louvard D, Courtoy PJ. (1985) Cell-mediated extracellular acidification and bone resorption: evidence for a low pH in resorbing lacunae and localization of a 100-kD lysosomal membrane protein at osteoclast ruffled border. J. Cell Biol. 101:2210-2222.

(60) Inoue M, Yoshida H, Akisaka T (1999) Visualization of acidic compartments in cultured osteoclasts by use of an acidotrophic amine as a marker for low pH. Cell Tissue Res 298:527-537.

(61) Laitala-Leinonen T. Lowik C, Papapoulos S, Vaananen H K (1999) Inhibition of intravacuolar acidification by antisense RNA decreases osteoclast differentiation and bone resorption in vitro. J Cell Sci 112:3657-3666.

(62) Shioi J, Naito S, Ueda T. (1989) Glutamate uptake into synaptic vesicles of bovine cerebral cortex and electrochemical potential difference of proton across the membrane. Biochem J. 258:499-504.

(63) Tabb J S, Kish P E, Van Dyke R, Ueda T. (1992) Glutamate transport into synaptic vesicles. Roles of membrane potential, pH gradient, and intravesicular pH. J Blol Chem. 267:15412-15418.

(64) Hartinger J, Jahn R. (1993) An anion binding site that regulates the glutamate transporter of synaptic vesicles. J Biol Chem. 268:23122-23127.

(65) Maycox P R, Deckwerth T, Hell J W, Jahn R. (1988) Glutamate uptake by brain synaptic vesicles. Energy dependence of transport and functional reconstitution in proteoliposomes. J. Biol. Chem. 263:15423-15428.

(66) Hell J W, Maycox P R, Stadler H, Jahn R.(1988) Uptake of GABA by rat brain synaptic vesicles isolated by a new procedure. EMBO J. 7:3023-3029.

(67) Hell J W, Maycox P R, Jahn R.(1990) Energy dependence and functional reconstitution of the gamma-aminobutyric acid carrier from synaptic vesicles. J. Biol. Chem. 265:2111-2117

(68) Thomas-Reetz A, Hell J W, During M J, Walch-Solimena C, Jahn R, De Camilli P.(1993) A gamma-aminobutyric acid transporter driven by a proton pump is present in synaptic-like microvesicles of pancreatic beta cells. Proc Natl Acad Sci USA. 90:5317-5321.

(69) Mellman I (1992) The importance of being acid: the role of acidification in intracellular membrane traffic. J. exp. Biol. 172: 39-45.

(70) Presley J F, Mayor S, Dunn K W, Johnson L S, McGraw T E, Maxfield FR. (1993) The End2 mutation in CHO cells slows the exit of transferrin receptors from the recycling compartment but bulk membrane recycling is unaffected. J Cell Biol 122:1231-1241.

(71) Presley J F, Mayor S, McGraw T E, Dunn K W, Maxfield F R. (1997) Bafilomycin A1 treatment retards transferrin receptor recycling more than bulk membrane recycling. J. Biol. Chem. 272:13929-13936.

(72) Johnson L S, Dunn K W, Pytowski B, McGraw T E. (1993) Endosome acidification and receptor trafficking: bafilomycin A1 slows receptor externalization by a mechanism involving the receptor's internalization motif. Mol Biol Cell 4:1251-1266.

(73) Chapman R E, Munro S. (1994) Retrieval of TGN proteins from the cell surface requires endosomal acidification. EMBO J. 13:2305-2312.

(74) Clague M J, Urbe S, Aniento F, Gruenberg J. (1994) Vacuolar ATPase activity is required for endosomal carrier vesicle formation. J. Biol. Chem. 269:21-24.

(75) Tycko B, Maxfield F R (1982) Rapid acidification of endocytotic vesicles containing $\alpha_2$-macroglobulin. Cell 28: 643-651.

(76) Zen K, Biwersi J, Periasamy N, Verkman A S (1992) Second messengers regulate endosomal acidification in Swiss 3T3 fibroblasts. J Cell Biol 119: 99-110.

(77) Siegel M S, Isacoff E Y (1997) A genetically encoded optical probe of membrane voltage. Neuron 19:735-741.

(78) Gene Targeting. A Practical Approach. Editor Joyner, A. L. IRL Press at Oxford University Press (Oxford, New York, Tokyo) (1993).

(79) Brandt S, Jentsch T J (1995) CIC-6 and CIC-7 are two novel broadly expressed members of the CLC chloride channel family. FEBS Letters 377:15-20.

(80) Komak U, Bosl M R, Kubisch C.(1999) Complete genomic structure of the CLCN6 and CLCN7 putative chloride channel genes. Biochim Biophys Acta 1447:100-106.

(81) Reimer R J, Fon E A, Edwards R H. (1998) Vesicular neurotransmitter transport and the presynaptic regulation of quantal size. Curr Opin Neurobiol. 8:405412.

(82) Gasnier B. (2000) The loading of neurotransmitters into synaptic vesicles. Biochimie 82:327337.

(83) Kawasaki M, Uchida S, Monkawa T, Miyawaki A, Mikoshiba K, Mammo F, Sasaki S. (1994) Cloning and expression of a protein kinase C-regulated chloride channel abundantly expressed in rat brain neuronal cells. Neuron. 12:597404.

(84) Borsani G, Rugarii E I, Taglialatela M, Wong C, Ballabio A.(1995) Characterization of a human and murine gene (CLCN3) sharing similarities to voltage-gated chloride channels and to a yeast integral membrane protein. Genomics. 27:131-141.

(85) Sterrer S, Henco K. (1997) Fluorescence correlation spectroscopy (FCS)—a highly sensitive method to analyze drug/target interactions. J Recept Signal Transduct Res. 17:511-520

(86) Kask P, Palo K, Ullmann D, Gall K. (1999) Fluorescence-intensity distribution analysis and its application in biomolecular detection technology. Proc Natl Acad Sci USA. 96:13756-13561.

(87) Palo K, Mets U, Jager S, Kask P, Gall K (2000) Fluorescence intensity multiple distributions analysis: concurrent determination of diffusion times and molecular brightness. Biophys J 79:2858-2866.

(88) Schaerti S. Meyer-Almes FJ, LopezCalle E, Siemers A, Kramer J (2000) A novel and robust homogeneous fluorescence-based assay using nanoparticles for pharmaceutical screening and diagnostics. J Biomol Screen 5:227-238.

(89) Kardsson R.(1994) Real-time competitive kinetic analysis of interactions between low-molecular-weight ligands in solution and surface-immobilized receptors. Anal Biochem. 221:142-151.

(90) Beerheide W, Bernard H U, Tan Y J, Ganesan A, Rice W G, Ting AE. (1999) Potential drugs against cervical cancer: zinc-ejecting inhibitors of the human papillo-mavirus type 16 E6 oncoprotein. J Natl Cancer Inst. 91:1211-1220.

(91) Deckert F, Legay F.(2000) Development and validation of an IL-6 immuno-receptor assay based on surface plasmon resonance. J Pharm Biomed Anal. 23:403-412.

(92) Frostell-Kardsson A, Remaeus A, Roos H, Andersson K, Borg P, Hamalainen M, Karlsson R.(2000) Biosensor analysis of the interaction between immobilized human serum albumin and drug compounds for prediction of human serum albumin binding levels. J Med Chem. 43:1986-1992.

(93) Markgren P O, Hamalainen M, Danielson UH. (2000) Kinetic analysis of the interaction between HIV-1 protease and inhibitors using optical biosensor technology. Anal Biochem. 2000 Mar 1;279(1):71-8.

(94) Williams C. (2000) Biotechnology match making: screening orphan ligands and receptors. Curr Opin Biotechnol 11:42-46.

(95) Van Noorden C J, Vogels I M, Everts V, Beertsen W. (1987) Localization of cathepsin B activity in fibroblasts and chondrocytes by continuous monitoring of the formation of a final fluorescent reaction product using 5-nitrosalicylaldehyde. Histochem J 19:483-487.

(96) Xia L, Kilb J, Wex H, U Z, Upyansky A, Breuil V, Stein L, Palmer J T, Dempster D W, Bromme D (1999) Localization of rat cathepsin K In osteoclasts and resorption pits: inhibition of bone resorption and cathepsin K-activity by peptidyl vinyl sulfones. Biol Chem. 1999 June;380(6): 679-87.

The invention has been described in detail with reference to preferred embodiments thereof. However, it will be appreciated that those skilled in the art, upon consideration of this disclosure, may make modifications and improvements within the spirit and scope of the invention. All references disclosed herein are incorporated by reference.

The invention claimed is:

1. An in-vitro cell or cell line, in which there is expression of a functional chloride channel C1C-7, or a cell membrane preparation or an in vitro cell vesicle of said cell or cell line; wherein said cell or cell line
   (a) has been genetically modified to contain a transgene construct that overexpresses functional C1C-7; and at least one of the following of (b) and (c):
   (b) has been genetically modified to contain a transgene construct that directly reduces expression of functional chloride channels C1C-3; or
   (c) has been genetically modified to contain a transgene construct that directly reduces expression of functional chloride channel C1C-6;
   wherein the cell or cell line exhibits higher levels of expression of functional C1C-7 than of functional C1C-3 or functional C1C-6.

2. A cell, or a cell line, as claimed in claim 1, in which the functional chloride channel C1C-7 is expressed, but in which one or both of functional chloride channels C1C-3 and C1C-6 is not expressed or is expressed to only a reduced extent.

3. A cell, or a cell line, as claimed in claim 2, which has been genetically modified to contain transgene constructs that directly reduce expression of both functional C1C-3 and functional C1C-6, wherein the cell or cell line exhibits higher levels of expression of functional C1C-7 than of functional C1C-3 and higher expression of functional C1C-7 than of functional C1C-6.

4. A cell, or a cell line according to claim 1, which has been genetically modified to contain transgene constructs that directly reduce expression of each of the functional chloride channels C1C-3, C1C-4, C1C-5 and C1C-6, wherein the cell or cell line exhibits higher levels of expression of functional C1C-7 than of each of functional C1C-3, functional C1C-4, functional C1C-5 and functional C1C-6.

5. A cell, or a cell line, according to claim 1, in which functional chloride channel C1C-7 is expressed, but in which functional chloride channels C1C-3, C1C-4, C1C-5 and C1C-6 are not expressed or are expressed to only a reduced extent.

6. A cell, or a cell line according to claim 4, which has been genetically modified to contain transgene constructs that directly reduce expression of each of functional chloride channels C1C-1, C1C-2, C1C-Ka, C1C-Kb, C1C-3, C1C-4, C1C-5 and C1C-6, wherein the cell or cell line exhibits higher levels of expression of functional C1C-7 than of each of functional C1C-1, functional C1C-2, functional C1C-Ka, functional C1C-Kb, functional C1C-3, functional C1C-4, functional C1C-5 and functional C1C-6.

7. An in vitro cell, or a cell line, in which there is expression of a functional chloride channel C1C-3, or a cell membrane preparation or an in vitro cell vesicle of said cell or cell line; wherein said cell or cell line:
   (a) has been genetically modified to contain a transgene construct that overexpresses functional C1C-3; and
   (b) has been genetically modified to contain a transgene construct that directly reduces expression of functional chloride channel C1C-7; wherein the cell or cell line exhibits higher levels of expression of the functional C1C-3 than of functional C1C-7.

8. A cell, or a cell line, as claimed in claim 7, which has been genetically modified to contain a transgene construct that directly reduces expression of functional chloride channel C1C-7.

9. An in vitro cell, or a cell line in which there is expression of a functional chloride channel C1C-4, or a cell membrane preparation or an in vitro cell vesicle of said cell or cell line; wherein said cell or cell line:
   (a) has been genetically modified to contain a transgene construct that overexpresses functional C1C-4; and
   (b) has been genetically modified to contain a transgene construct that directly reduces expression of functional chloride channel C1C-7; wherein the cell or cell line exhibits higher levels of expression of functional C1C-4 than of functional C1C-7.

10. A cell, or a cell line, as claimed in claim 9, which expresses the chloride channel C1C-4, but does not express functional chloride channel C1C-7.

11. A cell, or a cell line, as claimed in claim 9 which expresses the chloride channel C1C-4, and which has been genetically modified to contain transgene constructs that directly reduce expression of each of functional chloride channels C1C-3, C1C-5, C1C-6 and C1C-7.

12. An in vitro cell, or a cell line in which there is expression of a functional chloride channel C1C-6, or a cell membrane preparation or an in vitro cell vesicle of said cell or cell line; wherein said cell or cell line:
   (a) has been genetically modified to contain a transgene construct that overexpresses functional C1C-6; and
   (b) has been genetically modified to contain a transgene construct that directly reduces expression of functional chloride channel C1C-7; wherein the cell or cell line exhibits higher levels of expression of functional C1C-6 than of functional C1C-7.

13. A cell, or a cell line, as claimed in claim 12, which expresses the chloride channel C1C-6, but does not express functional chloride channel C1C-7.

14. A cell, or a cell line, as claimed in claim 12, which expresses the chloride channel C1C-3 and the chloride channel C1C-6, but does not express or expresses only to a reduced functional extent functional chloride channel C1C-7.

15. A cell, or a cell line, as claimed in claim 14, which expresses functional chloride channels ClC-1, ClC-2, ClC-Ka, ClC-Kb, ClC-3, ClC-4, ClC-5 and ClC-6, but does not express or expresses only to a reduced extent functional chloride channel ClC-7.

16. A cell, or a cell line, as claimed in claim 7, which expresses the chloride channel ClC-3, and which has been genetically modified to contain transgene constructs that directly reduce expression of each of functional chloride channels ClC-4, ClC-5, ClC-6 and ClC-7.

17. A cell, or a cell line, as claimed in claim 12, which expresses the chloride channel ClC-6, and which has been genetically modified to contain transgene constructs that directly reduce expression of each of functional chloride channels ClC-3, ClC-4, ClC-5 and ClC-7.

18. A method for the identification and testing of substances suitable for inhibiting the chloride channel ClC-7, which method comprises contacting substances to be tested with cells, cell lines, cell membranes, or cell vesicles as claimed in claim 1 and measuring the effect of said substances on the activity of chloride channels in said cells, cell lines, cell membranes, or cell vesicles.

19. A method as claimed in claim 18, for the identification and testing of active compounds for treatment of osteoporosis or Paget's disease.

20. A method for the identification and testing of substances suitable for inhibiting the chloride channel ClC-3, which method comprises contacting substances to be tested with cells, cell lines, cell membranes, or cell vesicles as claimed in claim 7 and measuring the effect of said substances on the activity of chloride channels in said cells, cell lines, cell membranes or cell vesicles.

21. A method for the identification and testing of substances suitable for inhibiting the chloride channel ClC-6, which method comprises contacting substances to be tested with cells, cell lines, cell membranes, or cell vesicles as claimed in claim 12 and measuring the effect of said substances on the activity of chloride channels in said cells, cell lines, cell membranes, or cell vesicles.

22. A method for the identification and testing of substances suitable for inhibiting the chloride channel ClC-4, which method comprises contacting substances to be tested with cells, cell lines, cell membranes, or cell vesicles as claimed in claim 9 and measuring the effect of said substances on the activity of chloride channels in said cells, cell lines, cell membranes or cell vesicles.

23. A method as claimed in claim 18 or any one of claims 20 to 22, for the identification and testing of active compounds which are suitable as psychotropic pharmaceuticals.

24. A process for the identification and testing of substances which are suitable for inhibiting one or more chloride channels from the group consisting of ClC-3, ClC-4, ClC-6 and/or ClG-7, in which:
   a) on cells according to any one of claims 1, 7, 9 and 12, the luminal pH of the compartments which express the channel and/or the potential across the membrane enclosing the channel is measured,
   b) the cells are brought into contact with a substance and
   c) the luminal pH of the compartments which express the channel and/or the potential across the membrane enclosing the channel is measured again on the cells,
   the difference between the pH and/or the membrane potential before and after addition of the substance determining the activity of the substance.

25. A process according to claim 24, wherein the pH is measured by accumulation of substances in compartments with a particular pH or detection of indicator substances which are formed in pH-dependent reactions in the compartments.

26. A process according to claim 24, wherein the potential is measured using potential-sensitive dyestuffs or protein-coded potential sensors.

* * * * *

UNITED STATES PATENT AND TRADEMARK OFFICE
CERTIFICATE OF CORRECTION

| | | |
|---|---|---|
| PATENT NO. | : 7,534,425 B2 | Page 1 of 1 |
| APPLICATION NO. | : 10/622377 | |
| DATED | : May 19, 2009 | |
| INVENTOR(S) | : Thomas J. Jentsch | |

It is certified that error appears in the above-identified patent and that said Letters Patent is hereby corrected as shown below:

On the title page of the patent, Item (30), the Foreign Priority Application Data, is not shown.

--January 23, 2001   (DE)   10102977-- should be listed.

Signed and Sealed this

Sixth Day of July, 2010

David J. Kappos
*Director of the United States Patent and Trademark Office*